(12) United States Patent
Kerwin et al.

(10) Patent No.: US 6,297,284 B1
(45) Date of Patent: Oct. 2, 2001

(54) DNA-CLEAVING ANTITUMOR AGENTS

(75) Inventors: Sean Michael Kerwin, Round Rock; Wendi M. David; Dalip Kumar, both of Austin, all of TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/533,723

(22) Filed: Mar. 23, 2000

Related U.S. Application Data

(63) Continuation-in-part of application No. 09/356,303, filed on Jul. 16, 1999.
(60) Provisional application No. 60/093,112, filed on Jul. 16, 1998.

(51) Int. Cl.[7] .................................................. A61K 31/13
(52) U.S. Cl. ......................... 514/638; 514/671; 564/248; 564/509
(58) Field of Search .................. 514/638, 671; 564/248, 509

(56) References Cited

U.S. PATENT DOCUMENTS 5,767,142 * 6/1998 LaVoie et al. ...................... 514/394

OTHER PUBLICATIONS

Kouvetakis et al., "Synthesis of ethynyl–substituted precursors to carbon–nitrogen–sulfur extended structures: Reactions of C3N3F3 and C2N2SC12 with alkali–metal (trimethylsilyl)acetylides", Chem. Mater. 1994, 6, 636–639.*

Bunten et al., "Synthesis, Optical absorption, Fluorescence, Quantum efficiency, and Electrical conductivity studies of Pyridine/Pyridinium Dialkylnyl organic and Pt(II)–Acetylide monomers and polymers", Macromolecules, 1996, 29, 2885–2893.*

* cited by examiner

*Primary Examiner*—Ralph Gitomer
*Assistant Examiner*—d Khare
(74) *Attorney, Agent, or Firm*—Benjamin Aaron Adler

(57) ABSTRACT

A chemical composition and method of use of the composition is described. The chemical composition includes an aza-enediyne, aza-enyne allene, or an aza-diallene. These compound are preferably non-hydrolyzable, cationic compounds that bind to nucleic acids. In addition it is believed that these compounds may undergo chemical reactions in the presence of a nucleic acid to generate reactive intermediates that cleave nucleic acids.

44 Claims, 35 Drawing Sheets

19 a. R = Ph;  b. R = CH$_2$CH$_2$CH=CHPh

R = Ph 65%
R = TMS 42%
R = TIPS 20%
R = p(Me)C$_6$H$_5$ 86%

84%

R = Ph
R = TMS
R = TIPS
R = p(Me)C$_6$H$_5$

AZB-001

AZB-002

AZB-003

AZB-008

AZB-009

AZB-016

AZB-017

DNA-CLEAVING ANTITUMOR AGENTS

CROSS-REFERENCE TO RELATED APPLICATIONS

This patent application claims benefit of priority of A CIP application U.S. Ser. No. 09/356,303, filed Jul. 16, 1999, which claims benefit of priority of provisional application U.S. Ser. No. 60/093,112, filed Jul. 16, 1998, now abandoned.

BACKGROUND OF THE INVENTION

1. Field of the Invention

The present invention generally relates to a method and compound for the treatment of cancer. More particularly, an embodiment relates to the use of DNA interactive compounds that bind to DNA and undergo a series of chemical reactions in the presence of DNA to generate reactive intermediates that cleave DNA.

2. Brief Description of the Related Art

In 1972 Robert Bergman and co-workers demonstrated the gas-phase thermal rearrangement of substituted 3-hexene-1,5-diynes (1A/1B, FIG. 1), and proposed the intermediacy of a 1,4-5 didehydrobenzene, 2 in this process (Jones and Bergman, 1972). Indirect evidence for the existence of a singlet 1,4-didehydrobenzene intermediate was provided by solution-phase CIDNP experiments, which afforded the substituted benzene products 3 (Lockhart and Bergman, 1981). Bergman's original finding has gained additional significance in light of the discovery of an entire class of antitumor antibiotics, exemplified by calicheamicin $\gamma_1^I$ (4, FIG. 2) (Lee, 1987) that exert their potent cytotoxic effects through a Bergman cyclization of an enediyne core to produce a 1,4-didehydrobenzene intermediate. This diradical abstracts hydrogen atoms from the DNA ribose backbone, resulting in DNA strand scission (Hangeland, 1992).

Although simple, acyclic enediynes generally require higher temperatures than is physiologically relevant for Bergman cyclization to take place, synthetic enediynes that are strained may cyclize and produce DNA cleaving diradicals under physiological conditions, (Nicolaou, Dai, Tsay, Estevez, and Wrasidlo, 1992) and large numbers of these reactive enediynes have been designed, synthesized, and evaluated for biological activity (Grissom, Gunawardena, Klingberg, and Huang, 1996). More recently, the synthetic utility of the Bergman cyclization has been explored, principally by Grissom, who has employed the 1,4-didehydrobenzene intermediates afforded by the Bergman cyclization of substituted 3-hexene-1,5-diynes and substituted 1,2-diethynylbenzenes in subsequent free radical reactions to rapidly construct polycyclic compounds (Grissom, Calkins, Huang, and McMillen, 1994).

A related diradical-generating cyclization of 1,2,4-triene-5-ynes, modeled on the presumed DNA strand scission chemistry of the neocarzinostatin chromophore (Edo, 1985) (5, FIG. 3), has been discovered by Myers and co-workers (Myers, 1989). These workers found that enyne allene 6 undergoes an exothermic conversion to the α,3-didehydrotoluene intermediate 7, which may either abstract hydrogen atoms from 1,4-cyclohexadiene to produce toluene (8) or combine with the cyclohexyldienyl radical to form the adduct 9 (FIG. 4). This Myers cyclization has been exploited by many workers in the design of simple diradical-generating compounds with demonstrable ability to cleave DNA under physiological conditions (Nicolaou, Maligres, Shin and Deleon, 1990). The Myers cyclization has also been employed synthetically by Grissom (Grissom, Klingberg, Huang, and Slattery, 1997) and Wang (Wang, Wang, Tarli, and Gannet, 1996) in the construction of polycyclic molecules.

Schmittel and co-workers, (Schmittel, et al., 1995) and others (Gillman, et al., 1995) have reported anomalous products 12, 13, and 14 of thermal cyclizations of enyne allenes 10 (FIG. 5). These products are more pronounced in cases where the enyne allene substituents R, $R^1$, or $R^2$ are large. In these cases, the enyne allenes undergo cyclization to the benzofulvalene biradical intermediate 11, the fate of which is dependent upon the nature of the substituents. Schmittel has demonstrated that enyne allenes that undergo this $C^2$–$C^6$ cyclization reaction are able to cleave DNA, presumably as a result of hydrogen atom abstraction by the diradical 11 (Schmittel, Maywald, and Strittmatter, 1997).

Despite the promise, both synthetic and biological, of the chemistry of enediynes and enyne allenes, heteroatom substituted variants of these systems have not been extensively explored. Moore (Moore, 1992) has found that the enyne ketenes 16, generated from thermolysis of cyclobutenones 15, afford quinones 18, through the intermediate diradicals 17 (FIG. 6). These cyclobutenones also exhibit DNA cleaving ability, presumably due to the ability of the diradical intermediates to abstract hydrogen atoms from the DNA backbone (Sullivan, 1994). Padwa (Padwa, 1993) and Nakatani (Nakatani, 1994) have used alternative routes to enyne ketenes, which were also found to afford cycloaromatized products through diradical intermediates.

In contrast to the oxo-substituted enyne allene system, few aza-substituted enediyne or enyne allenes had been reported prior to our work. Wang and co-workers had reported the failed attempt to coax nitrile (19, FIG. 7) to undergo an aza-Myers cyclization (Wang, Wang, and Sattsangi, 1996). Gillman and co-workers had reported similar findings for a related 2-allenyl cyanobenzene (Gillman and Heckhoff, 1996). Most recently, Wang and co-workers have shown that the ketenimine 20 gives products predicted by both an aza-Myers cyclization (21) and the $C_2$–$C^6$ cyclization (22) (FIG. 8) (Shi and Wang, 1998).

SUMMARY OF THE INVENTION

The synthesis and utility of novel aza-derivatives of enediynes, enyne allenes, and diallenes is described herein. The term "aza-derivative" is herein taken to mean aza-enediynes, aza-enyne allenes, and aza-diallenes. These aza-derivatives have the potential to generate novel reactive intermediates, and thus serve as an important tool in the study of these intermediates. In addition, these same intermediates may be harnessed to affect nucleic acid strand scission, and thus serve as the warhead of a new class of antitumor or antiviral compounds.

Aza-enediyne derivatives, in one embodiment, have the general structure:

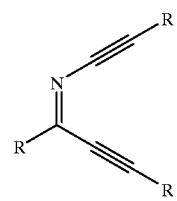

The parent structure includes an imine covalently coupled to two alkynyl groups. A variety of substitutents may be attached to the parent structure at the R positions. Any commonly known substituent may be placed upon the parent structure as long as the resulting compound is relatively stable.

The parent structure may also be formed as an iminium ion (i.e., a salt of the parent structure) having the structure:

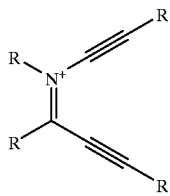

A variety of substitutents may be attached to the parent structure at the R positions. Any commonly known substituents may be placed upon the parent structure as long as the resulting compound is relatively stable. The nitrogen atom is either protonated, alkylated, or incorporated into a ring system.

Aza-enediyne derivatives, in another embodiment, have the isomeric parent structures:

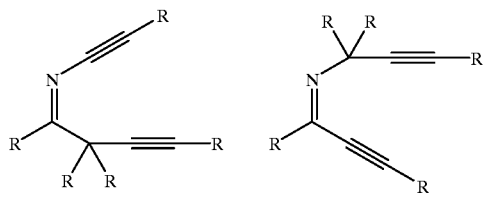

Each of the isomeric parent structures includes an imine covalently coupled to an alkynyl group and a propargyl group. The groups may be attached to either the nitrogen or the carbon as depicted above. A variety of substitutents may be attached to the parent structure at the R positions. Any commonly known substituent may be placed upon the parent structure as long as the resulting compound is relatively stable.

The parent structures may also be formed as an iminium ion (i.e., a salt of the parent structure) having the structures:

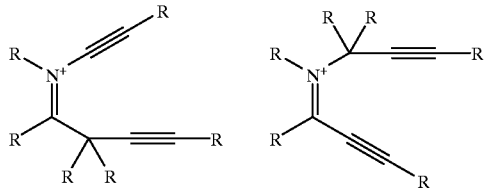

A variety of substitutents may be attached to the parent structures at the R positions. Any commonly known substituents may be placed upon the parent structure as long as the resulting compound is relatively stable. The nitrogen atom is either protonated, alkylated, or incorporated into a ring system.

Aza-enyne allene derivatives, in one embodiment, have the isomeric parent structures:

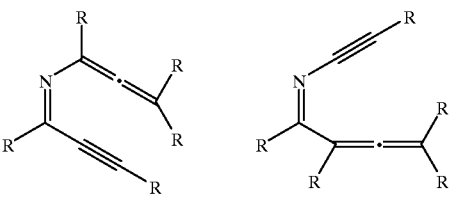

Each of the isomeric parent structures includes an imine covalently coupled to an alkynyl group and an allenyl group. The groups may be attached to either the nitrogen or the carbon as depicted above. A variety of substitutents may be attached to the parent structure at the R positions. Any commonly known substituent may be placed upon the parent structure as long as the resulting compound is relatively stable.

The parent structures may also be formed as an iminium ion (i.e., a salt of the parent structure) having the structures:

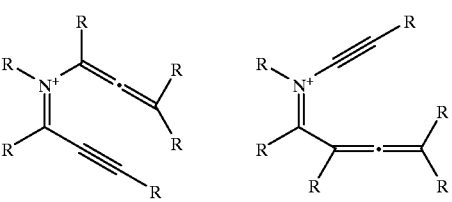

A variety of substitutents may be attached to the parent structures at the R positions. Any commonly known substituents may be placed upon the parent structure as long as the resulting compound is relatively stable. The nitrogen atom is either protonated, alkylated, or incorporated into a ring system.

Aza-diallene derivatives, in one embodiment, have the general structure:

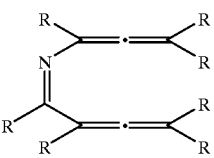

The parent structure includes an imine covalently coupled to two allene groups. A variety of substitutents may be attached to the parent structure at the R positions. Any commonly known substituent may be placed upon the parent structure as long as the resulting compound is relatively stable.

The parent structure may also be formed as an iminium ion (i.e., a salt of the parent structure) having the structure:

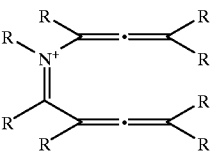

A variety of substitutents may be attached to the parent structure at the R positions. Any commonly known substituents may be placed upon the parent structure as long as the resulting compound is relatively stable. The nitrogen atom is either protonated, alkylated, or incorporated into a ring system.

In another embodiment, oligomeric aza-derivatives are compounds having a dimeric or oligomeric structure composed of aza-derivatives as defined above. Any of the R substitutents $R_1$, $R^2$, $R^3$, or $R^4$, may be used to link these compounds together. "Dimeric" structures refer to compounds in which two similar structures are joined together. "Oligomeric" structures refers to compounds on which two or more compounds having similar or different structures are linked together. The individual aza-derivatives may be linked together by a linking group.

The aza-derivatives may be used in the treatment of cancer and other proliferative diseases. In addition, these aza-derivatives may have uses in other disease states, such as viral and bacterial infections. These aza-derivatives may be used as fluorescent dyes, and by virtue of the diradical chemistry that they enter into, they may have utility in the manufacture of dye-fast fluorescent materials such as plastics and as biochemical probes for such techniques as FISH and flow cytometry. Also by virtue of the diradical intermediates that these aza-derivatives produce under very mild conditions, they may find utility as initiators of radical reactions, including polymerization reactions.

Where clinical application of aza-derivatives is undertaken, it will be necessary to prepare the complex as a pharmaceutical composition appropriate for the intended application.

Generally, the synthesis of the aza-derivatives is accomplished by reacting an imine with an electrophilic compound. The imines may be formed by reacting a carbonyl compound (e.g., a ketone or aldehyde) with a nucleophilic amine derivative. The reaction of a carbonyl with a nucleophilic amine may also be used to produce the aza-derivatives which are iminium salts.

The compounds are believed to show cytotoxic effects by cleaving nucleic acids. When a nucleic acid is treated with an aza-derivative the interaction of the nucleic acid with the aza-derivative may cause the derivative to undergo an aza-Bergman type reaction. The aza-Bergman reaction is believed to produce a diradical species. This diradical species is believed to interact with the nucleic acid causing cleavage of the nucleic acid strands. This mechanism of action may be useful in the treatment of cancer, viral infections or bacterial infections.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized above may be had by reference to certain embodiments thereof which are illustrated in the appended drawings. These drawings form a part of the specification. It is to be noted; however, that the appended drawings illustrate preferred embodiments of the invention and therefore are not to be considered limiting in their scope.

DETAILED DESCRIPTION OF THE INVENTION

Figure 1:
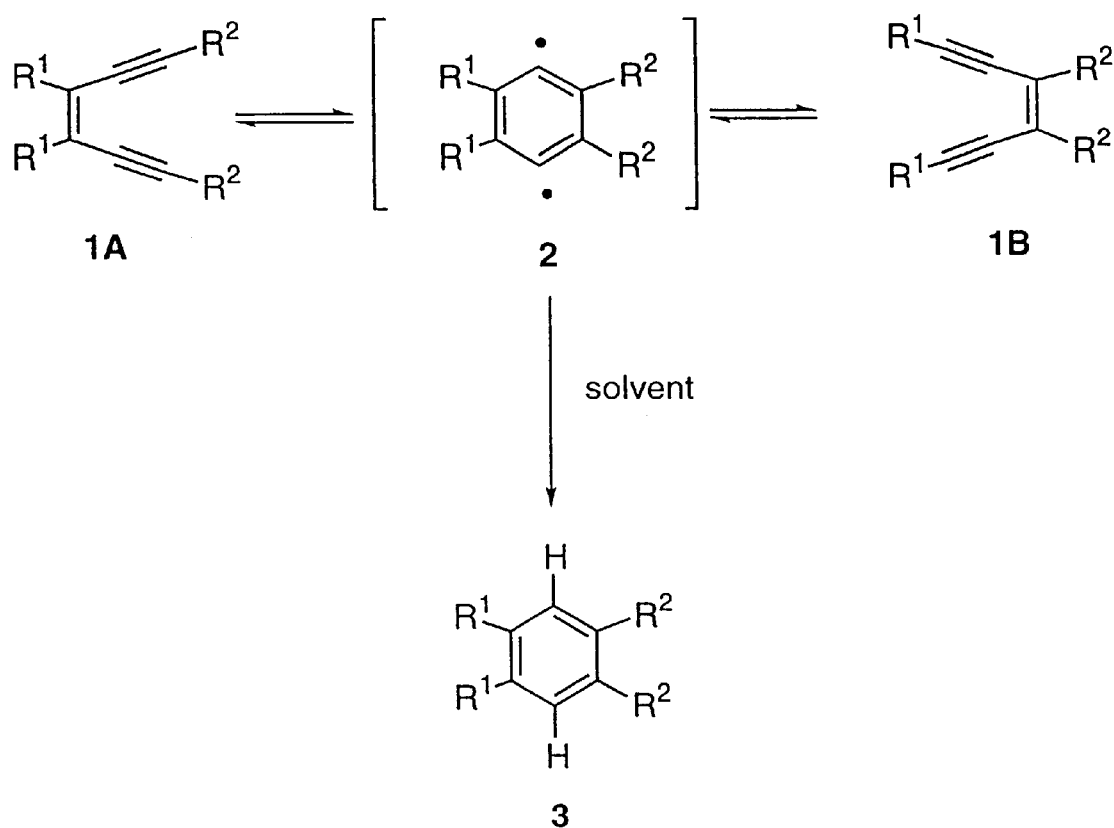
FIG. 1 depicts the gas-phase thermal rearrangement of substituted 3-hexene- 1,5-diynes.
Figure 2:
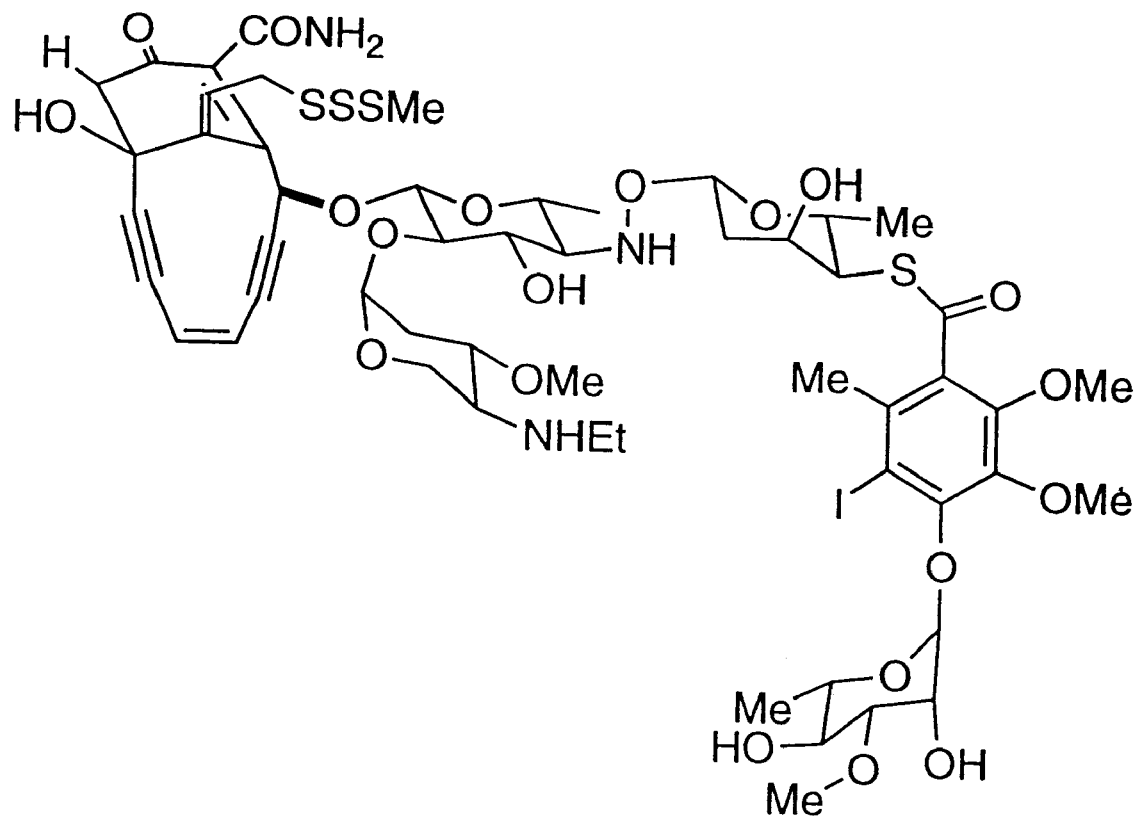
FIG. 2 depicts the molecule calicheamicin $\gamma_1^I$.
Figure 3:
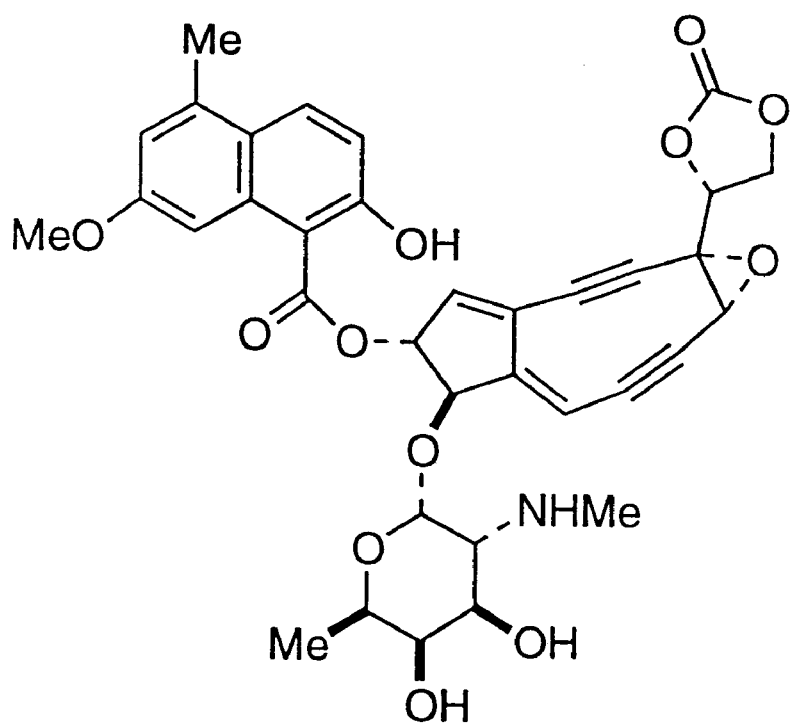
FIG. 3 depicts the neocarzinostatin chromophore.
Figure 4:
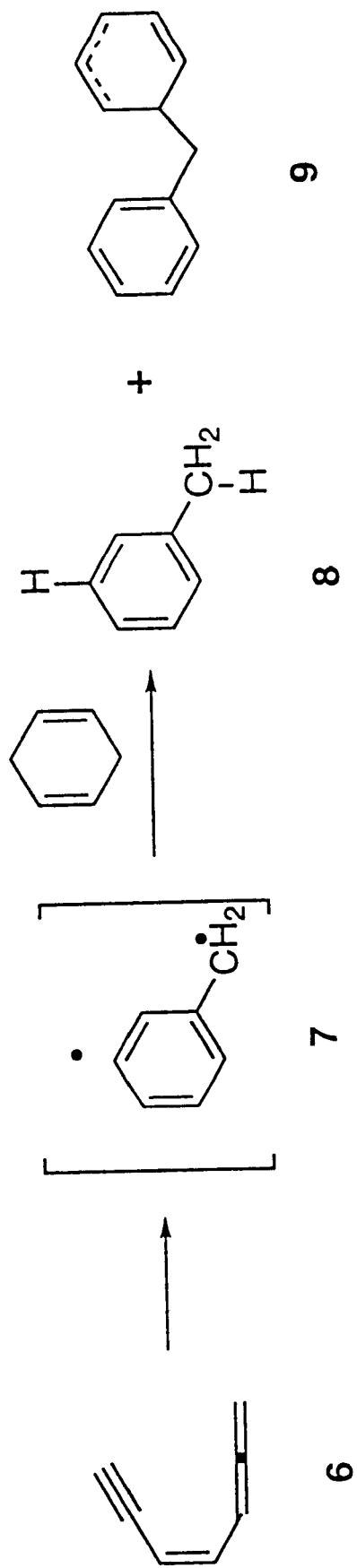
FIG. 4 depicts the diradical-generating cyclization of 1,2,4-triene-5-ynes.
Figure 5:
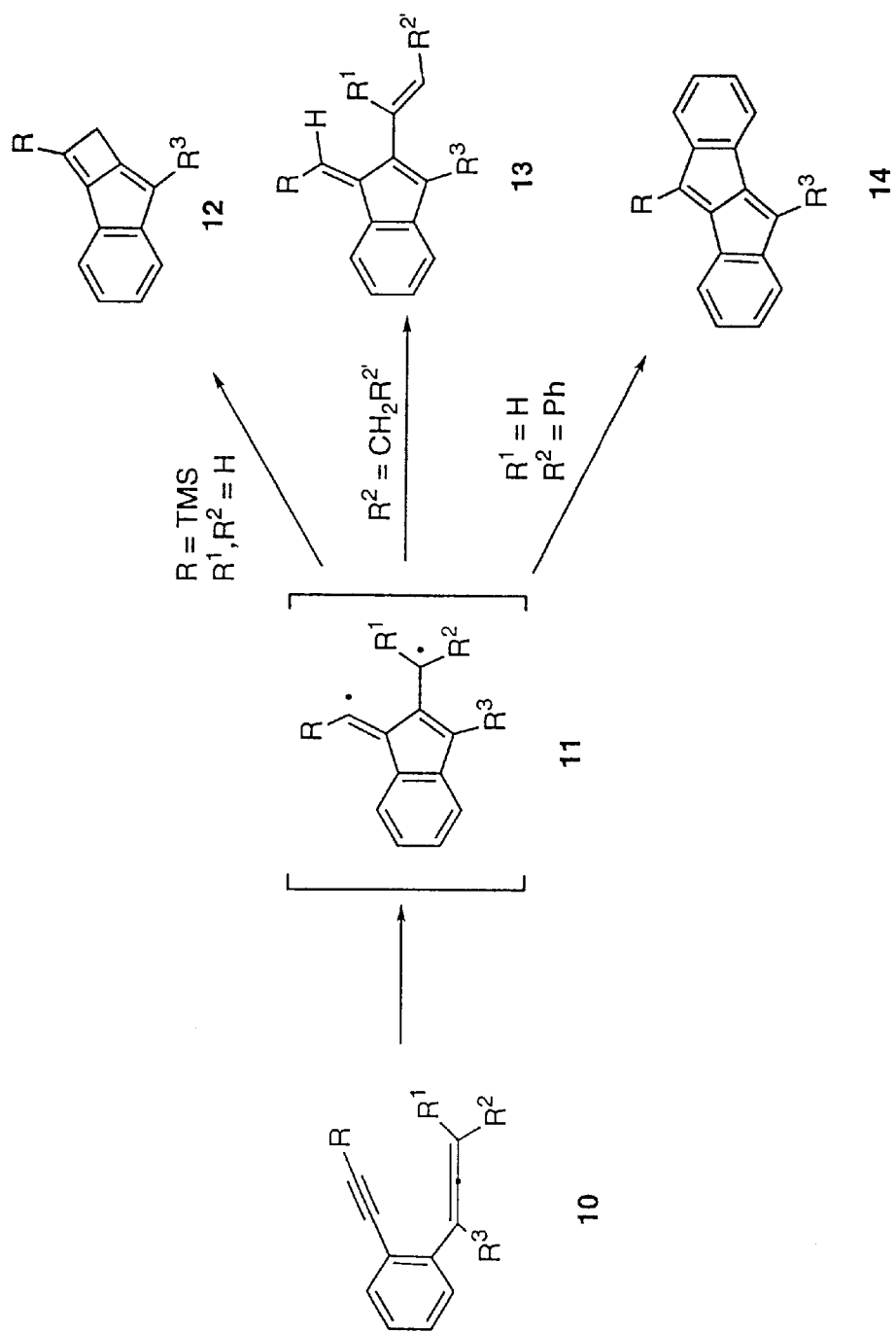
FIG. 5 depicts the thermal cyclizations of enyne allenes.
Figure 6:
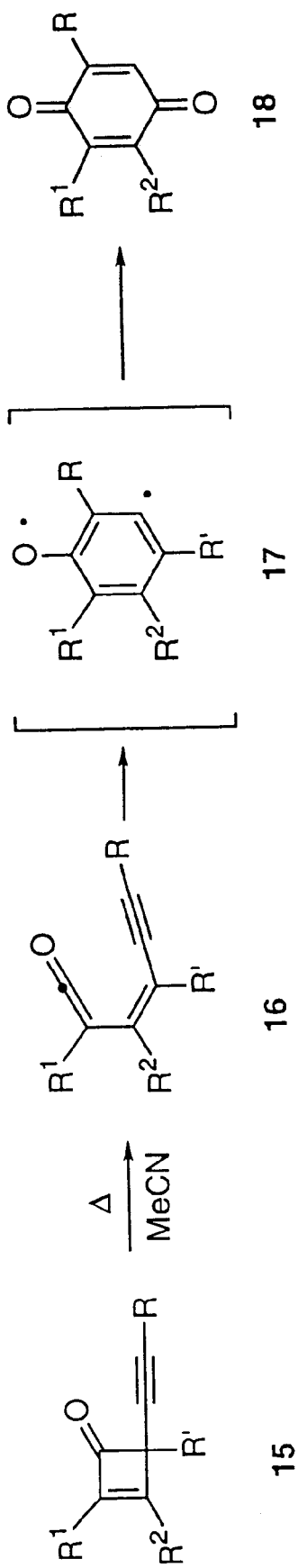
FIG. 6 depicts the rearrangement of enyne ketenes to afford quinones through intermediate diradicals.
Figure 7:
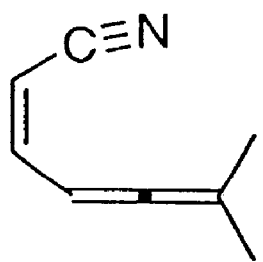
FIG. 7 depicts an allene nitrile.
Figure 8:
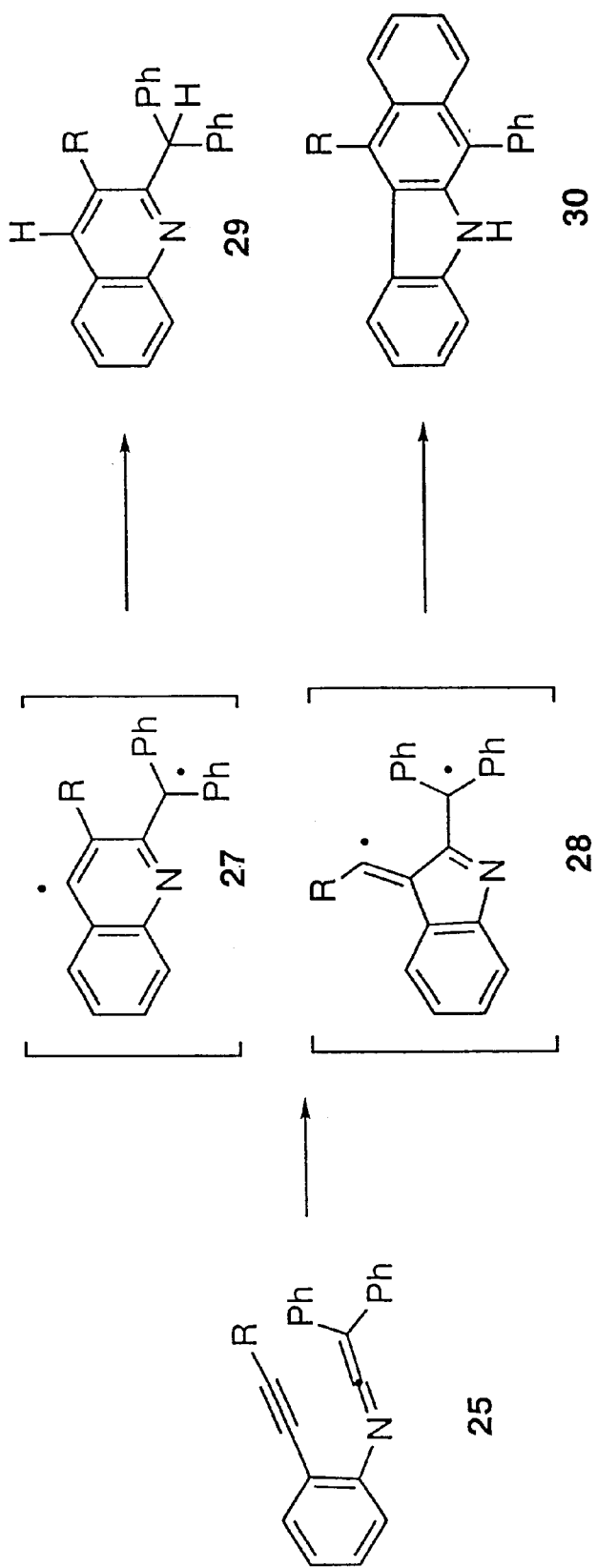
FIG. 8 depicts the reaction of a ketenimine to give products predicted by both an aza-Myers cyclization and a $C^2$–$C^6$ cyclization.

The synthesis and utility of novel aza-derivatives of enediynes, enyne allenes, and diallenes is described herein. Appropriately constructed aza-derivatives may undergo thermal reactions to produce diradical intermediates. The propensity of these aza-derivatives to undergo these diradical generating reactions, and the facility with which these diradical intermediates undergo free radical atom abstraction reactions or other reactions which result in DNA strand scission, is believed to depend upon the position of the nitrogen atom in the starting enediyne, enyne allene or diallene precursor, as well as on the nature of the substituents. The aza-Bergman cyclization has the advantage of occurring much more readily than the corresponding Bergman cyclization. Thus, these aza-derivatives may be capable of inducing DNA strand scission under physiological conditions.

In one embodiment, the aza-derivatives have the structure A:

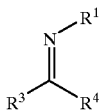
(A)

where $R^1$ and $R^4$ are independently:
a substituted-ethynyl group having the structure:

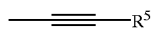

a substituted-allenyl group having the structure:

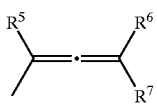

or a substituted-propargyl group having the structure:

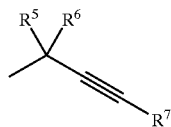

where $R^5$, $R^6$, and $R^7$ are independently hydrogen, alkyl, alkenyl, alkynyl, cycloalkyl, alkyl carbonyl, alkoxy carbonyl, phenyl, aryl, alkyl ($C_1$–$C_4$) aryl, hydroxy alkyl, a substituted hydroxyalkyl, an alkyl carboxylic acid derivative, an alkenyl carboxylic acid derivative, a nucleic acid interactive compound, a phosphine oxide, a sulfoxide, a sulfone, a heterocycle substituent, or where $R^5$, $R^6$, and $R^7$ may join with themselves or each other to form a 9–26 membered ring;

Alternatively, either $R^1$ or $R^4$ is independently:
a halogen, sulfonate ester, alkyl group, or
a substituted alkenyl group having the structure:

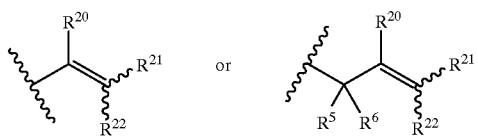

where $R^5$ and $R^6$ are as previously defined, $R^{20}$, $R^{21}$, and $R^{22}$ are independently a hydrogen, a halogen, a carboxylic acid derivative, a sulfonate ester derivative, a phosphoester derivative, or an alcohol which are capable of being converted into a substituted-ethynyl, substituted-allenyl, or substituted-propargyl group, either in vitro or in vivo, and either $R^1$ or $R^4$ is independently a substituted-ethynyl, a substituted-allenyl, or a substituted-propargyl; and where, in both cases, $R^3$ is $R^1$, alkyl, phenyl, aryl, alkyl ($C_1$–$C_4$) aryl, a heterocycle substituent and groups represented by the formulas —$OR^8$, —$SR^8$, —$NR^8R^9$ where $R^8$ and $R^9$ are independently hydrogen, alkyl, phenyl, aryl, alkyl ($C_1$–$C_4$) aryl, a heterocycle substituent, trifluoromethylsulfonyl, silyl, substituted-ethynyl, substituted-allenyl, substituted propargyl, a sugar, a nucleic acid interactive compound or a C-glycoside.

As used herein, "alkyl" is intended to include branched, cyclic and straight-chain saturated aliphatic hydrocarbon groups. "Alkenyl" is intended to include hydrocarbon chains of either a straight, cyclic, or branched configuration and one or more unsaturated carbon-carbon bonds which may occur in any stable point along the chain.

"Alkynyl" is intended to include hydrocarbon chains of either a straight, cyclic or branched configuration and one or more triple carbon-carbon bonds which may occur in any stable point along the chain.

"Cycloalkyl" is intended to include saturated ring groups, including mono-, bi-, or poly-cyclic ring systems, such as cyclopropyl, cyclobutyl, cyclopentyl, cyclohexyl, cycloheptyl, adamantyl, and cyclooctyl.

"Alkyl carbonyl" is intended to include an alkyl group of an indicated number of carbon atoms attached through a carbonyl group to the residue of the compound at the designated location.

"Alkoxy carbonyl" is intended to include an alkoxy group of an indicated number of carbon atoms attached through a carbonyl group to the residue of the compound at the designated location.

"Phenyl" is intended to include a benzene ring attached to the residue of the compound at the designated location.

"Aryl" is taken to include substituted aromatic ring systems, where the rings may be substituted with hydrogen, alkyl, alkenyl, alkynyl, cycloalkyl, alkyl carbonyl, alkoxy carbonyl, halogens, halogenated alkyl groups, an aryl ($C_1$–$C_4$) alkyl group, and groups represented by the formulas —$NO_2$, —CN, —SCN, and a heterocycle substituent —OR, —SR, —NR'R", —$CO_2$R, —RNC(=NR)NRR', and —C(=NR)NRR' where R is hydrogen, alkyl, alkyl ($C_1$–$C_4$) aryl, or aryl.

"Aryl ($C_1$–$C_4$) alkyl)" is intended to include an aryl group attached through a $C_1$–$C_4$ alkyl group to the residue of the compound at the designated location.

"Carbocyclic" is intended to mean any stable 3 to 8 membered monocyclic or bicyclic ring system, or 7 to 14 membered bicyclic or tricyclic ring system, or up to 26 membered polycyclic carbon ring, any of which may be saturated (such as cyclohexyl), partially unsaturated (such as cyclohexenyl), or aromatic. Examples of such carbocycles include, but are not limited to, cyclopropyl, cyclopentyl, cyclohexyl, phenyl, biphenyl, naphthyl, indanyl, and adamantyl.

A "nucleic acid interactive compound" is defined herein as an oligonucleic acid, a peptide, a peptoid, an intercalator, a crown ether, a peptide nucleic acid, a G-quadruplex interactive agent, a triplex interactive agent, an RNA interactive agent, an RNA-DNA heteroduplex interactive agent, a DNA alkylating agent, an RNA alkylating agent, a DNA cleaving agent, an RNA cleaving agent, a DNA metalating agent, an RNA metalating agent, a DNA groove binding compound, a porphyrin, an aminoglycoside, a sugar, or an oligosaccharide.

"Hydroxy alkyl" is intended to mean compounds attached via a carbon having the general formula $C_nH_{2n}OH$, where n is a positive integer.

"Substituted hydroxyalkyl" is intended to mean compounds attached via a carbon having the general formula $C_nH_{2n}OR$, where n is a positive integer, and R is alkyl, aryl, aryl ($C_1$–$C_4$) alkyl, a heterocycle substituent, sulfonyl, or silyl.

"Alkyl carboxylic acid derivative" is intended to mean compounds attached via carbon having the general formula $C_nH_{2n}CO_2R$, where R is hydrogen, alkyl, aryl, aryl ($C_1$–$C_4$) alkyl, or amino, and n is a positive integer.

"Alkenyl carboxylic acid derivative" is intended to mean compounds attached via carbon having the general formula $C_nH_{[(2n-2)-q]}CO_2R$, where R is hydrogen, alkyl, aryl, aryl ($C_1$-$C_4$) alkyl or amino, where n is a positive integer and where q represent the number of double bonds which reside between the first carbon group and the terminal carboxylic acid derivative.

"Phosphine oxides" is intended to mean compounds attached via phosphorus having the general formula P(=O)RR' where R and R' are independently alkyl, phenyl, aryl, aryl ($C_1$-$C_4$) alkyl or —Oalkyl.

"Sulfoxides" is intended to mean compounds attached via sulfur having the general formula S(=O)R, where R is alkyl, phenyl, aryl, aryl ($C_1$-$C_4$) alkyl, or a heterocycle substituent.

"Sulfones" is intended to mean compounds attached via sulfur having the general formula —$SO_2R$, where R is alkyl, phenyl, aryl, aryl ($C_1$-$C_4$) alkyl, or a heterocycle substituent.

As used herein, the term "heterocycle" is intended to mean a stable 5- to 7- membered monocyclic or bicyclic ring or a 7- to 10-membered bicyclic ring which is either saturated or unsaturated, and which consists of carbon atoms and from 1 to 4 heteroatoms, such rings including any bicyclic group in which any of the above-defined heterocyclic rings is fused to a benzene ring.

The term "heteroatom" refers to nitrogen, oxygen, sulfur, or selenium atoms, where the nitrogen, sulfur and selenium atoms may optionally be oxidized, and the nitrogen may optionally be quaternized.

The term "heterocycle substituent" refers to a heterocycle which is covalently coupled to another organic molecule in place of a hydrogen or other substituent. Heterocycle substituents may be attached to its pendent group at any heteroatom or carbon atom which results in a stable structure. The heteroatom rings described herein may be substituted on carbon or on a nitrogen if the resulting compound is stable. Examples of heterocycle substituents include, but are not limited to, diazepine, oxazepine, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1 ,2,5-thiadiazinyl, acridinyl, azocinyl, benzofuranyl, benzoimidolyl, benzothiazolyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoquinolinyl (benzimidazolyl), isothiazolyl, isoxolyl, morpholinyl, naphthyridinyl, octahydroisoquinolinyl, oxazipine, oxazolidinyl, oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyyrolinyl, pyrrolyl, quinazolinyl, quinolinyl, quinoxzlinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, and xanthenyl. Also included are fused ring and spiro compounds containing, for example, the above heterocycles.

In another embodiment, the aza-derivative has the structure:

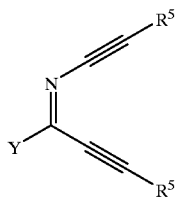

where each instance of $R^5$ is independently hydrogen, alkyl, alkenyl, alkynyl, cycloalkyl, alkyl carbonyl, alkoxy carbonyl, phenyl, aryl, aryl ($C_1$-$C_4$) alkyl, hydroxy alkyl, a substituted hydroxyalkyl, an alkyl carboxylic acid derivative, an alkenyl carboxylic acid derivative, a nucleic acid interactive compound, a phosphine oxide, a sulfoxide, a sulfone, aryl ($C_1$-$C_4$) alkyl, or a heterocycle substituent; where Y is $R^1$ alkyl, phenyl, aryl, aryl ($C_1$-$C_4$) alkyl, or a heterocycle substituent and groups represented by the formulas —$OR^8$, —$SR^8$, —$NR^8R^9$ where $R^8$ and $R^9$ are independently hydrogen, alkyl, phenyl, aryl, aryl ($C_1$-$C_4$) alkyl, trifluoromethylsulfonyl, silyl, substituted-ethynyl, substituted-allenyl, substituted propargyl, or a heterocycle substituent, a sugar, a nucleic acid interactive compound or a C-glycoside.

In an embodiment, Y is —OMe, —OTf, —SMe, $NMe_2$, phenyl, p-$MeC_4H_6$, p-$MeOC_4H_6$, p-t-$BuC_4H_6$, or p-$CF_3C_4H_6$; $R_1$ is phenyl or —$CH_2OTMS$; and $R^2$ is phenyl or —$CH_2CH_2CH=CHCO_2Me$. In another embodiment, Y is —$NR^3R^4$ where one of $R^3$ or $R^4$ is a substituted-ethynyl, substituted-allenyl, substituted propargyl. Examples of these compounds may have the structures:

where R, R', R", and R'" are independently hydrogen, alkyl, phenyl, aryl, aryl ($C_1$-$C_4$) alkyl, hydroxy alkyl, a substituted hydroxyalkyl, an alkyl carboxylic acid derivative and an alkenyl carboxylic acid derivative, aryl ($C_1$-$C_4$) alkyl, a heterocycle substituent or a nucleic acid interactive compound In another embodiment, Y is a heterocycle substituent. In an embodiment where Y is an heterocyclic compound, the compound may have the structure:

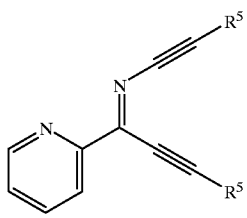

where each instance of $R^5$ is independently as previously defined.

In another embodiment, the aza-derivative has the structure:

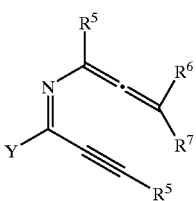

where each instance of $R^5$, $R^6$, and $R^7$ is independently hydrogen, alkyl, alkenyl, alkynyl, cycloalkyl, alkyl carbonyl, alkoxy carbonyl, phenyl, aryl, hydroxy alkyl, a substituted hydroxyalkyl, an alkyl carboxylic acid derivative, an alkenyl carboxylic acid derivative, a nucleic acid interactive compound, a phosphine oxide, a sulfoxide, a sulfone, aryl ($C_1$–$C_4$) alkyl, or a heterocycle substituent; where Y is $R^1$, alkyl, phenyl, aryl, a heterocycle substituent and groups represented by the formulas —$OR^8$, —$SR^8$, —$NR^8R^9$ where $R^8$ and $R^9$ are independently hydrogen, alkyl, phenyl, aryl, a sulfone, aryl ($C_1$–$C_4$) alkyl, a heterocycle substituent, trifluoromethylsulfonyl, silyl, substituted-ethynyl, substituted-allenyl, substituted propargyl, a sugar, a C-glycoside nucleic acid interactive compound.

In another embodiment, Y is Me; the ethynyl substituent $R^5$ is phenyl, $R^2$ and $R^3$ are hydrogen, and the allenyl substituent $R^5$ is —$POMe_2$ or Me.

In another embodiment, the aza-derivative has the structure:

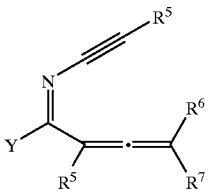

where each instance of $R^5$, $R^6$, and $R^7$ is independently hydrogen, alkyl, alkenyl, alkynyl, cycloalkyl, alkyl carbonyl, alkoxy carbonyl, phenyl, aryl, hydroxy alkyl, a substituted hydroxyalkyl, an alkyl carboxylic acid derivative, an alkenyl carboxylic acid derivative, a nucleic acid interactive compound, a phosphine oxide, a sulfoxide, a sulfone, aryl ($C_1$–$C_4$) alkyl, or a heterocycle substituent; where Y is $R^1$, alkyl, phenyl, aryl, aryl ($C_1$–$C_4$) alkyl, a heterocycle substituent and groups represented by the formulas —$OR^8$, —$SR^8$, —$NR^8R^9$ where $R^8$ and $R^9$ are independently hydrogen, alkyl, phenyl, aryl, a sulfone, aryl ($C_1$–$C_4$) alkyl, a heterocycle substituent, trifluoromethylsulfonyl, silyl, substituted-ethynyl, substituted-allenyl, substituted propargyl, a sugar, or a C-glycoside. In another embodiment, the aza-derivative has the structure:

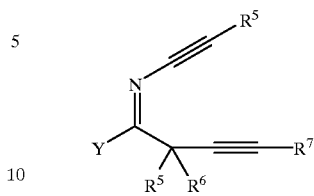

where each instance of $R^5$, $R^6$, and $R^7$ is independently hydrogen, alkyl, alkenyl, alkynyl, cycloalkyl, alkyl carbonyl, alkoxy carbonyl, phenyl, aryl, hydroxy alkyl, a substituted hydroxyalkyl, an alkyl carboxylic acid derivative, an alkenyl carboxylic acid derivative, a nucleic acid interactive compound, a phosphine oxide, a sulfoxide, a sulfone, aryl ($C_1$–$C_4$) alkyl, or a heterocycle substituent; where Y is $R^1$, alkyl, phenyl, aryl, aryl ($C_1$–$C_4$) alkyl, a heterocycle substituent and groups represented by the formulas —$OR^8$, —$SR^8$, —$NR^8R^9$ where $R^8$ and $R^9$ are independently hydrogen, alkyl, phenyl, aryl, aryl ($C_1$–$C_4$) alkyl, trifluoromethylsulfonyl, silyl, substituted-ethynyl, substituted-allenyl, substituted propargyl, a heterocycle substituent, a sugar, or a C-glycoside.

In another embodiment, the aza-derivative has the structure:

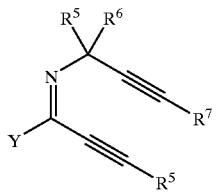

where each instance of $R^5$, $R^6$, and $R^7$ is independently hydrogen, alkyl, alkenyl, alkynyl, cycloalkyl, alkyl carbonyl, alkoxy carbonyl, phenyl, aryl, hydroxy alkyl, a substituted hydroxyalkyl, an alkyl carboxylic acid derivative, an alkenyl carboxylic acid derivative, a nucleic acid interactive compound, a phosphine oxide, a sulfoxide, a sulfone, aryl ($C_1$–$C_4$) alkyl, or a heterocycle substituent; and where Y is $R^1$, alkyl, phenyl, aryl, aryl ($C_1$–$C_4$) alkyl, a heterocycle substituent and groups represented by the formulas —$OR^8$, —$SR^8$, —$NR^8R^9$ where $R^8$ and $R^9$ are independently hydrogen, alkyl, phenyl, aryl, trifluoromethylsulfonyl, silyl, substituted-ethynyl, substituted-allenyl, substituted propargyl, a heterocycle substituent, a sugar, a C-glycoside, nucleic acid derivative.

In another embodiment, the aza-derivative has the structure:

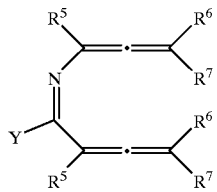

where each instance of $R^5$, $R^6$, and $R^7$ is independently hydrogen, alkyl, alkenyl, alkynyl, cycloalkyl, alkyl carbonyl, alkoxy carbonyl, phenyl, aryl, aryl ($C_1$–$C_4$) alkyl, hydroxy alkyl, a substituted hydroxyalkyl, an alkyl carboxylic acid derivative, an alkenyl carboxylic acid derivative, a nucleic acid interactive compound, a phosphine oxide, a sulfoxide, a sulfone, aryl ($C_1$–$C_4$) alkyl, a heterocycle substituent; and where Y is $R^1$, alkyl, phenyl, aryl, aryl ($C_1$–$C_4$) alkyl, a heterocycle substituent and groups represented by the formulas —$OR^8$, —$SR^8$, —$NR^8R^9$ where $R^8$ and $R^9$ are independently hydrogen, alkyl, phenyl, aryl, aryl ($C_1$–$C_4$) alkyl, trifluoromethylsulfonyl, silyl, substituted-ethynyl, substituted-allenyl, substituted propargyl, a heterocycle substituent, a sugar, a C-glycoside, or a nucleic acid derivative.

In another embodiment, the aza-derivatives have the salt structure B:

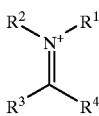

(B)

where $R^1$ and $R^4$ are independently a substituted-ethynyl group, a substituted-propargyl group or a substituted-allenyl group, each of these groups having the structures previously shown; where $R^5$, $R^6$, and $R^7$ (of the substituted-ethynyl group, the substituted-propargyl group and the substituted-allenyl group, as previously depicted) are independently hydrogen, alkyl, a substituted alkyl, alkenyl, alkynyl, cycloalkyl, alkyl carbonyl, alkoxy carbonyl, phenyl, aryl, aryl ($C_1$–$C_4$) alkyl, hydroxy alkyl, a substituted hydroxyalkyl, an alkyl carboxylic acid derivative, an alkenyl carboxylic acid derivative, a nucleic acid interactive compound, a phosphine oxide, a sulfoxide, a sulfone, aryl ($C_1$–$C_4$) alkyl, or a heterocycle substituent, and where $R^5$, $R^6$, and $R^7$ may join with themselves or each other to form a 9–26 membered ring.

Alternatively, either $R^1$ or $R^4$ is independently:

a halogen, sulfonate ester, alkyl group, or a substituted alkenyl group having the structure:

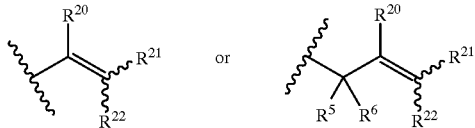

where $R^5$ and $R^6$ are as previously defined, $R^{20}$ $R^{21}$, and $R^{22}$ are independently a hydrogen, a halogen, a carboxylic acid derivative, a sulfonate ester derivative, a phosphoester derivative, or an alcohol which are capable of being converted into a substituted-ethynyl, substituted-allenyl, or substituted-propargyl group, either in vitro or in vivo, and either $R^1$ or $R^4$ is independently a substituted-ethynyl, a substituted-allenyl, or a substituted-propargyl; where in both cases $R^2$ is $R^1$, alkyl, phenyl, aryl, aryl ($C_1$–$C_4$) alkyl, a heterocycle substituent; where in both cases $R^3$ is $R^1$, alkyl, substituted alkyl, phenyl, aryl, aryl ($C_1$–$C_4$) alkyl, a heterocycle substituent, and groups represented by the formulas —$OR^8$, —$SR^8$, —$NR^8R^9$ where $R^1$ and $R^9$ are independently hydrogen, alkyl, phenyl, aryl, trifluoromethylsulfonyl, silyl, substituted-ethynyl, substituted-allenyl, substituted propargyl, a sugar, a C-glycoside, a nucleic acid interactive compound, an aryl ($C_1$–$C_4$) alkyl, or a heterocycle substituent; alternatively where, in both cases, $R^2$ and $R^3$ along with the iminium portion of the molecule may combine to form a heterocyclic ring, or a substituted heterocyclic ring. Examples of heterocycles which may be formed include, but are not limited to, diazepine, 1H-indazole, 2-pyrrolidone, 2H,6H-1,5,2-dithiazine, 2H-pyrrole, 3H-indole, 4-piperidone, 4aH-carbazole, 4H-quinolizine, 6H-1,2,5-thiadiazine, acridine, azocine ,benzimidazole, benzthiazole, benzofuran, benzothiophene, carbazole, chromane, chromene, cinnoline, decahydroquinoline, furan, furazane, imidazolidine, imidazoline, imidazole, indoline, indolizine, indole, isobenzofuran, isochromane, isoindoline, isoquinoline (benzimidazole), isothiazole, isoxole, morpholine, naphthyridine, octahydroisoquinoline, oxazipine, oxazolidine, oxazole, phenanthridine, phenanthroline, phenarsazine, phenazine, phenothiazine, phenoxathine, phenoxazine, phthalazine, piperazine, piperidine, pteridine, purine, pyran, pyrazine, pyrazolidine, pyrazoline, pyrazole, pyridazine, pyridine, pyrimidine, pyrrolidine, pyyroline, pyrrol, quinazoline, quinoline, quinoxaline, quinuclidine, carboline, tetrahydrofuran, tetrahydroisoquinoline, tetrahydroquinoline, tetrazole, thianthrene, thiazole, thiene, thiophene, triazine, and xanthene. Also included are fused ring and spiro compounds containing, for example, the above heterocycles. The term "substituted heterocyclic ring" refers to the heterocyclic rings described herein which are substituted on carbon or on a nitrogen if the resulting compound is stable.

Embodiments of the heterocycle ring include:

a benzazole ring having structure:

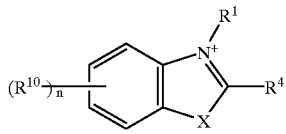

a pyridinium ring having structure:

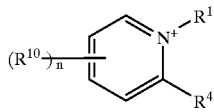

a (fused) heterocyclic ring having structure:

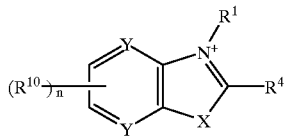

a tetrahydrobenzazole ring having structure:

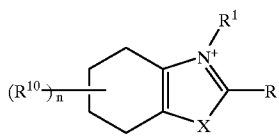

an amidine ring having structure:

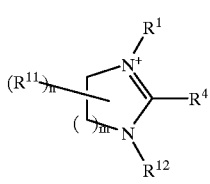

a purine ring having structure:

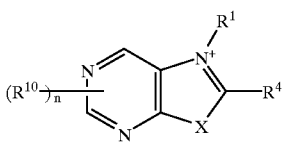

an isomeric purine ring having structure:

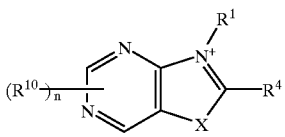

a pyrimidine ring, having structure:

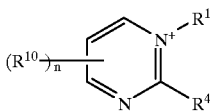

an imidazole ring having structure:

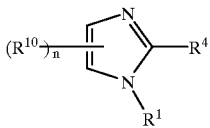

a thiazole or oxazole ring having structure:

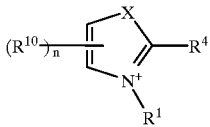

a triazole having the structure:

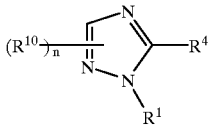

a bicyclic system having the structure:

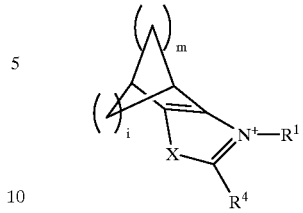

a pyridone ring system having the structure:

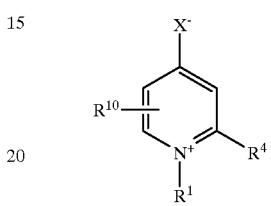

where X is oxygen, sulfur or $NR^{14}$; where Y is independently $CR^{10}$ or $NR^{14}$; $R^{10}$ is hydrogen, alkyl, substituted alkyl, alkenyl, alkynyl, cycloalkyl, $-NO_2$, $-CN$, $-SCN$, alkyl carbonyl, alkoxy carbonyl, halogens, halogenated alkyl groups, phenyl, aryl, a heterocycle substituent, a sugar, and groups represented by the formulas $-OR^{12}$, $-SR^{12}$, $-NR^{12}R^{13}$, $-CO_2R^{12}$, $-R^{12}NC(=NR^{12})NR^{12}R^{13}$, and $-C(=NR^{12})NR^{12}R^{13}$ where $R^{12}$ and $R^{13}$ are independently hydrogen, alkyl, phenyl, aryl, aryl ($C_1-C_4$) alkyl, or a heterocycle substituent, where $R^{11}$ is alkyl, phenyl, aryl, aryl ($C_1-C_4$) alkyl; where $R^{14}$ is H, alkyl, phenyl, aryl, aryl ($C_1-C_4$) alkyl, a heterocycle substituent, substituted-ethynyl, substituted-allenyl, substituted propargyl, sugar, C-glycoside or a nucleic acid.

In a preferred embodiment of the heterocyclic ring structure, $R^1$ is methyl and $R^4$ is a substituted-ethynyl group having the structure $-C\equiv C(Ph)$, or a substituted-alkenyl group having the structure $-CH=C(Ph)OCH_3$; $R^2$ $R^5$, $R^6$, and $R^7$ are as previously defined and $R^3$ is $-SR^8$, or $-NR^8R^9$, where $R^8$ is as previously defined, $R^9$ is methyl; and $R^2$ and $R^3$ along with parent iminium combine to form a benzimidazole, benzthiazole, thiazole or pyridine ring;

Compounds having this salt structure have an associated counter ion (e.g., an anion). Examples of counter ions include, but are not limited to, fluorine, chlorine, bromine, iodine, tetrafluoroborane, acetate, sulfonate, and phosphate.

Embodiments of the substituted heterocycle ring include:

an azole ring having the structures:

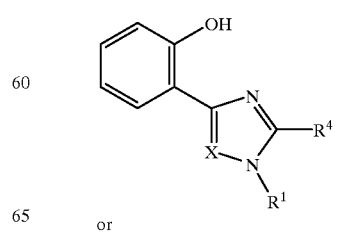

or

-continued

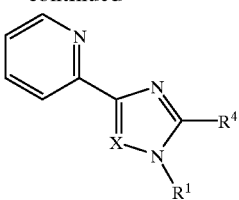

where X is a nitrogen or a carbon and the azole is substituted with a phenol or a pyridine ring.

In an embodiment, aza-derivatives have the structure:

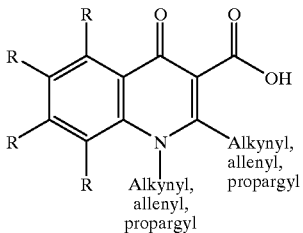

where alkynyl, allenyl, and propargyl refers to substituted alkynyl, substituted allenyl, and substituted propargyl groups having the previously described structures. R is hydrogen, alkyl, alkenyl, alkynyl, cycloalkyl, —$NO_2$, —CN, —SCN, alkyl carbonyl, alkoxy carbonyl, halogens, halogenated alkyl groups, aryl ($C_1$–$C_4$) alkyl, a heterocycle substituent, and groups represented by the formulas —$OR^2$, —$SR^{12}$, —$NR^{12}R^{13}$, —$CO_2R^{12}$, —$R^{12}NC(=NR^{12})NR^{12}R^{13}$, and —$C(=NR^{12})NR^{12}R^{13}$ where $R^{12}$ and $R^{13}$ are independently hydrogen, alkyl, phenyl, aryl, aryl ($C_1$–$C_4$) alkyl or a heterocycle substituent.

In another embodiment the aza-derivatives have the structure (B) in which either one of the groups $R^1$ and $R^4$ (but not both) is a substituted alkenyl group that can be converted to a substituted ethynyl group, a substituted allenyl group or a substituted propargyl group as previously defined. This substituted alkenyl group is designated 'R' in this embodiment.

In a preferred embodiment, the compounds have the following structures:

an azole

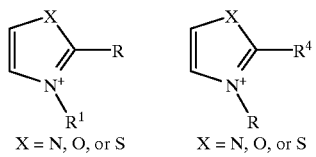

X = N, O, or S     X = N, O, or S a pyridine

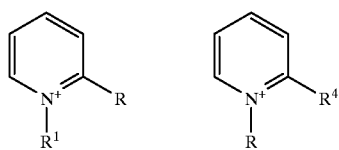

where $R^1$ and $R^4$ are substituted-ethynyl, substituted-allenyl, or substituted-propargyl groups, and R is a halogen, sulfonate ester, alkyl, alkenyl, or a group capable of being converted into either $R^1$ or $R^4$ as defined above.

In another preferred embodiment, the groups which may be converted into a substituted-ethynyl, substituted-allenyl, or substituted-propargyl have the following structures:

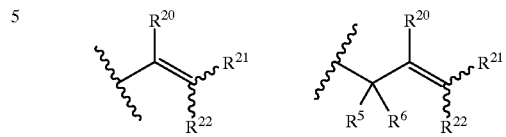

where $R^5$ and $R^6$ are as previously defined, $R^{20}$ $R^{21}$, and $R^{22}$ are independently a hydrogen, a halogen, a carboxylic acid derivative, a sulfonate ester derivative, a phosphoester derivative, or an alcohol.

In another embodiment, aza-derivative are compounds having a dimeric or oligomeric structure composed of compounds having the general structure A or B. Any of the R substitutents $R^1$, $R^2$, $R^3$, or $R^4$, may be used to link these compounds together. "Dimeric" structures refer to compounds in which two similar structures are joined together. "Oligomeric" structures refers to compounds in which two or more compounds having similar or different structures are linked together.

One embodiment of an oligomeric aza-derivative has the structure:

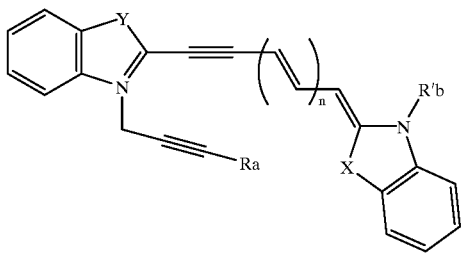

where X and Y are oxygen, sulfur, or $NR^{25}$, n=0 to 4, $R^a$ is hydrogen, alkyl, alkenyl, alkynyl, cycloalkyl, alkyl carbonyl, alkoxy carbonyl, phenyl, aryl, aryl ($C_1$–$C_4$) alkyl, hydroxy alkyl, a substituted hydroxyalkyl, an alkyl carboxylic acid derivative, an alkenyl carboxylic acid derivative, a nucleic acid interactive compound, a phosphine oxide, or a sulfoxide; and $R^b$ and $R^{25}$ are H, alkyl, phenyl, aryl, aryl ($C_1$–$C_4$) alkyl, substituted-ethynyl, substituted-allenyl, substituted propargyl, sugar, C-glycoside, or a nucleic acid interactive compound.

In another embodiment, an oligomeric aza-derivative has the structure:

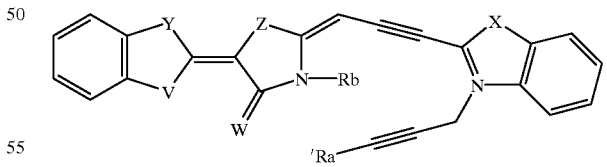

where X,Y, W, V, and Z are oxygen, sulfur, or $NR^{25}$, n=0 to 4, $R^a$ is hydrogen, alkyl, alkenyl, alkynyl, cycloalkyl, alkyl carbonyl, alkoxy carbonyl, phenyl, aryl, aryl ($C_1$–$C_4$) alkyl, hydroxy alkyl, a substituted hydroxyalkyl, an alkyl carboxylic acid derivative, an alkenyl carboxylic acid derivative, a nucleic acid interactive compound, a phosphine oxide, or a sulfoxide; and $R^b$ and $R^{25}$ are H, alkyl, phenyl, aryl, aryl ($C_1$–$C_4$) alkyl, substituted-ethynyl, substituted-allenyl, substituted propargyl, sugar, or C-glycoside.

In another embodiment, an oligomeric aza-derivative has the structure:

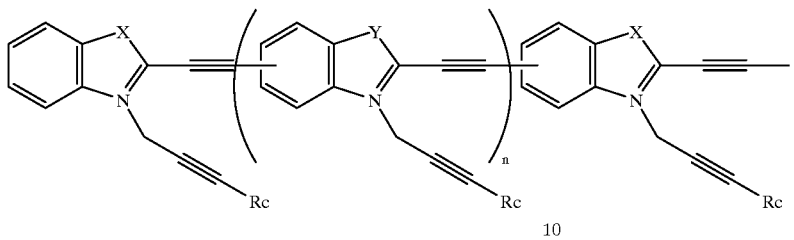

where X and Y are oxygen, sulfur, or $NR^{26}$, n=0 to 4, each instance of $R^c$ is independently hydrogen, alkyl, alkenyl, alkynyl, cycloalkyl, alkyl carbonyl, alkoxy carbonyl, phenyl, aryl, aryl ($C_1$–$C_4$) alkyl, hydroxy alkyl, a substituted hydroxyalkyl, an alkyl carboxylic acid derivative, an alkenyl carboxylic acid derivative, a nucleic acid interactive compound, a phosphine oxide, or a sulfoxide; and $R^{26}$ is H, alkyl, phenyl, aryl, substituted-ethynyl, substituted-allenyl, substituted propargyl, sugar, or C-glycoside.

In another embodiment, an oligomeric aza-derivative has the structure:

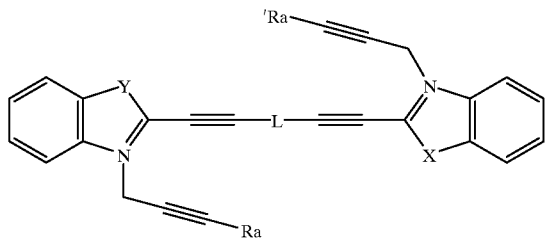

where X and Y are oxygen, sulfur, or $NR^{25}$, n=0 to 4, each instance of $R^a$ are hydrogen, alkyl, alkenyl, alkynyl, cycloalkyl, alkyl carbonyl, alkoxy carbonyl, phenyl, aryl, aryl ($C_1$–$C_4$) alkyl, hydroxy alkyl, a substituted hydroxyalkyl, an alkyl carboxylic acid derivative, an alkenyl carboxylic acid derivative, a nucleic acid to interactive compound, a phosphine oxide, or a sulfoxide; $R^{25}$ is H, alkyl, phenyl, aryl, aryl ($C_1$–$C_4$) alkyl, substituted-ethynyl, substituted-allenyl, substituted propargyl, sugar, or C-glycoside, and L is a linking group molecule, where L is a single bond, an alkyl, alkenyl, alkynyl, cycloalkyl, alkyl carbonyl, alkoxy carbonyl, phenyl, is aryl, aryl ($C_1$–$C_4$) alkyl, hydroxy alkyl, a substituted hydroxyalkyl, an alkyl carboxylic acid derivative, an alkenyl carboxylic acid derivative, or a heteroatom or heterocycle substituent.

In another embodiment, an oligomeric aza-derivative has the structure:

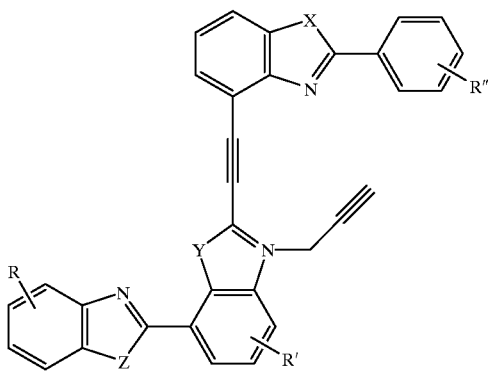

where X, Y, and Z are oxygen, sulfur, or $NR^{25}$, n=0 to 4, each instance of $R^d$ is independently hydrogen, alkyl, alkenyl, alkynyl, cycloalkyl, $-NO_2$, $-CN$, $-SCN$, alkyl carbonyl, alkoxy carbonyl, halogens, halogenated alkyl groups, and groups represented by the formulas $-OR^{12}$, $-SR^{12}$, $-NR^{12}R^{13}$, $-CO_2R^{12}$ where $R^{12}$ and $R^{13}$ are independently hydrogen, alkyl, phenyl, aryl, aryl ($C_1$–$C_4$) alkyl.

In another embodiment, an oligomeric aza-derivative has the structure:

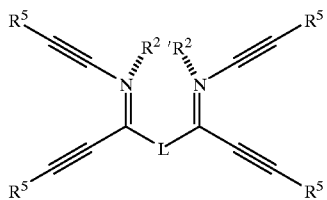

where R is hydrogen, alkyl, alkyl ($C_1$–$C_4$) aryl, alkenyl, alkynyl, cycloalkyl, alkyl carbonyl, alkoxy carbonyl, phenyl, aryl, hydroxy alkyl, a substituted hydroxyalkyl, an alkyl carboxylic acid derivative, an alkenyl carboxylic acid derivative, a nucleic acid interactive compound, a phosphine oxide, or a sulfoxide; $R^2$ is $R^1$, alkyl, aryl, phenyl, aryl, aryl($C_1$–$C_4$), a heterocycle substituent and may be connected via one or more carbon or heteroatom bonds to another $R^2$; L is a linking group molecule, where L is a bond, an alkyl, alkenyl, alkynyl, cycloalkyl, alkyl carbonyl, alkoxy carbonyl, phenyl, aryl, hydroxy alkyl, a substituted hydroxyalkyl, an alkyl carboxylic acid derivative, an alkenyl carboxylic acid derivative, or a heteroatom or heterocycle substituent In an embodiment, the oligomeric aza-derivative has the structure:

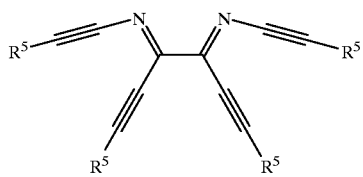

where L is a bond and $R^5$ is as described previously for a substituted-ethynyl group.

In another embodiment, the oligomeric aza-derivative has the structure:

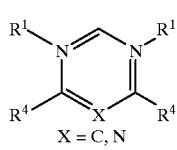

where $R^1$ and $R^4$ are as described previously, L is a nitrogen or a carbon, and $R^2$ of one aza molecule is linked to $R^2$ of the other such that a heterocyclic ring results.

In another embodiment, an oligomeric aza-derivative has the structure:

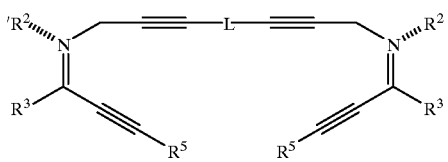

where each instance of $R^2$, $R^3$, and $R^5$ is as previously described, and L is a linking group molecule, where L is a single bond, an alkyl, alkenyl, alkynyl, cycloalkyl, alkyl carbonyl, alkoxy carbonyl, phenyl, aryl, alkyl ($C_1$–$C_4$) aryl, hydroxy alkyl, a substituted hydroxyalkyl, an alkyl carboxylic acid derivative, an alkenyl carboxylic acid derivative, or a heteroatom or heterocycle substituent.

In another embodiment an oligomeric aza-derivative has the structure:

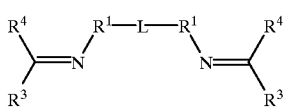

Where each instance of $R^1$ is independently a substituted-propargyl or substituted-allenyl connected to $R^1$ of the second molecule through the substituent $R^5$ of the substituted-propargyl or substituted-allenyl group; each instance of $R^4$ is independently a substituted-ethynyl, substituted-allenyl, or substituted-ethynyl; and each instance of $R^3$ is independently a phenyl, aryl, a heterocycle substituent, $CR^{10}$ or $NR^{14}$; $R^{10}$ and $R^{14}$ are as previously defined.

In an embodiment the dimeric aza-derivative has the structure:

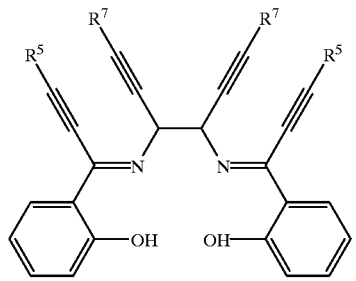

where a substituted-propargyl of an aza-derivative is connected to a substituted propargyl of the second aza-derivative via a bond (where $R^5$ of one substituted-propargyl group is a bond connecting to the second substituted-propargyl group). The aza-derivative is also substituted with a substituted ethynyl group and a phenol.

Where clinical application of these aza-derivatives is undertaken, it may be necessary to prepare the complex as a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Aqueous compositions of the present invention include an effective amount of the aza-derivative, further dispersed in pharmaceutically acceptable carrier or aqueous medium. Such compositions also are referred to as inocula. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also may be incorporated into the compositions.

Solutions of therapeutic compositions may be prepared in water suitably mixed with a surfactant (e.g., hydroxypropylcellulose). Dispersions also may be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for treatment of skin cancers, to prevent chemotherapy-induced alopecia or other dermal hyperproliferative disorder. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance. For the instant application, it is envisioned that the amount of therapeutic composition comprising a unit dose will range from about 5–30 mg of the aza-derivative.

The compounds claimed may be synthesized by one or more general routes. In one embodiment, the appropriate ketone or aldehyde ($R^3COR^4$) is condensed with an amine ($R^1NQ$) in which $R^4$ and $R^3$ are as defined above, or groups that are capable of being transformed into those groups and Q is either hydrogen, a silicon containing group, a tin containing group, or a metal and its associated ligands. The resulting imine may be reacted with an electrophilic compound $R^2X$ where $R^2$ is as defined above, or a group that is convertible to that group, and X is a leaving group.

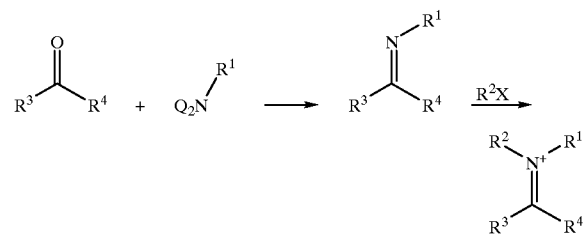

In another embodiment, the compounds may be prepared directly by condensing an appropriate aldehyde or ketone ($R^3COR^4$) with an amine ($R^2NQR^1$), where $R^1$, $R^2$, $R^3$ and $R^4$ are as described above, or are groups capable of being converted to those groups, and Q is hydrogen, a silicon containing group, or a metal.

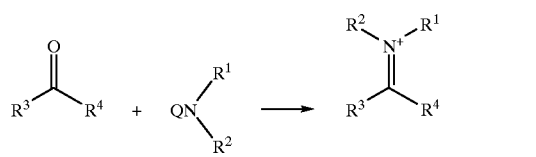

In another embodiment, the compounds may be prepared directly by condensing the appropriate ketone or aldehyde ($R^3COR^4$) with an amine ($R^2NQ$) in which $R^1$, $R^2$, $R^3$, and $R^4$ are as defined above, or are groups that are capable of being transformed into those groups and Q is either hydrogen, a silicon containing group, a tin containing group, or a metal and its associated ligands. The resulting imine may be reacted with an electrophilic compound $R^1X$ where $R^1$ is as defined above, or a group that is convertible to that group, and X is a leaving group.

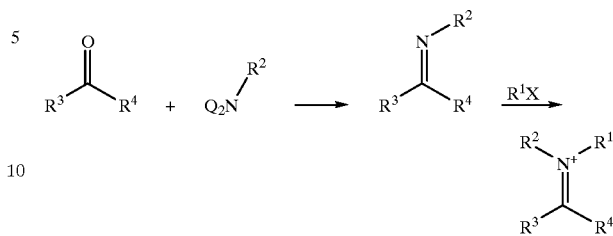

In another embodiment, the compounds may be prepared from the appropriate amide, thioamide, or amidine ($R^4CYNQR^2$) in which $R^4$ and $R^2$ are as described above, or are groups capable of be converted to those groups, Y is oxygen, sulfur, or a (substituted)nitrogen, Q is a hydrogen, a silicon containing group, a tin containing group, or a metal and its associated ligands, and an electrophilic species $R^{3'}X$ where $R^{3'}$ when attached to Y to form $R^{3'}Y$— is equal to $R^3$ or is a group capable of being converted to $R^3$, and X is a leaving group. The resulting imine may be reacted with an electrophilic compound $R^1X$ where $R^1$ is as defined above, or a group that is convertible to that group, and X is a leaving group.

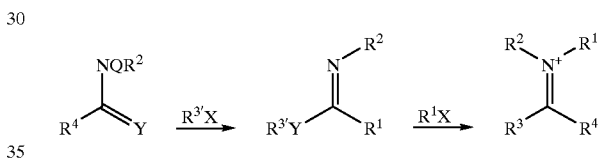

In another embodiment, the compounds may be prepared from the appropriate amide, thioamide, or amidine ($R^4CYNQR^1$) in which $R^1$ and $R^4$ are as described above, or are groups capable of being converted into $R^1$ or $R^4$; Y is oxygen, sulfur, or a (substituted)nitrogen, Q is a hydrogen, a silicon containing group, a tin containing group , or a metal and its associated ligands, and an electrophilic species $R^{3'}X$ where $R^{3'}$ when attached to Y to form $R^{3'}Y$—is equal to $R^3$ or is a group capable of being converted to $R^3$, and X is a leaving group. The resulting imine may be reacted with an electrophilic compound $R^2X$ where $R^2$ is as defined above, or a group that is convertible to that group, and X is a leaving group.

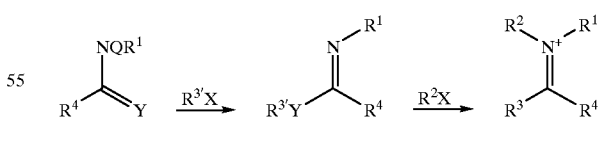

In another embodiment, the compounds may be prepared from the appropriate amide, thioamide, or amidine ($R^4CYNR^1R^2$) in which $R^1$, $R^2$, and $R^4$ are as described above, or are groups capable of being converted into those groups; Y is oxygen, sulfur, or a (substituted)nitrogen, and an electrophilic species $R^{3'}X$ where $R^{3'}$ when attached to Y to form $R^{3'}Y$—is equal to $R^3$ or is a group capable of being converted to $R^3$, and X is a leaving group.

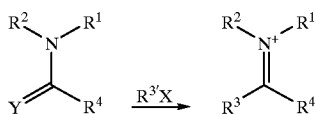

In another embodiment, the compounds may be prepared from the appropriate imine derivative $R^3(C=NX)R^4$ in which $R^4$ and $R^3$ are as described above, or are groups capable of be converted into those groups and X is a leaving group, and a nucleophilic species $R^1M$, in which $R^1$ is as described above or a group capable of being converted to $R^1$ and M is a hydrogen, a tin containing group, a silicon containing group, or a metal and its associated ligands. The resulting imine may be reacted with an electrophilic compound $R^2X$ where $R^1$ is as defined above, or a group that is convertible to that group, and X is a leaving group.

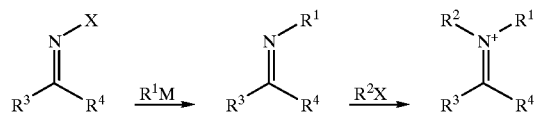

In another embodiment, the compounds may be prepared from the appropriate imine derivative $R^3(C=NX)R^4$ in which $R^4$ and $R^3$ are as described above, or are groups capable of be converted into those groups and X is a leaving group, and a nucleophilic species $R^2M$, in which $R^2$ is as described above or a group capable of being converted to $R^2$, and M is a hydrogen, a tin containing group, a silicon containing group, or a metal and its associated ligands. The resulting imine may be reacted with an electrophilic compound $R^1X$ where $R^1$ is as defined above, or a group that is convertible to that group, and X is a leaving group.

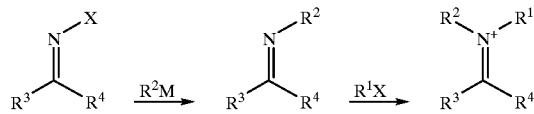

In another embodiment, the compounds may be prepared form the appropriate imine derivative $R^3(C=NR^1)X$ in which $R^1$ and $R^3$ are as described above, or are groups capable of be converted into those groups and X is a leaving group, and a nucleophilic species $R^4M$, in which $R^4$ is as described above or a group capable of being converted to $R^4$, and M is a hydrogen, a tin containing group, a silicon containing group, or a metal and its associated ligands. The resulting imine may be reacted with an electrophilic compound $R^2X$ where $R^2$ is as defined above, or a group that is convertible to that group, and X is a leaving group.

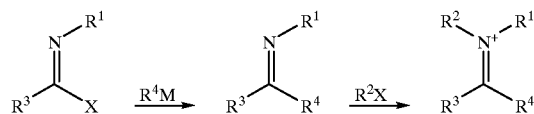

In another embodiment, the compounds may be prepared from the appropriate imine derivative $R^4(C=NR^1)X$ in which $R^1$ and $R^4$ are as described above, or are groups capable of being converted into those groups; X is a leaving group; $R^3M$ is a nucleophilic species, in which $R^3$ is as described above or a group capable of being converted to $R^3$, and M is a hydrogen, a tin containing group, a silicon containing group, or a metal and its associated ligands. The resulting imine may be reacted with an electrophilic compound $R^2X$ where $R^2$ is as defined above, or a group that is convertible to that group, and X is a leaving group.

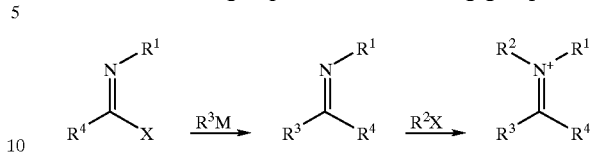

In another embodiment, the compounds may be prepared from the appropriate imine derivative $R^4(C=NR^2)X$ in which $R^4$ and $R^2$ are as described above, or are groups capable of being converted into those groups, and X is a leaving group, and a nucleophilic species $R^3M$, in which $R^3$ is as described above or a group capable of being converted to $R^3$, and M is a hydrogen, a tin containing group, a silicon containing group, or a metal and its associated ligands. The resulting imine may be reacted with an electrophilic compound $R^1X$ where $R^1$ is as defined above, or a group that is convertible to that group, and X is a leaving group.

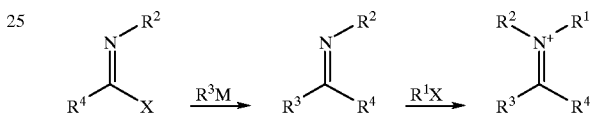

In another embodiment, the compounds may be prepared from the appropriate imine derivative $R^3(C=NR^2)X$ in which $R^2$ and $R^3$ are as described above and may combine to form a heterocyclic ring; X is a leaving group; $R^4M$ is a nucleophilic species, in which $R^4$ is as described above or a group capable of being converted to $R^4$, and M is a hydrogen, a tin containing group, a silicon containing group, or a metal and its associated ligands. The resulting imine may be reacted with an electrophilic compound $R^1X$ where $R^1$ is as defined above, or a group that is convertible to that group, and X is a leaving group.

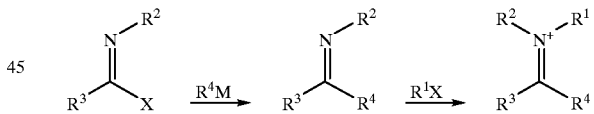

In another embodiment the aza-derivatives have the structure (A) or (B) in which either one of the groups $R^1$ and $R^4$ (but not both) consist of a group (defined as R for this embodiment) that can be converted to a substituted ethynyl group, a substituted allenyl group or a substituted propargyl group In a preferred embodiment the compounds (which may be generated by this method) have the following structures:

an azole

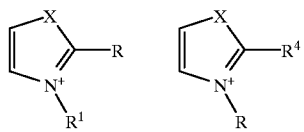

X = N, O, or S    X = N, O, or S a pyridine

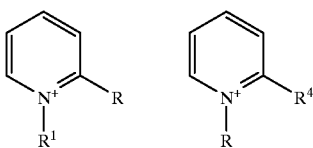

where $R^1$ and $R^4$ are substituted-ethynyl, substituted-allenyl, or substituted-propargyl groups as defined previously, and R is a halogen, sulfonate ester, alkyl, alkenyl, or a group capable of being converted into $R^1$ or $R^4$ as defined above.

In another preferred embodiment, the groups which may be converted into a substituted-ethynyl, substituted-allenyl, or substituted-propargyl have the following structures:

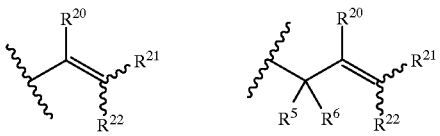

where $R^5$ and $R^6$ are as previously defined, $R^{20}$ $R^{21}$, and $R^{22}$ are independently a hydrogen, a halogen, a carboxylic acid derivative, a sulfonate ester derivative, a phosphoester derivative, or an alcohol.

In general, all of the above described compounds may be non-hydrolyzable, cationic compounds that bind to nucleic acids. They may also undergo a series of chemical reactions in the presence of nucleic acids to generate reactive intermediates that cleave the DNA. They may be converted in vivo into compounds capable of generating reactive intermediates capable of cleaving DNA. These compounds may selectively localize to cancer cells due to their lipophilic and cationic nature. Thus the compounds may be cancer selective cytotoxic agents. These compounds may be separately optimized such that each compound has a unique spectrum of activity against various tumor types.

These compounds may be used in the treatment of a number of disease states. In addition to treatment of cancer and other proliferative diseases, these compounds may have uses in other disease states, such as viral and bacterial infections. In addition, these compounds may be fluorescent dyes, and by virtue of the diradical chemistry that they enter into, they may have utility in the manufacture of dye-fast fluorescent materials such as plastics and as biochemical probes for such techniques as FISH and flow cytometry. Also by virtue of the diradical intermediates that these compounds produce under very mild conditions, they may find utility as initiators of radical reactions, including polymerization reactions.

This class of compounds possesses a number of features that make them easily modified in order that efficacy may be maximized and undesirable effects minimized. For example, the nature of the substituents may be modified so as to retain hydrolytic stability yet change the degree and nature of interaction with DNA and other potential receptors. The rate of formation and the ability of the diradical intermediates to effect DNA cleavage chemistry may also be altered by the proper choice of substituents within aza-derivatives.

The following examples are included to demonstrate embodiments of the invention. Those of skill in the art, in light of the present disclosure, should appreciate that many changes may be made in the specific examples which are disclosed and still obtain a like or similar result without departing from the spirit and scope of the invention.

EXAMPLE 1

Synthesis/testing of C,N-dialkynylimines (3-aza-enediynes) 33a,b

Figure 9:
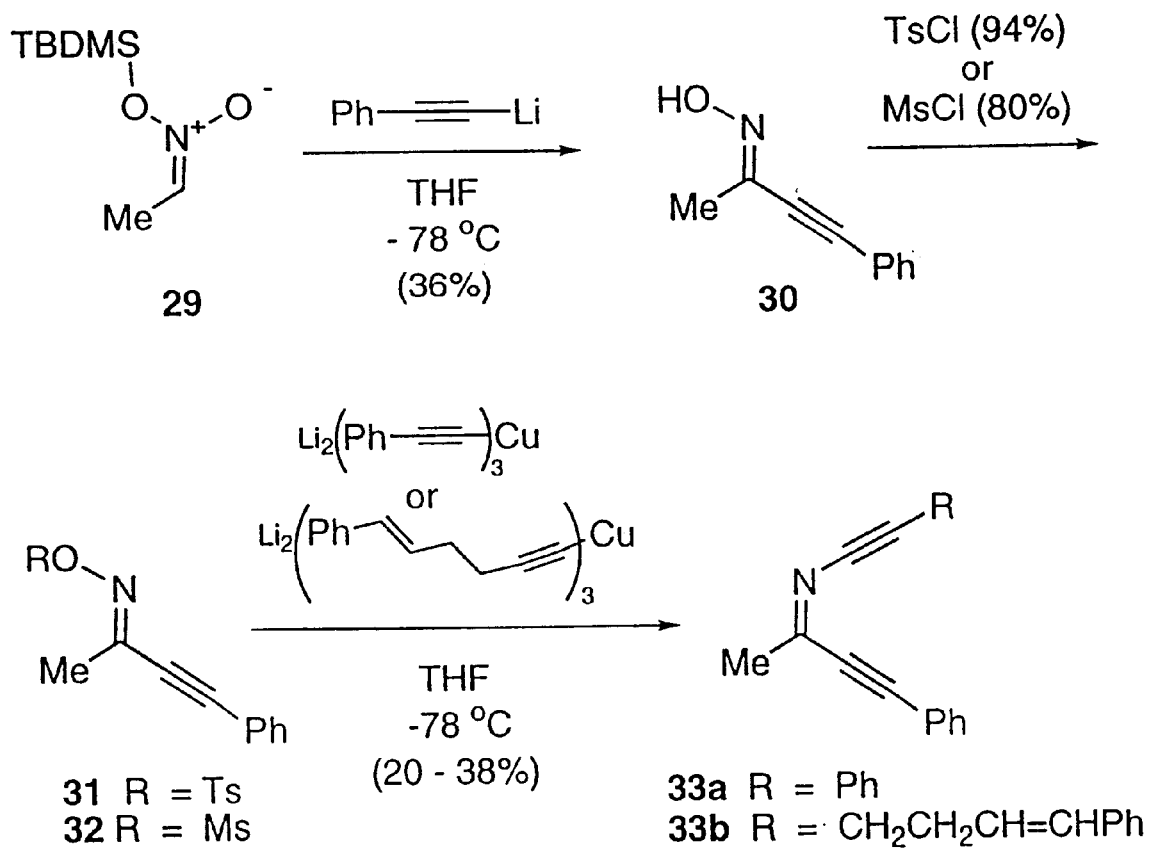
FIG. 9 depicts a synthetic route to C,N-dialkynylimines (3-aza-enediynes).
Figure 10:
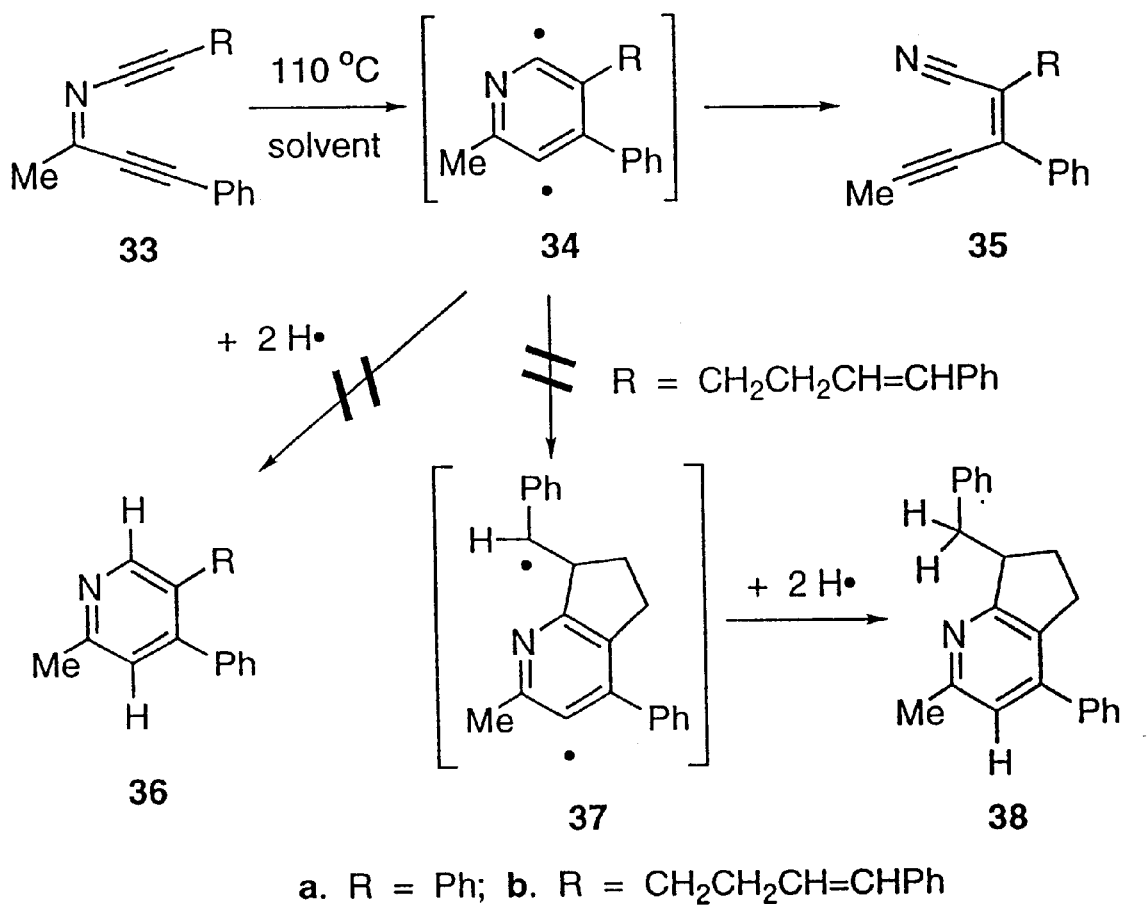
FIG. 10 depicts the reaction of C,N-dialkynylimines.

A general synthetic route to C,N-dialkynylimines (3-aza-enediynes) 33a,b is depicted in FIG. 9. These imines are isolated as air stable yellow oils after chromatography. When a benzene solution of 33a is heated under reflux overnight, nitrile 35a is produced in 88% yield (FIG. 10). The nitrile 35a is isolated as a single stereoisomer, which is assigned the (Z)-geometry by comparison with authentic (E)-35a. Authentic (E)-3a was synthesized by the palladium-catalyzed coupling of 1-propynyltributyltin and the (E)-enol triflate of 2-cyano-2-phenylacetophenone. Heating a solution of imine 33a in benzene containing a large excess of 1,4-cyclohexadiene (1,4-chd) as a hydrogen atom trap, or in neat 1,4-chd at 150° C. for two hours affords the nitrile 35a as the only isolable product. The imine 33b contains a pendent double bond that could serve as an intramolecular trap for the putative diradical intermediate 34 (FIG. 10). We find that heating a benzene solution of 33b containing a large excess of 1,4-chd affords only the nitrile 35b in nearly quantitative yield. In none of these reactions were any products e.g. 36 or 38) which would arise from trapping of the 2,5-ddp intermediate 34 detected.

The $t_{1/2}$ for the thermal isomerization of 33a to 35a is between 40 and 50 min at 110° C., regardless of solvent polarity. The $t_{1/2}$ for the Bergman cyclization of the corresponding (Z)-1,6-diphenylhex-3-ene-1,5-diyne (39) to o-terphenyl is about 1000-fold slower than the rearrangement of 33a to 35a.

EXAMPLE 2

Figure 15A:
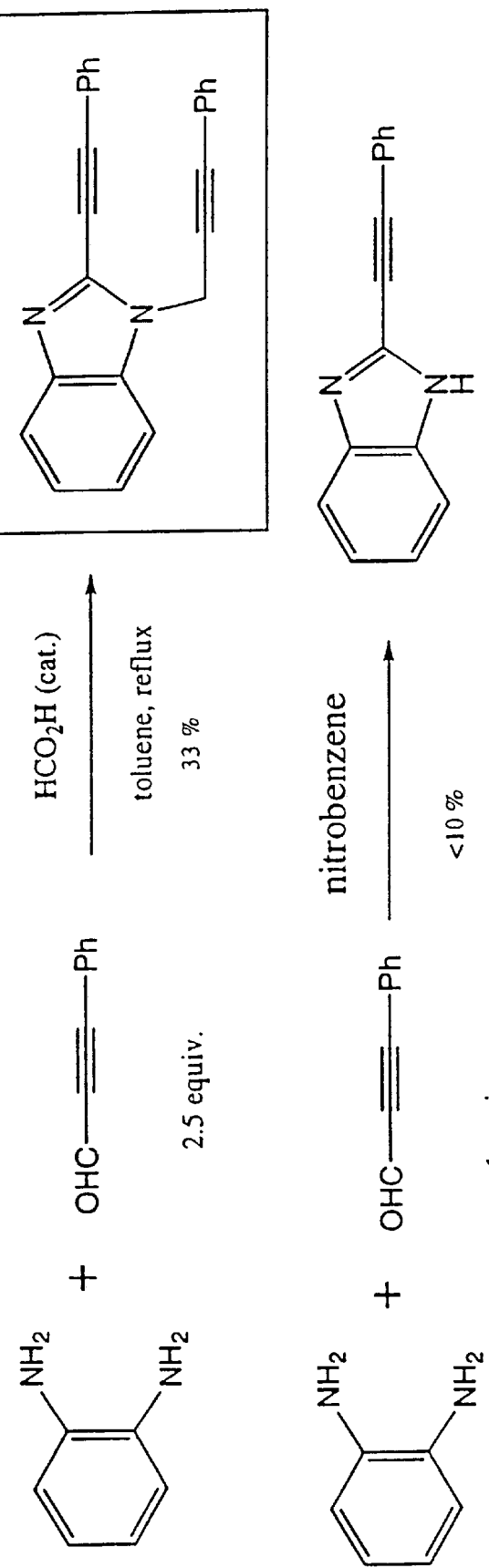
FIGS. 15A, 15B, and 15C depict the synthesis of 2-alkynyl benzimidazoles.
Figure 15B:
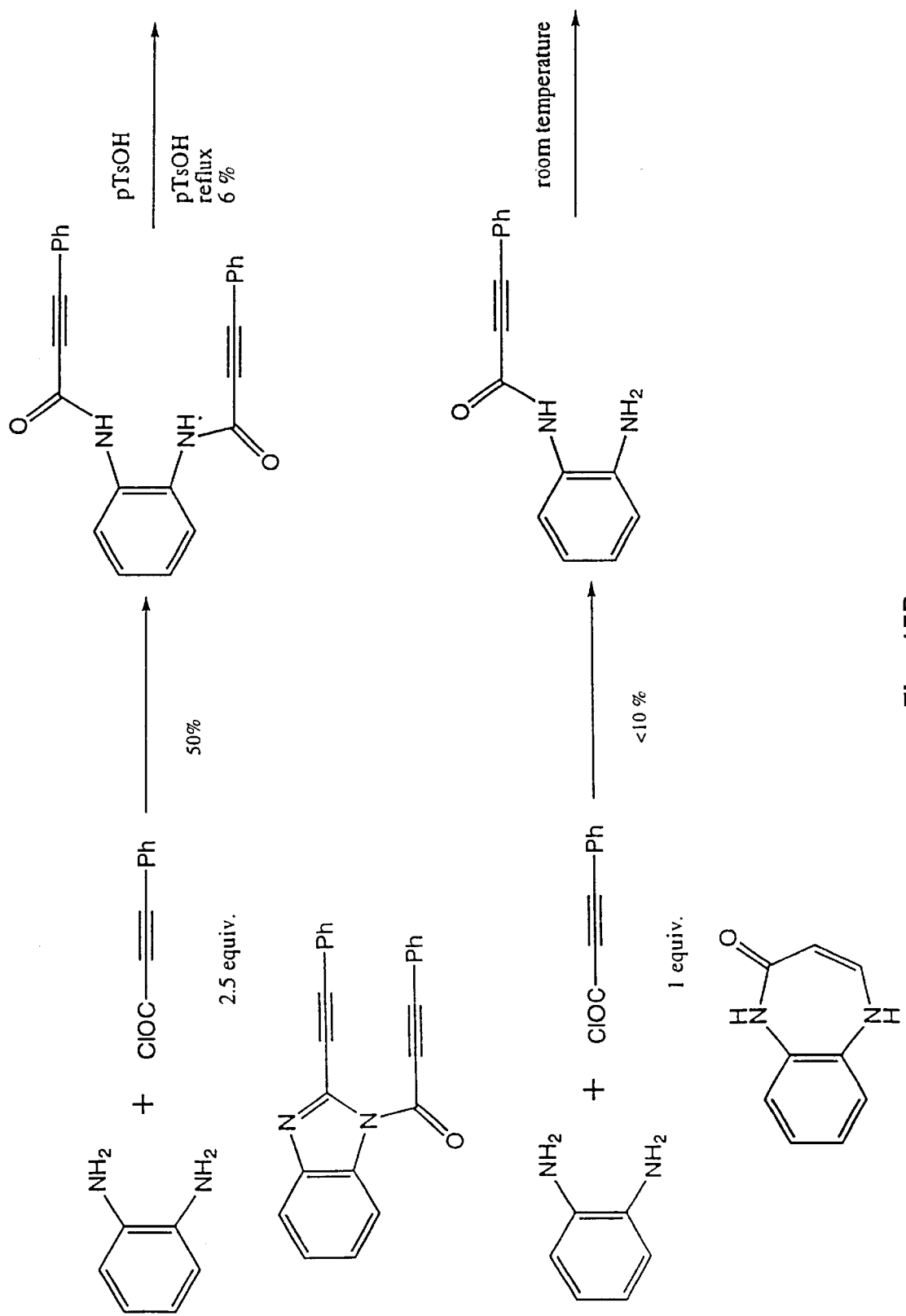
Figure 15C:
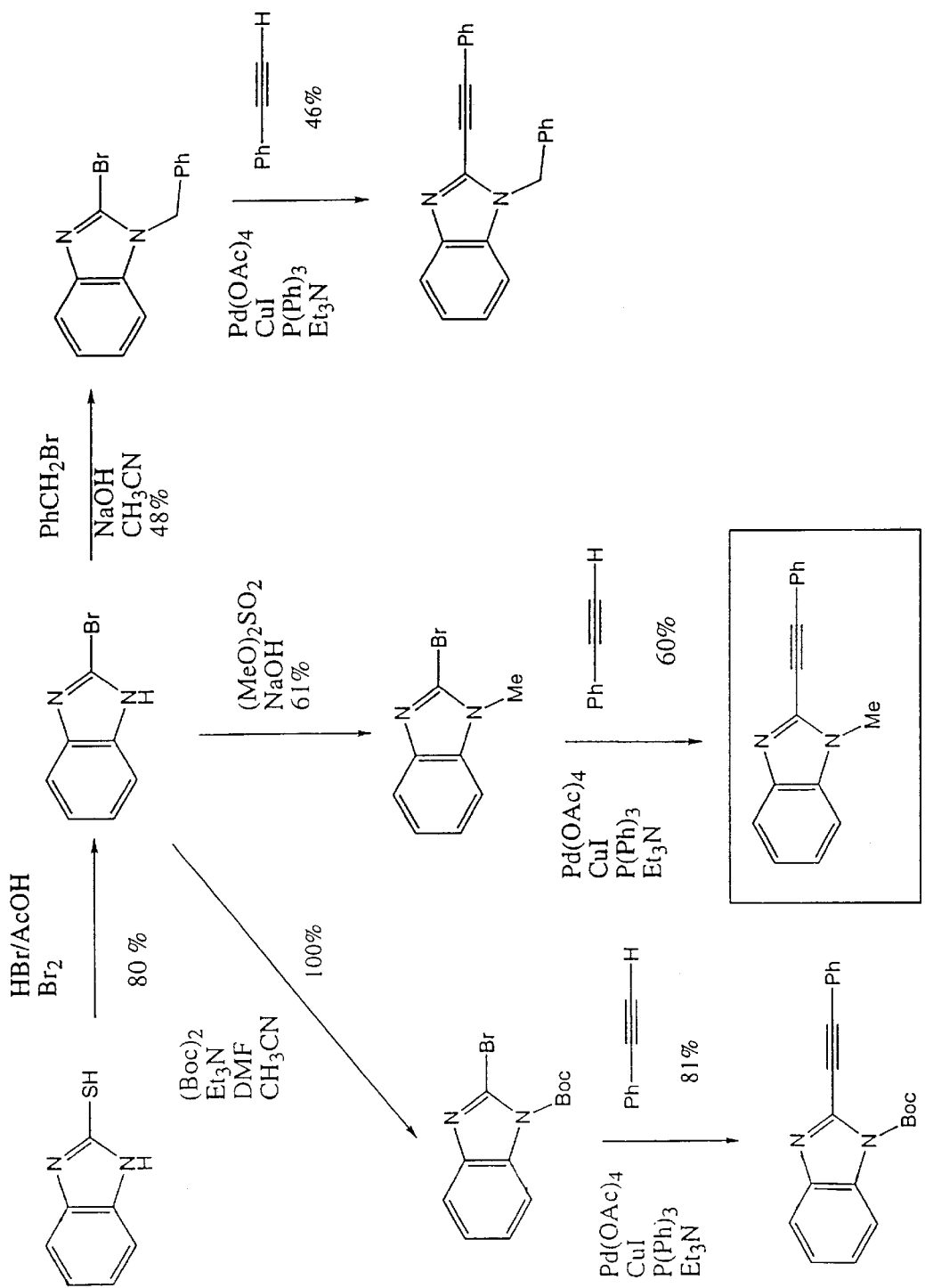
Figure 15D:
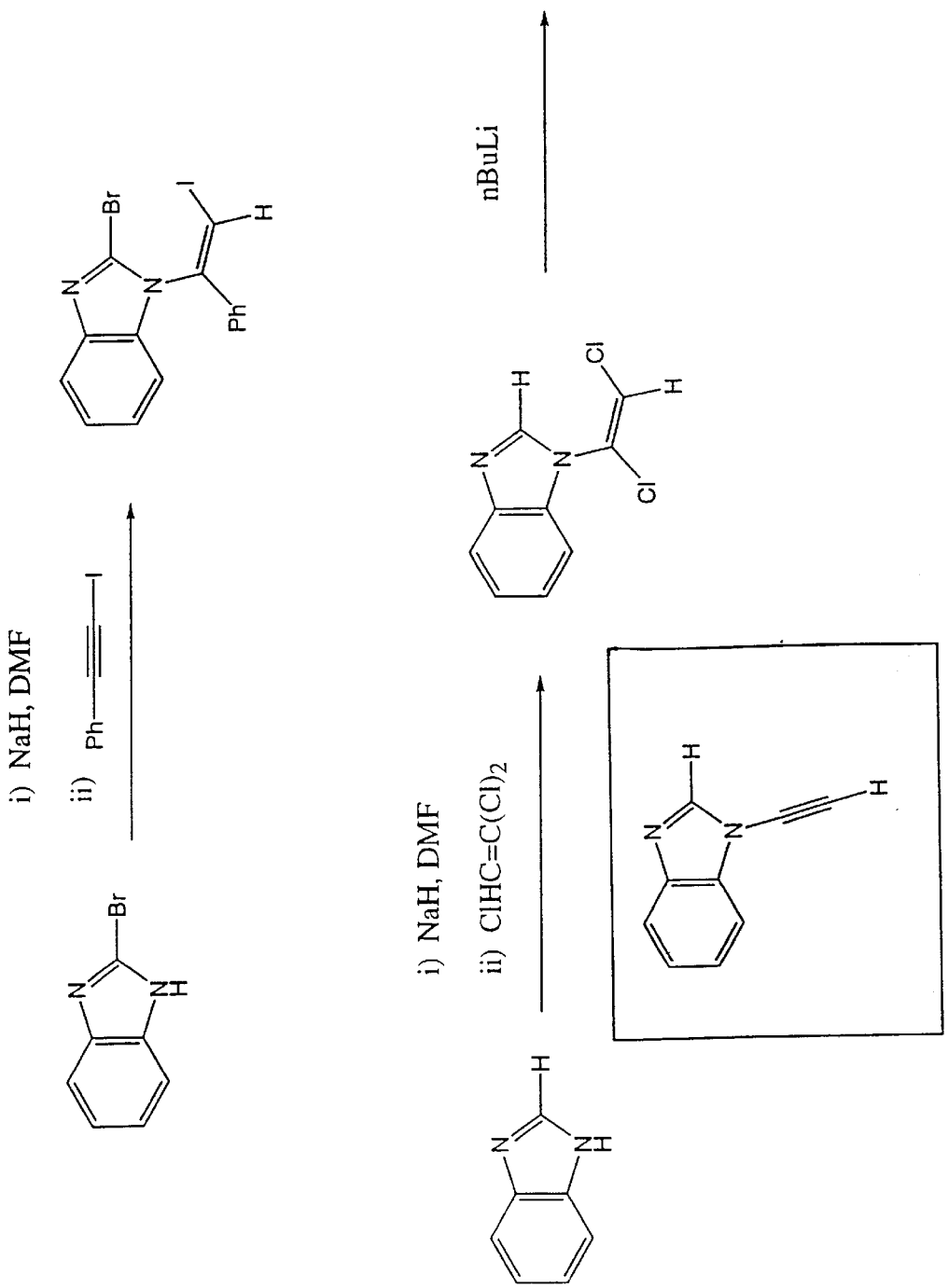
FIG. 15D depicts the synthesis of N-alkynyl benzimidazoles.
Figure 16:
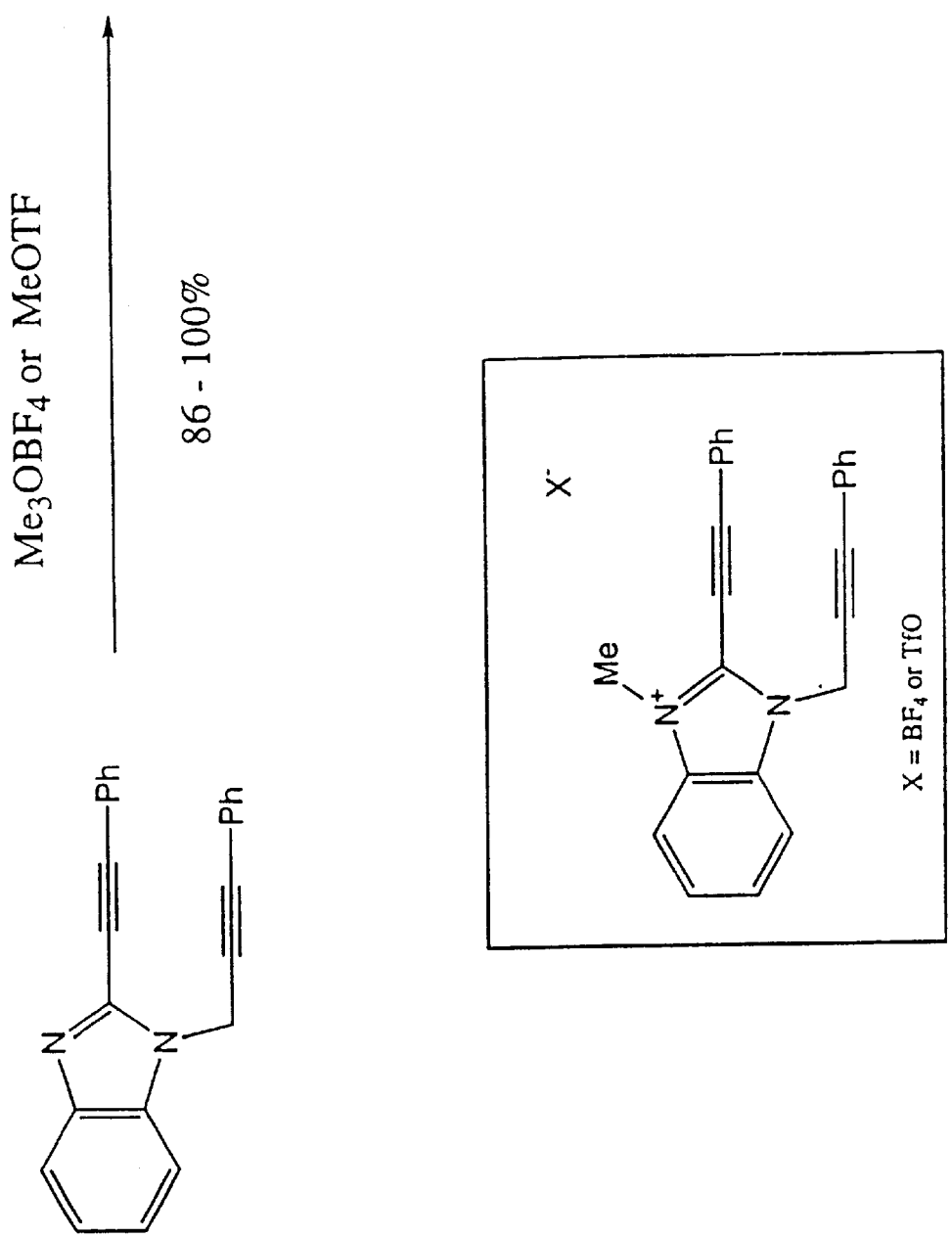
FIG. 16 depicts the synthesis of benzothiozolium salts.
Figure 17:
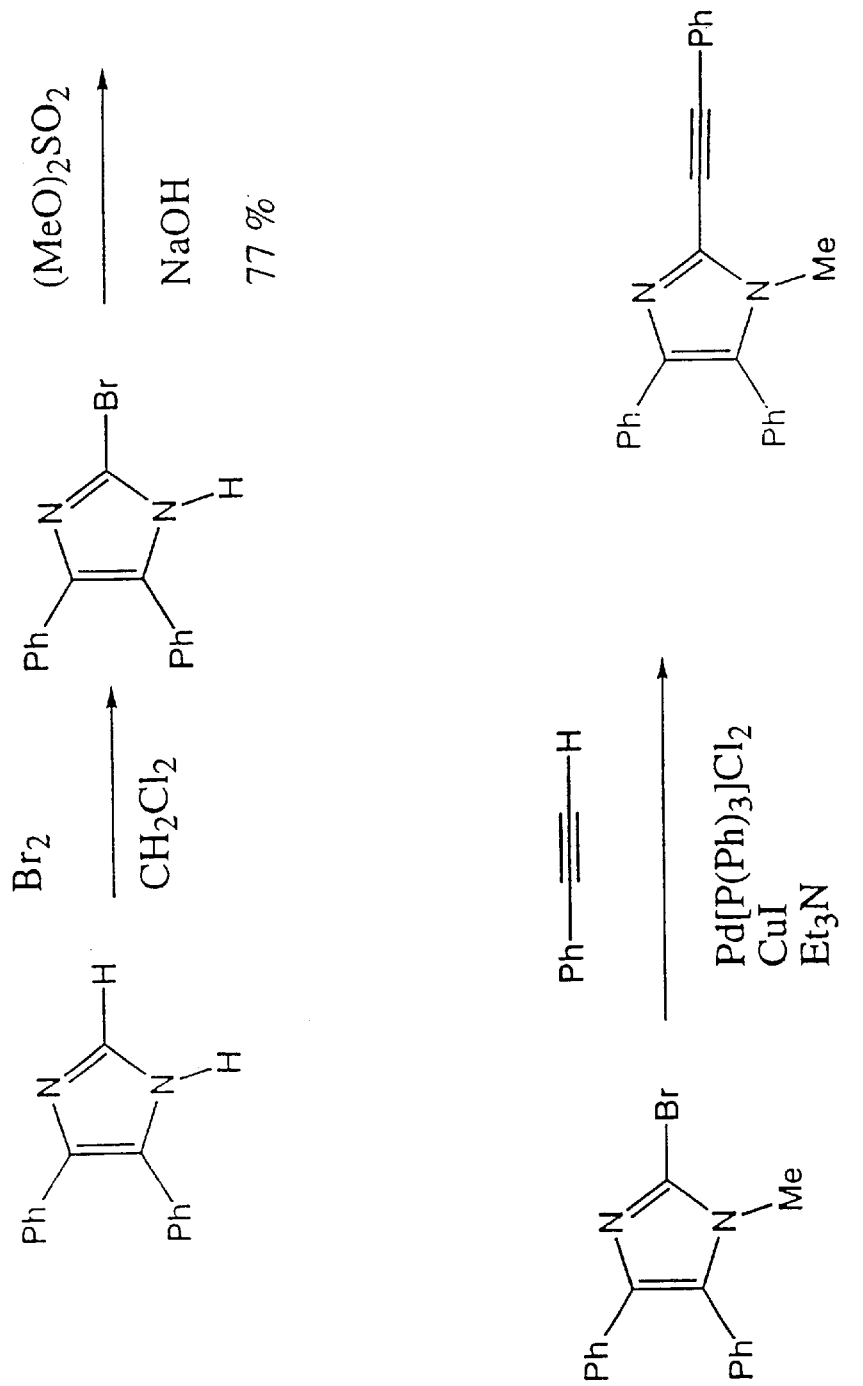
FIG. 17 depicts the synthesis of 2-alkynyl-N-propargyl imidazoles.
Figure 18:
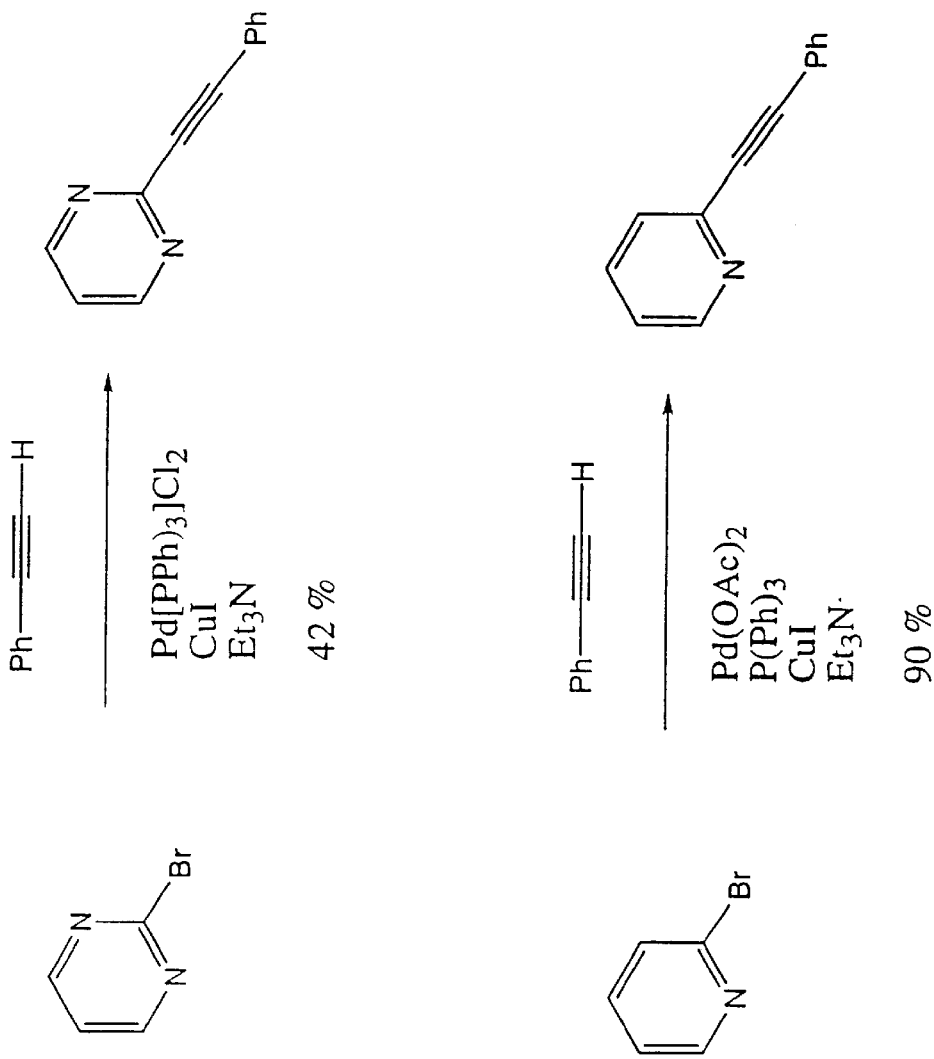
FIG. 18 depicts the synthesis of 2-alkynyl-N-propargyl pyrimidine and pyridine.
Figure 19:
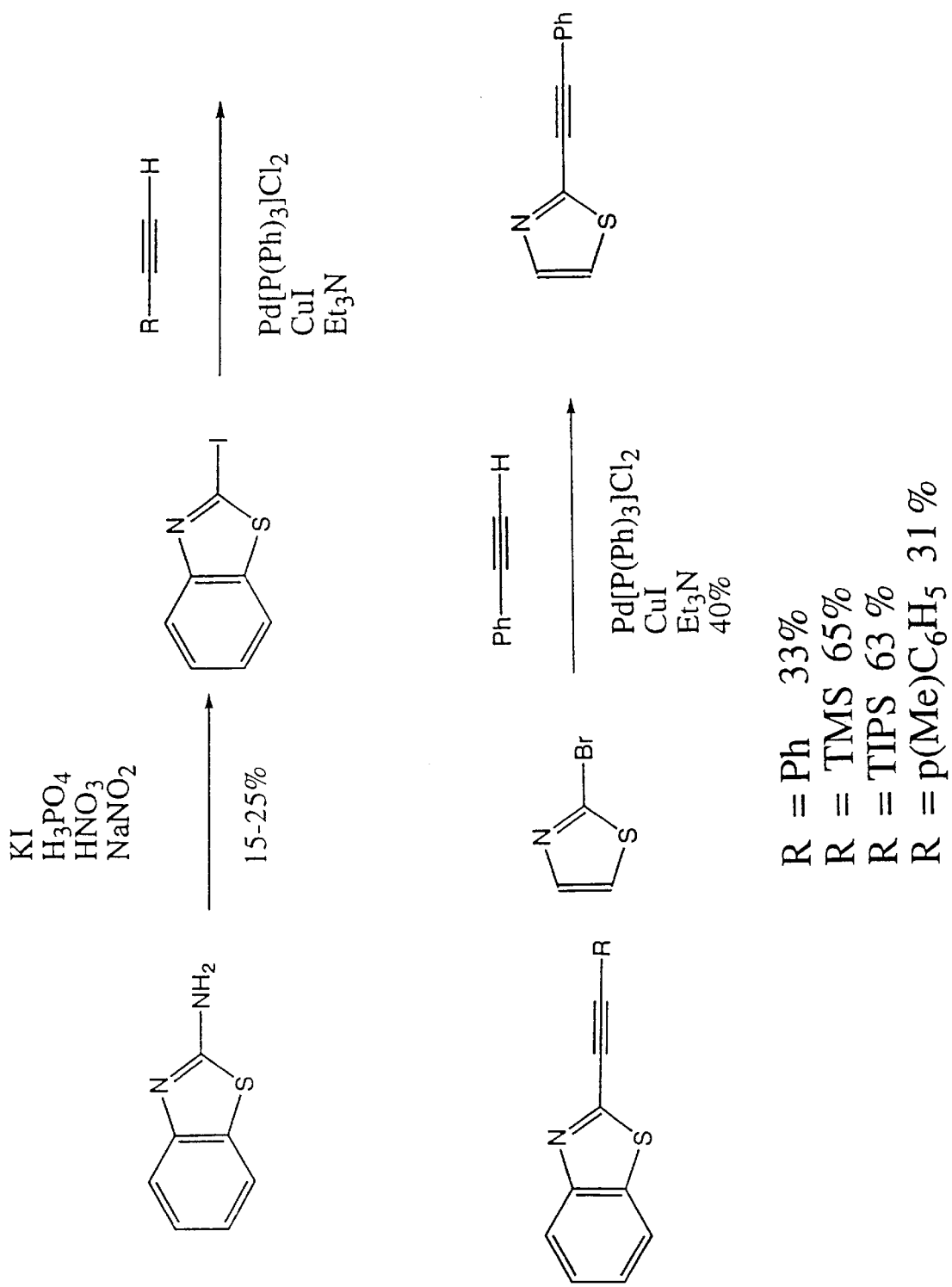
FIG. 19 depicts the synthesis of 2-alkynyl-N-propargyl thiazoles and benzothiazoles.
Figure 20:
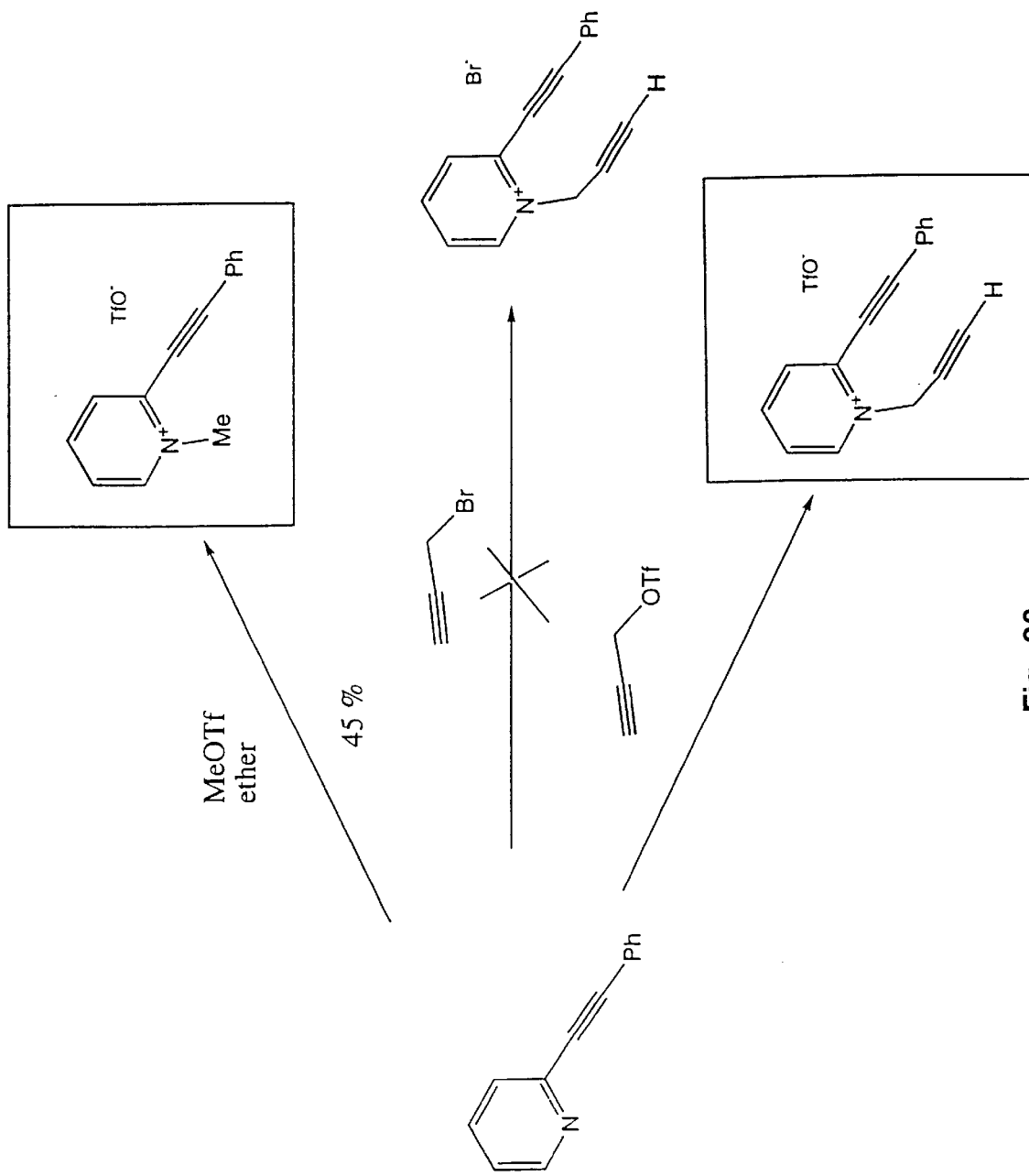
FIG. 20 depicts the reactions of 2-alkynyl-N-propargyl pyridines.
Figure 21A:
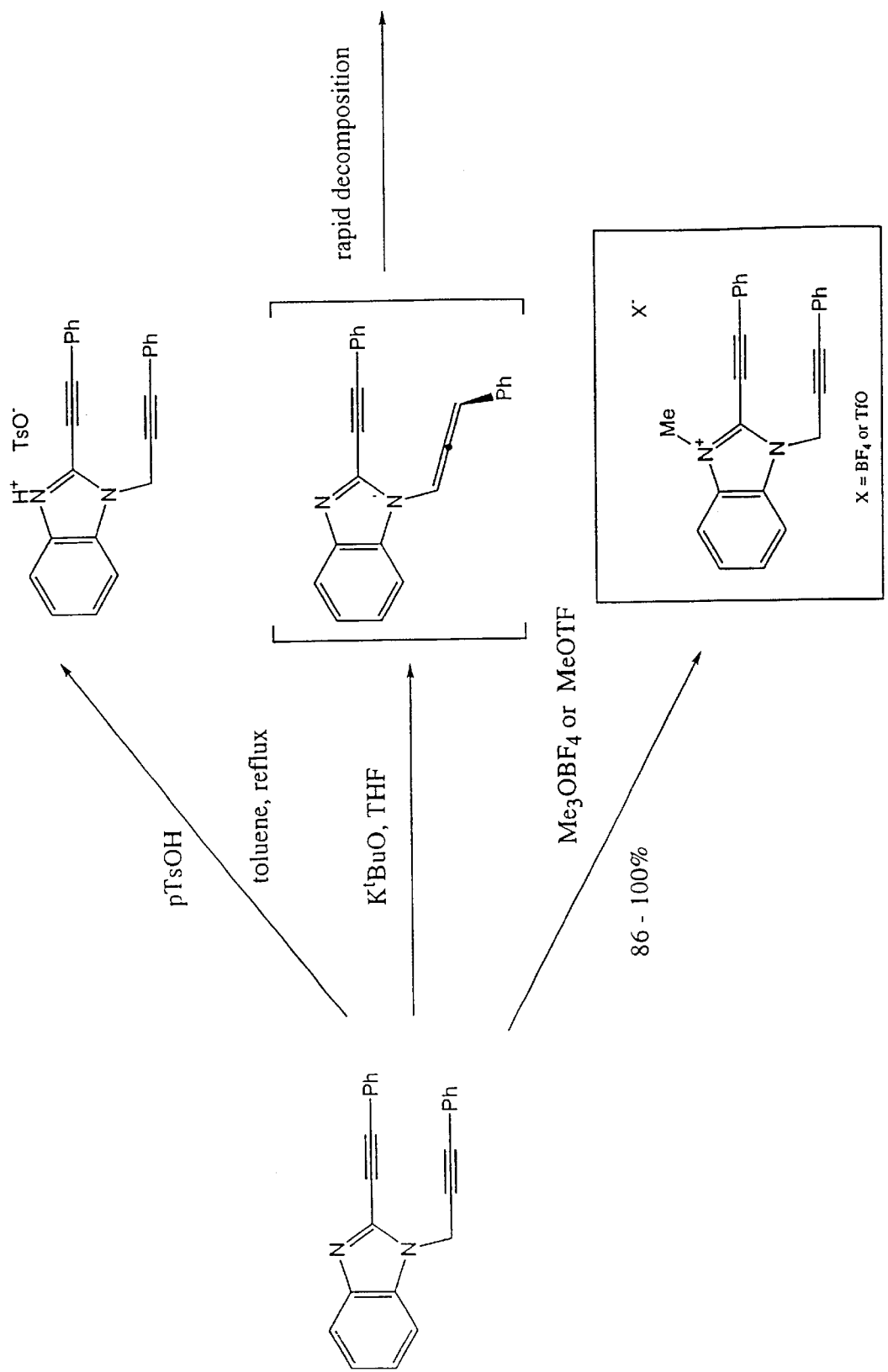
FIGS. 21A–D depict the reactions of N-(phenylpropargyl)-2-(2'-phenylethynyl) benzimidazole.
Figure 21B:
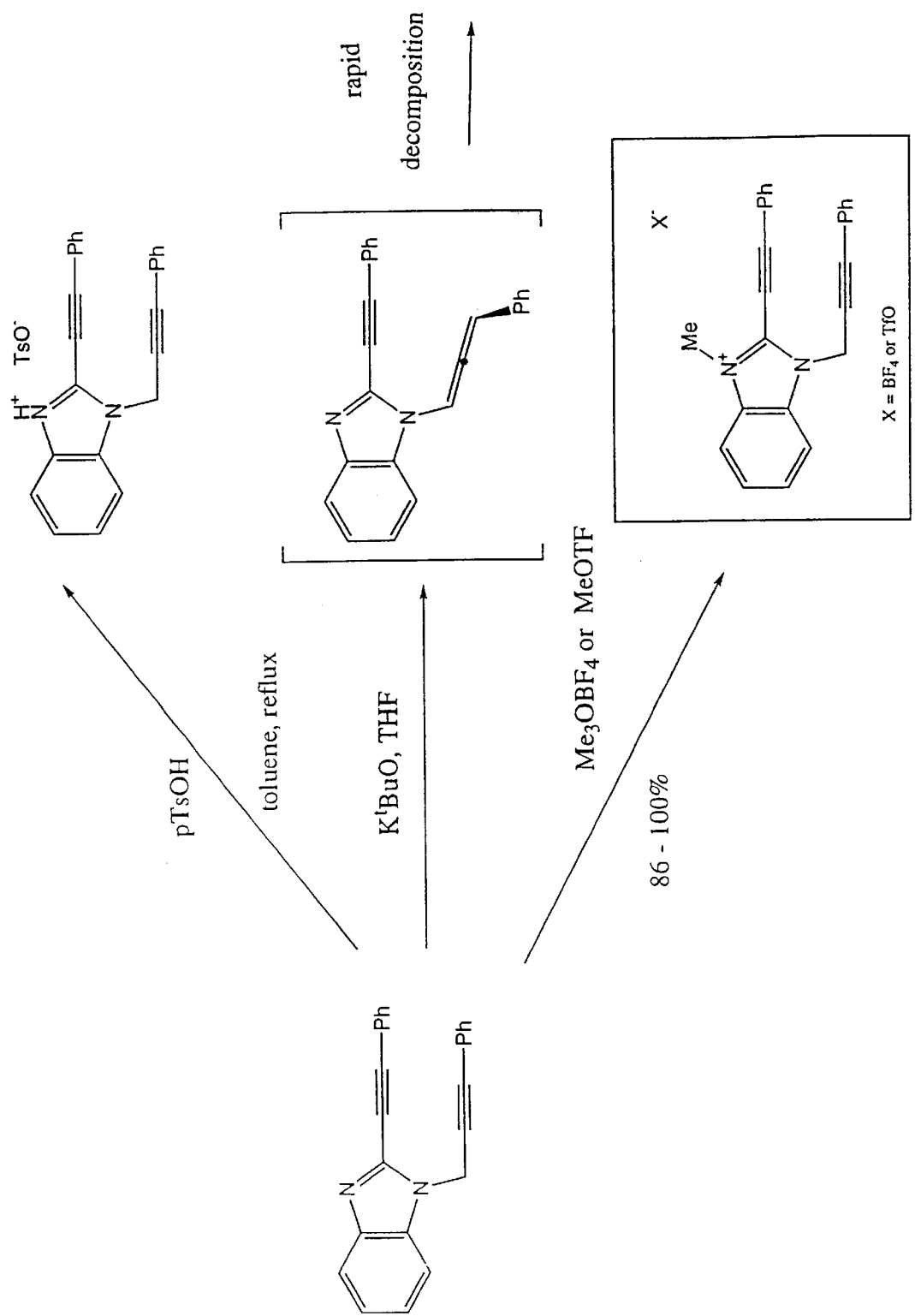
Figure 21C:
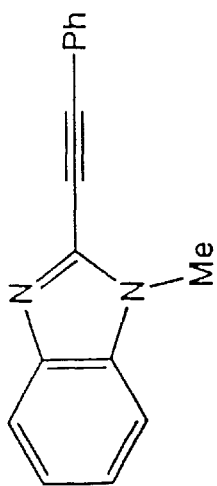
Figure 21C:
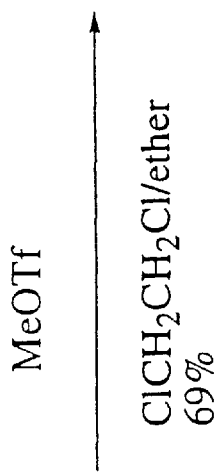
Figure 21C:
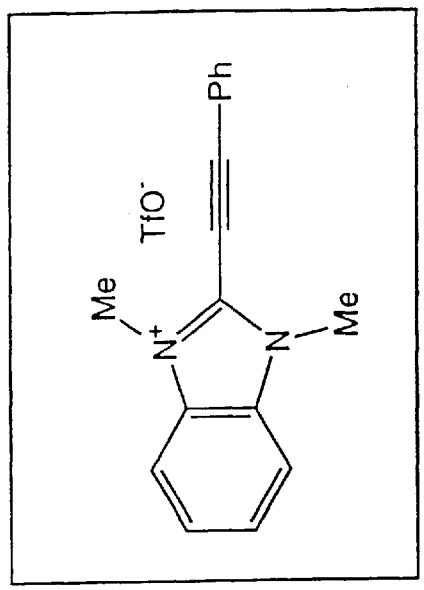
Figure 21D:
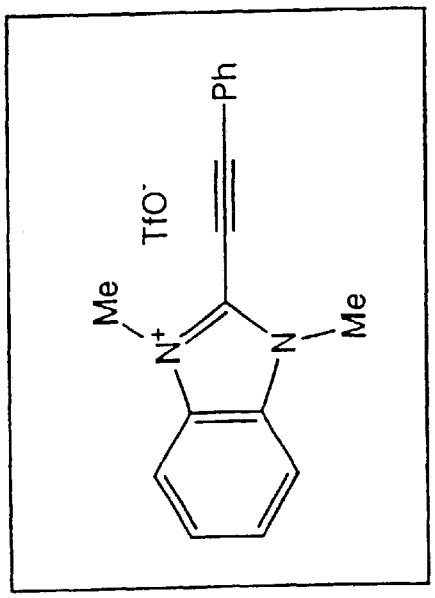
Figure 21D:
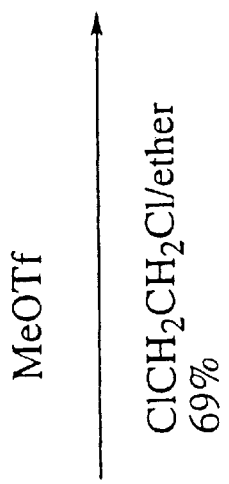
Figure 21D:
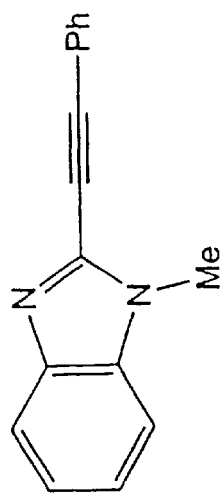
Figure 22:
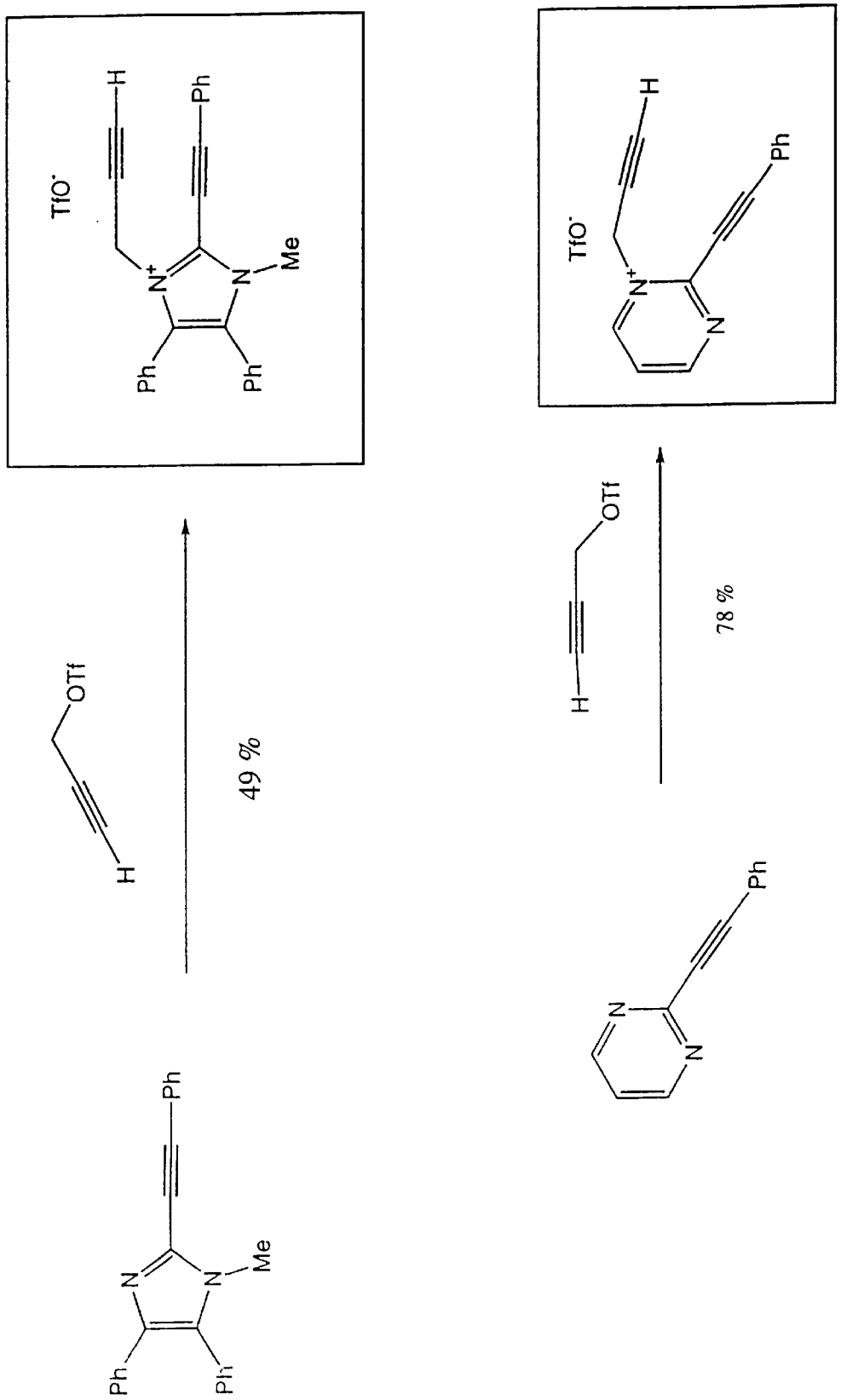
FIG. 22 depicts the reactions of 2-alkynyl-N-propargyl imidazoles and pyridines.
Figure 23:
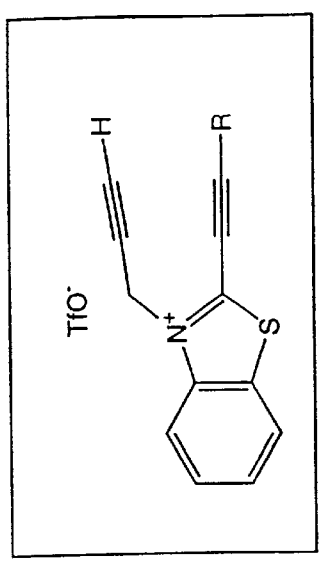
FIG. 23 depicts the reactions of 2-alkynyl-N-propargyl thiazoles and benzothiazoles.
Figure 23:
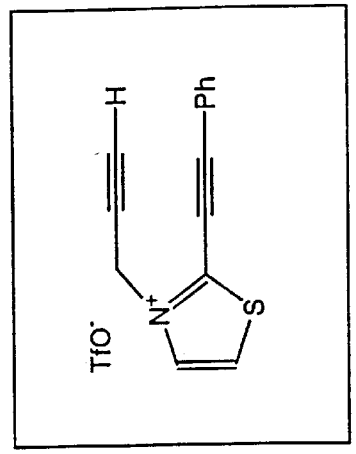
Figure 23:
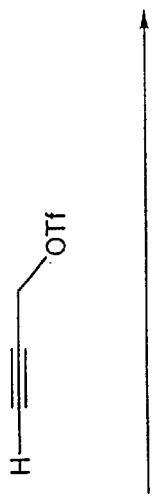
Figure 23:
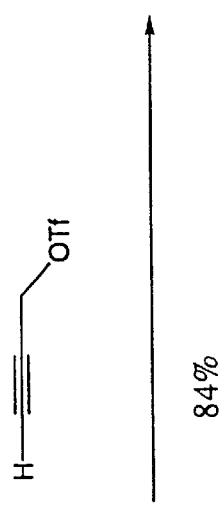
Figure 23:
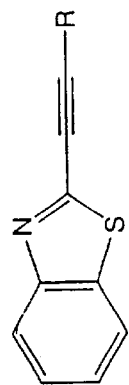
Figure 23:
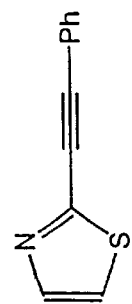

Synthesis of thiazolium and benzothiazolium analogues containing an 4-aza-3-ene-1,6-diyne moiety and their salts A general synthetic scheme employing reaction of 2-halo substituted heterocycles with the appropriate acetylenes in the presence of palladium catalyst affords 2-alkynyl substituted heterocycles. (FIGS. 15A/15B/15C/15D–19). These heterocycles can be alkylated by treatment with methyl or propargyl triflate, affording the desired azaenediene heterocycles; i.e., thiazolium benzothiazolium, pyridinium and imidazolium compounds. (FIGS. 20–23)

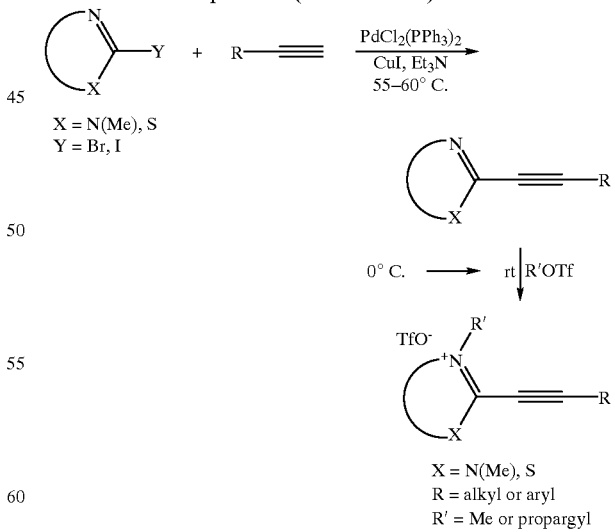

Table 1 shows the synthesis of representative 2-alkynyl heterocycles and the percentage yield obtained. Table 2 shows the synthesis of salts of these 2-alkynyl heterocycles and the percentage yield obtained.

TABLE 1
SYNTHESIS OF 2-ALKYNYL HETEROCYCLES
| 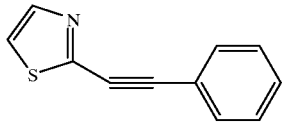 | ≡—R | Yield (%) | Product |
|---|---|---|---|
| 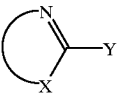 | R = C$_6$H$_5$ | 42 | 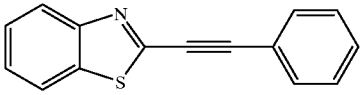 |
| 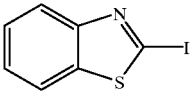 | R = C$_6$H$_5$ | 41 | 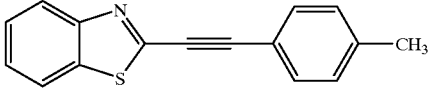 |
|  | R = 4-CH$_3$-C$_6$H$_4$ | 30 | 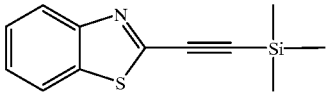 |
|  | R = (CH$_3$)$_3$Si | 65 | 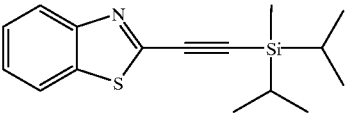 |
|  | R = [CH(CH$_3$)$_2$]Si | 63 | 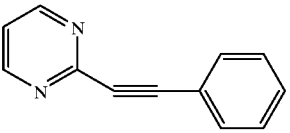 |
| 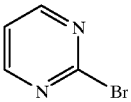 | R = C$_6$H$_5$ | 42 | 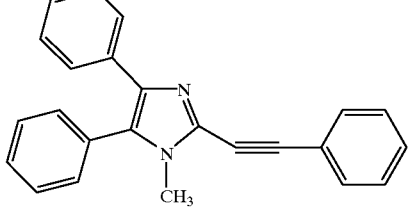 |
| 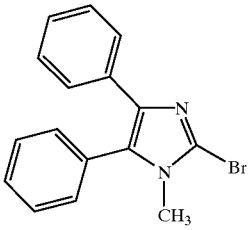 | R = C$_6$H$_5$ | 51 |  |

TABLE 2

SYNTHESIS OF 2-ALKYNYL HETEROCYCLIC SALTS

| Starting Material | R-OTf | Yield (%) | Structure |
|---|---|---|---|
| thiazole-C≡C-Ph | R = CH$_3$ | 82 | N-methyl thiazolium-C≡C-Ph, TfO$^-$ |
| | R = Propargyl | 84 | N-propargyl thiazolium-C≡C-Ph, TfO$^-$ |
| N-propargyl benzothiazolium-C≡C-C$_6$H$_4$-CH$_3$, TfO$^-$ | R = CH$_3$ | 74 | N-methyl benzothiazolium-C≡C-Ph, TfO$^-$ |
| | R = Propargyl | 65 | N-propargyl benzothiazolium-C≡C-Ph, TfO$^-$ |
| | R = Propargyl | 86 | N-propargyl benzothiazolium-C≡C-C$_6$H$_4$-CH$_3$, TfO$^-$ |
| | R = Propargyl | 42 | N-propargyl benzothiazolium-C≡C-TMS, TfO$^-$ |
| | R = Propargyl | 20 | N-propargyl benzothiazolium-C≡C-TIPS, TfO$^-$ |
| pyrimidine-C≡C-Ph | R = Propargyl | 78 | N-propargyl pyrimidinium-C≡C-Ph, TfO$^-$ |

TABLE 2-continued

SYNTHESIS OF 2-ALKYNYL HETEROCYCLIC SALTS

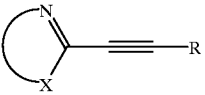

| R-OTf | Yield (%) | Structure |
|---|---|---|
| R = Propargyl | 49 | 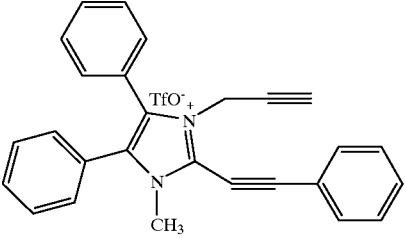 |

Some of these heterocyclic salts are unstable in nucleophilic solvents like methanol, however. The stability of solutions of these salts in CD$_3$OD can be monitored by NMR. (TABLE 3) Salts bearing a sterically large group on the 2-position alkyne substituent are relatively stable, whereas those bearing sterically unencumbered groups undergo reaction within minutes. The methanol addition product shown below was isolated and the structure confirmed. This enol ether is produced quantitatively as the stereoisomer indicated and was determined by nOe experiments.

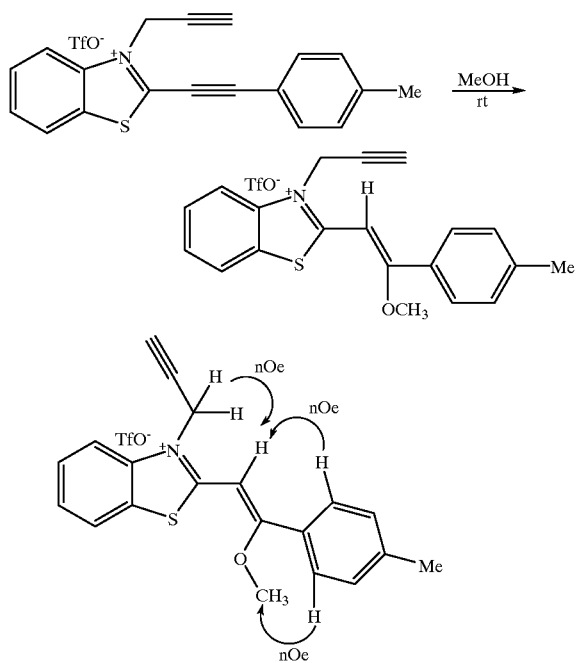

EXAMPLE 3

Design of and DNA Cleavage by Heterocyclic Variants

Simple acyclic aza-enediynes undergo a thermal interconversion that is analogous to the Bergman rearrangement of enediynes. Enediynes are shown to be core constituents of several potent antitumor natural products that are capable of generating diradical intermediates. Aza-enediynes have several advantages over natural enediynes; they undergo conversion under milder conditions and may be less toxic than their natural counterparts. The heterocyclic substitution may allow for modulation of reactivity; the reversible ylide formation provides further hydrolytic stability due to delocalization and may allow conversion into active diradical-generating forms by inhibiting retro-aza-Bergman reactions.

Figure 24:
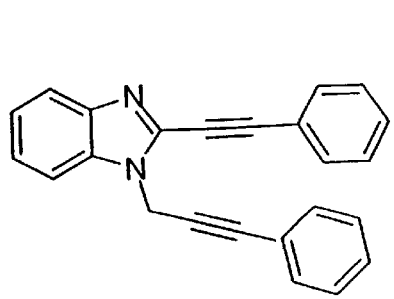
FIG. 24 depicts the structures of KeAZB001, KeAZB002, KeAZB003, KeAZB008, KeAZB009, KeAZB016, and KeAZB017.
Figure 24:
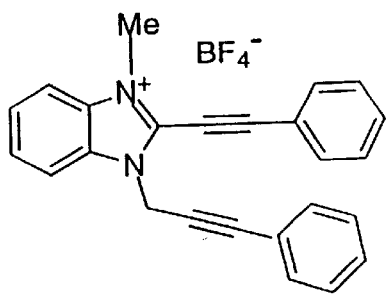
Figure 24:
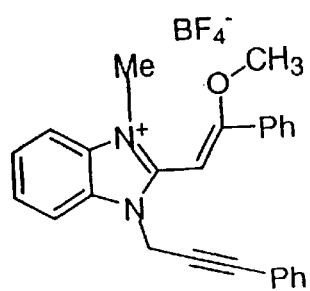
Figure 24:
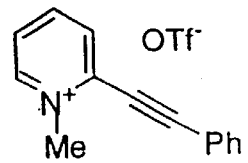
Figure 24:
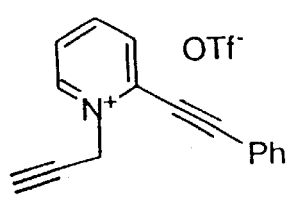
Figure 24:
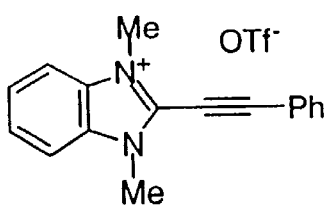
Figure 24:
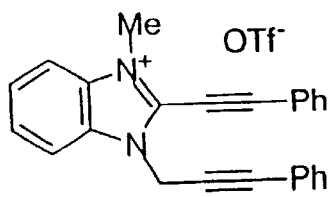
Figure 25:
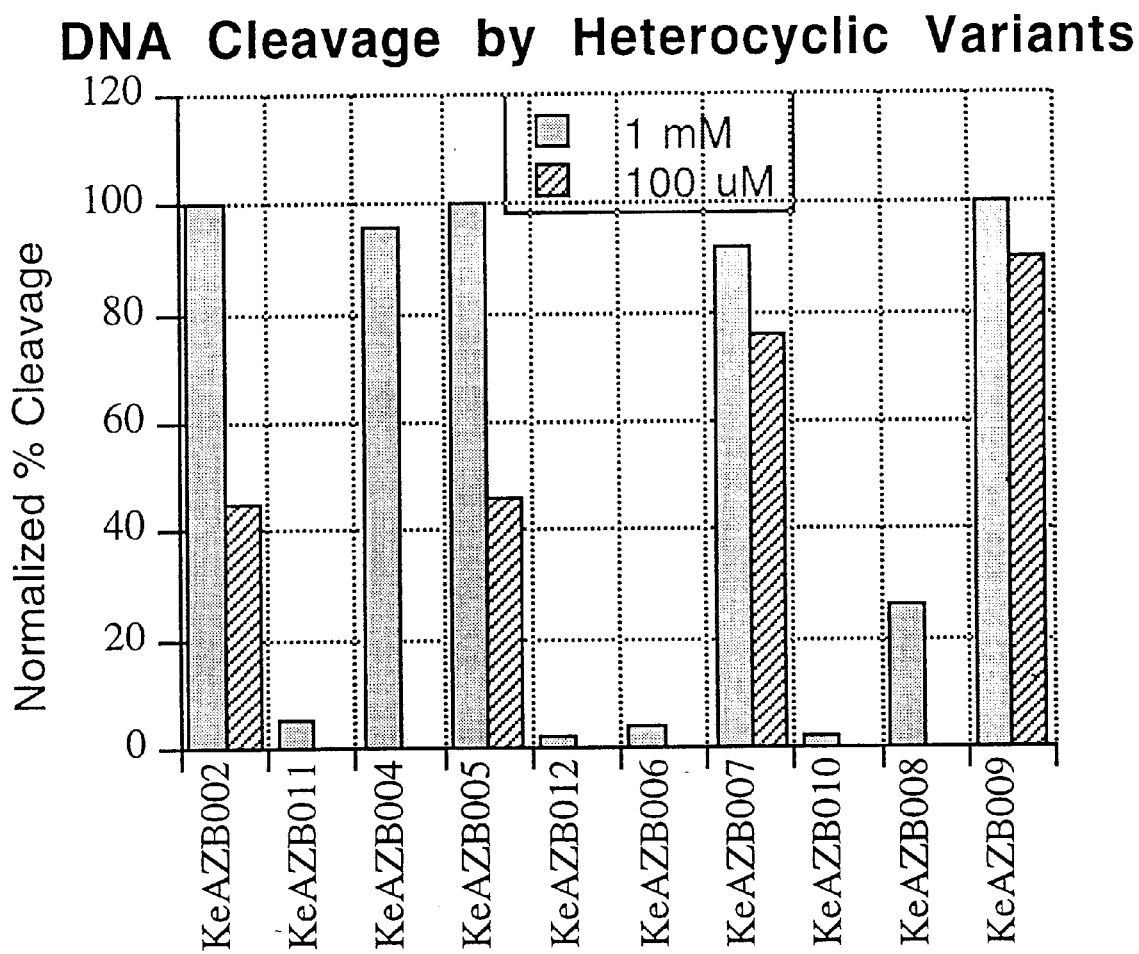
FIG. 25 depicts the normalized percent cleavage of DNA by the heterocyclic variants of FIG. 24.
Figure 26A:
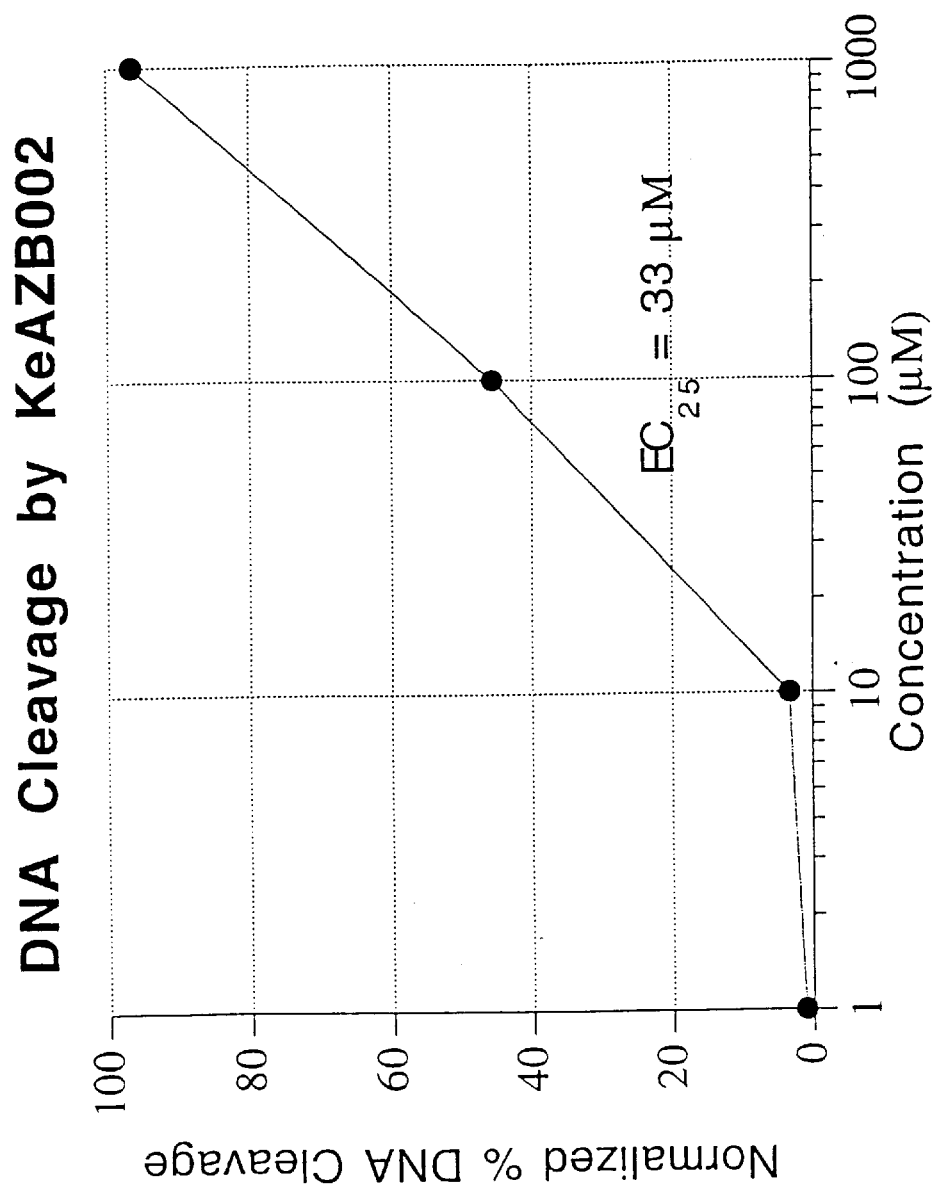
FIG. 26 depicts the normalized percent DNA cleavage vs. concentration for KeAZB002 (FIG. 26A) and KeAZB009 (FIG. 26B).
Figure 26B:
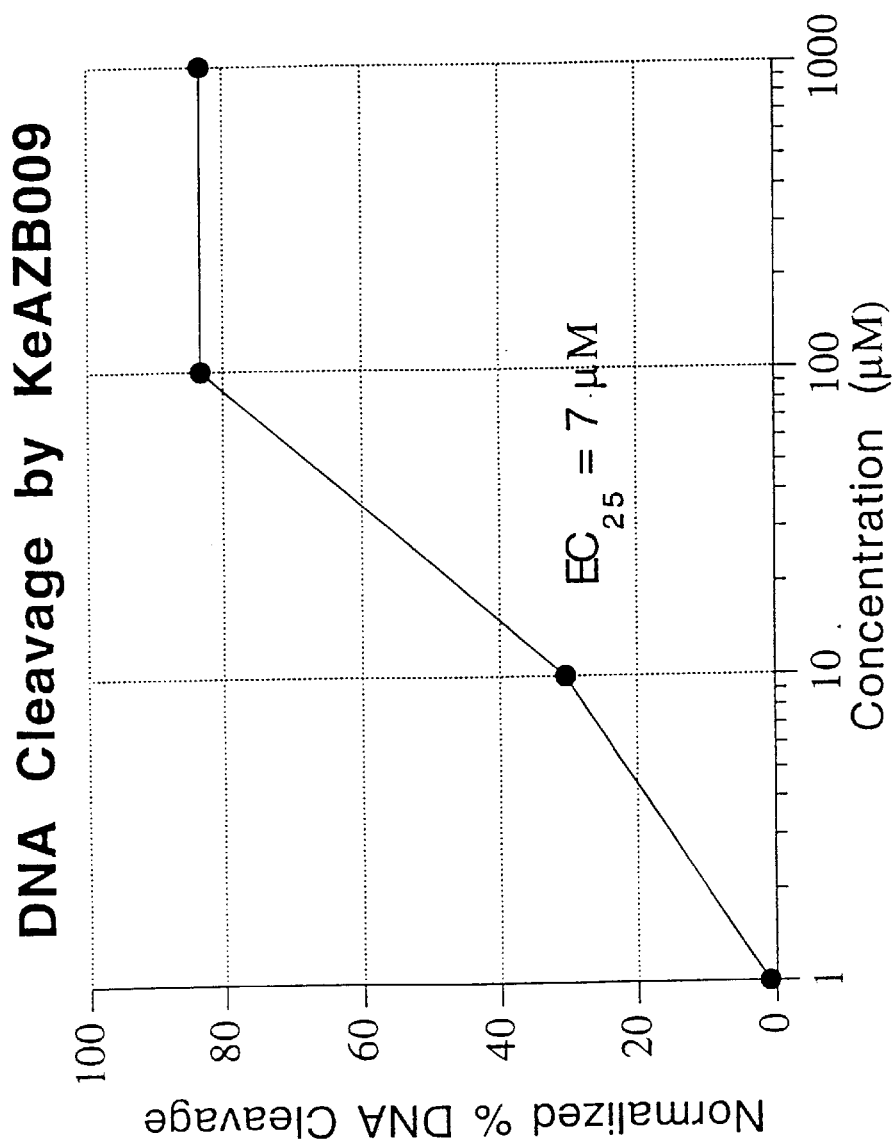

The structures of KeAZB001, KeAZB002, KeAZB003, KeAZB008, KeAZB009, KeAZB016, and KeAZB017 are shown in FIG. 24 and their ability to cleave DNA is shown in FIG. 25. One such compound, KeAZB002 cleaves DNA at micromolar concentrations under mild conditions. This heterocyclic aza-enediyne shows activity against several tumor cell lines in vitro and demonstrates antitumor activity in vivo. Additionally, a pyridine heterocycle, KeAZB009 shows even more potent DNA cleavage than KeAZB002 FIG. 26A and 26B).

EXAMPLE 4

Synthesis of KeAZB002

Figure 12:
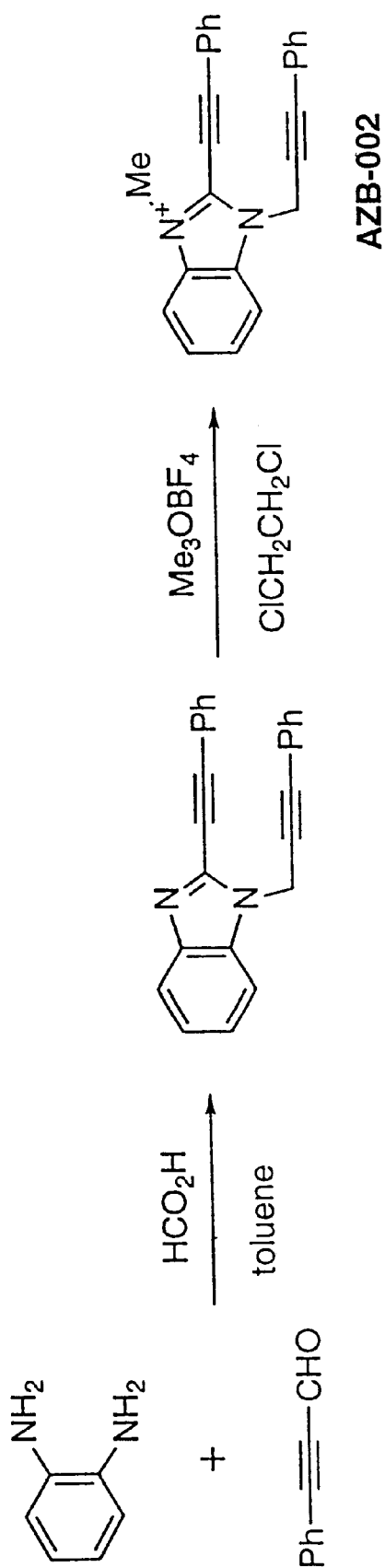
FIG. 12 depicts the synthesis of an aza-enediyne.

Chemicals for synthesis (FIG. 12) were purchased from Aldrich Chemical company and used without further purification, except where noted. Reactions were run under argon using oven-dried glassware. Phenylpropargyl aldehyde (1 mL, 8.18 mmol) was added by syringe to a solution of 1,2-phenylenediamine (437 mg, 4.05 mmol, recrystallized from toluene) in 20 mL anhydrous toluene. A catalytic amount of 88% formic acid (160 μL) was added and the solution was refluxed for 3 hours with the removal of water using a Dean Stark trap. After removal of solvents by rotary evaporation and column chromatography (silica, CHCl$_3$), yellow crystals were obtained by recrystallization from methanol. In a typical procedure, the benzimidazole (87 mg, 0.26 mmol) dissolved in 2 mL distilled 1,2-dichloroethane was added via canula to a solution of trimethyloxoniumtetrafluoroborate (51 mg, 0.34 mmol) in 2 mL distilled 1,2-dichloroethane. The reaction was either refluxed for several hours or allowed to stir at room temperature overnight. The reaction mixture was concentrated to half volume and ether was added to precipitate the product. After refrigeration, the product was filtered. Recrystallization from CH$_2$Cl$_2$/hexanes yielded a tan solid.

Figure 11:
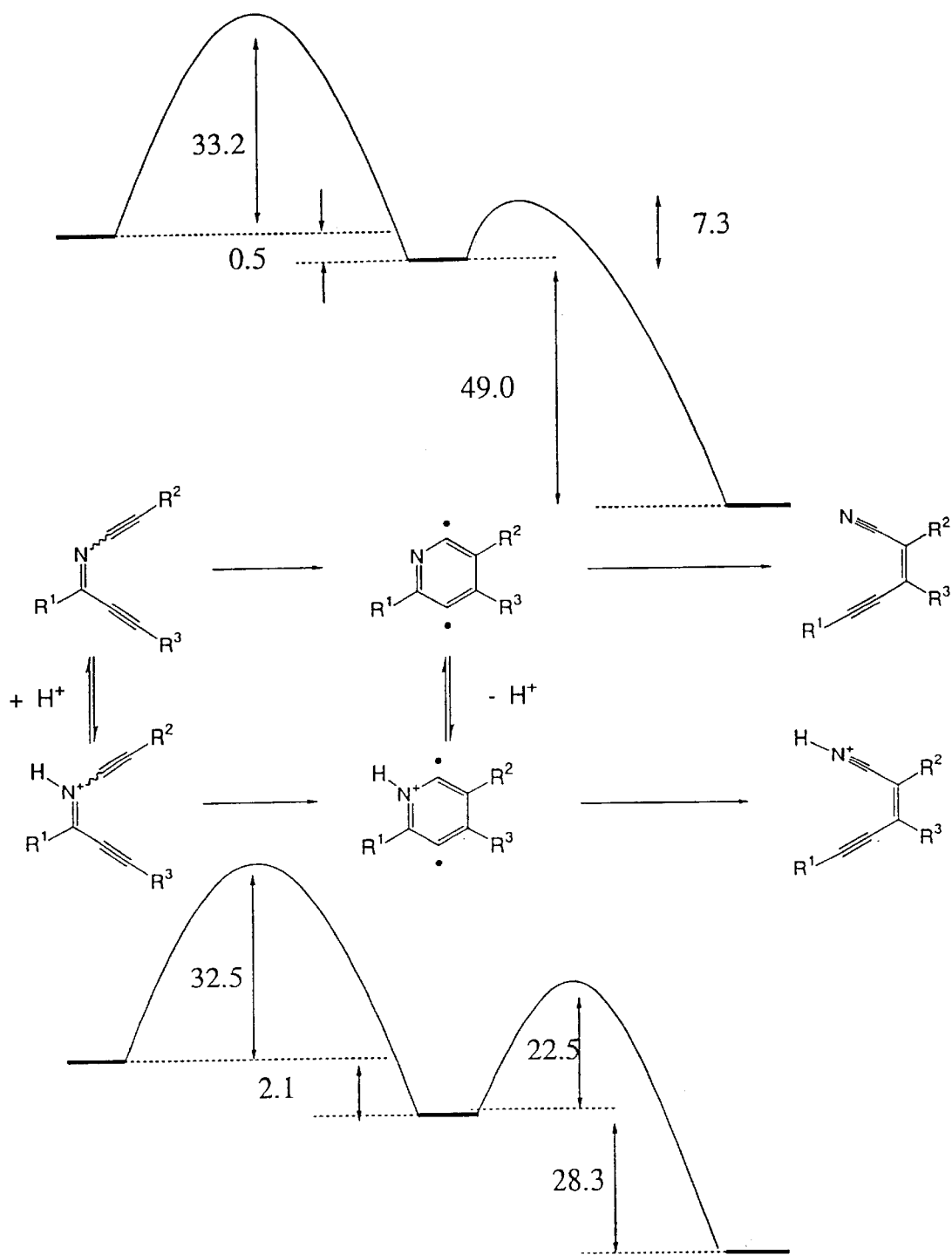
FIG. 11 depicts the energy diagrams of the conversion of enediyne molecules to nitrites.
Figure 13:
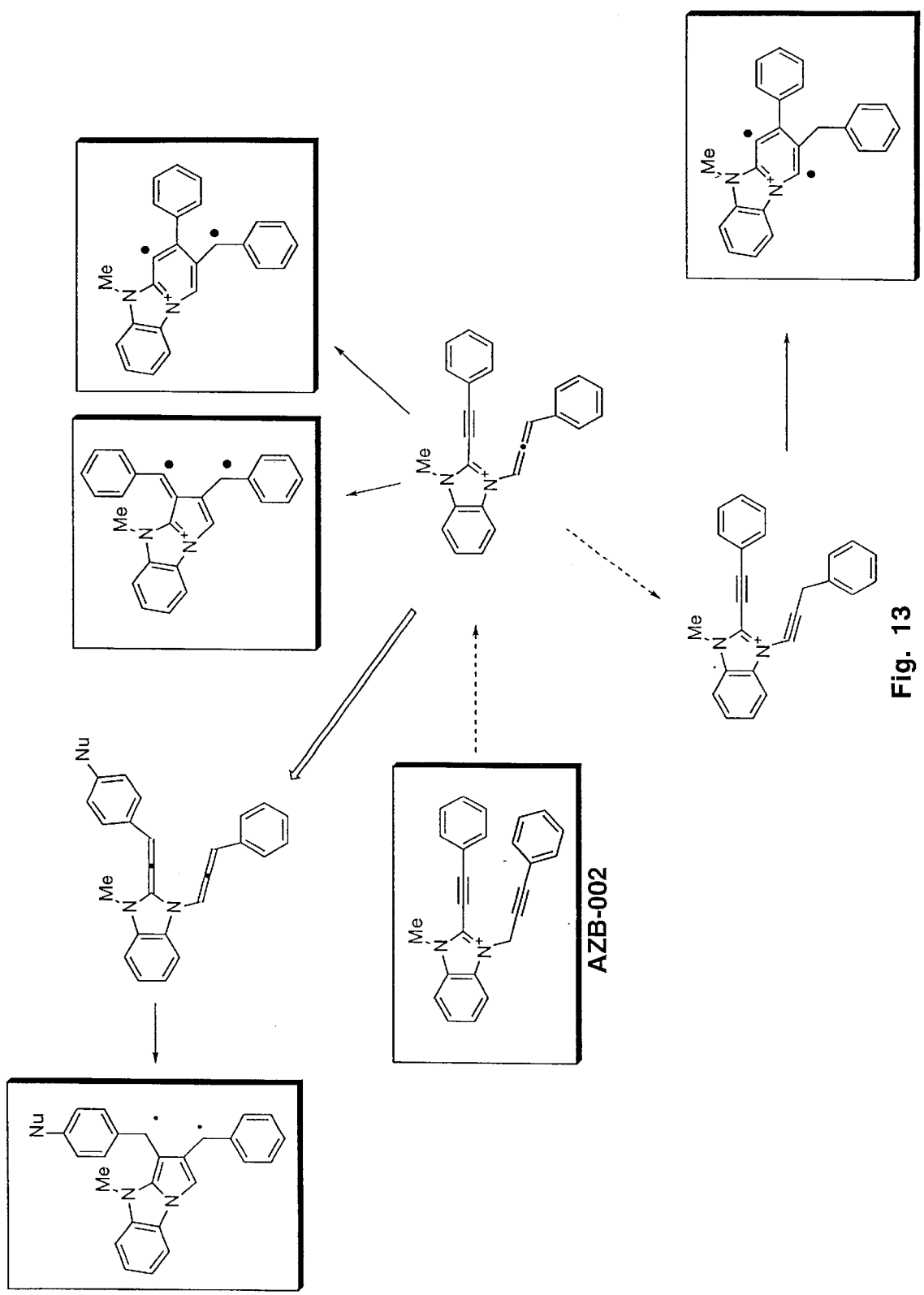
FIG. 13 depicts the reaction of an aza-enediyne.

KeAZB002 is stable indefinitely in water at neutral pH, but undergoes a series of reactions (FIG. 13) in basic aqueous solution. When incubated with supercoiled DNA, KeAZB002 cleaves the DNA, producing frank single strand breaks (FIG. 11). The potency of KeAZB002 in this DNA cleavage assay is equal to that reported for the most advanced synthetic analogs of the enediyne natural product dynemycin.

EXAMPLE 5

DNA cleavage due to KeAZB002

Figure 14:
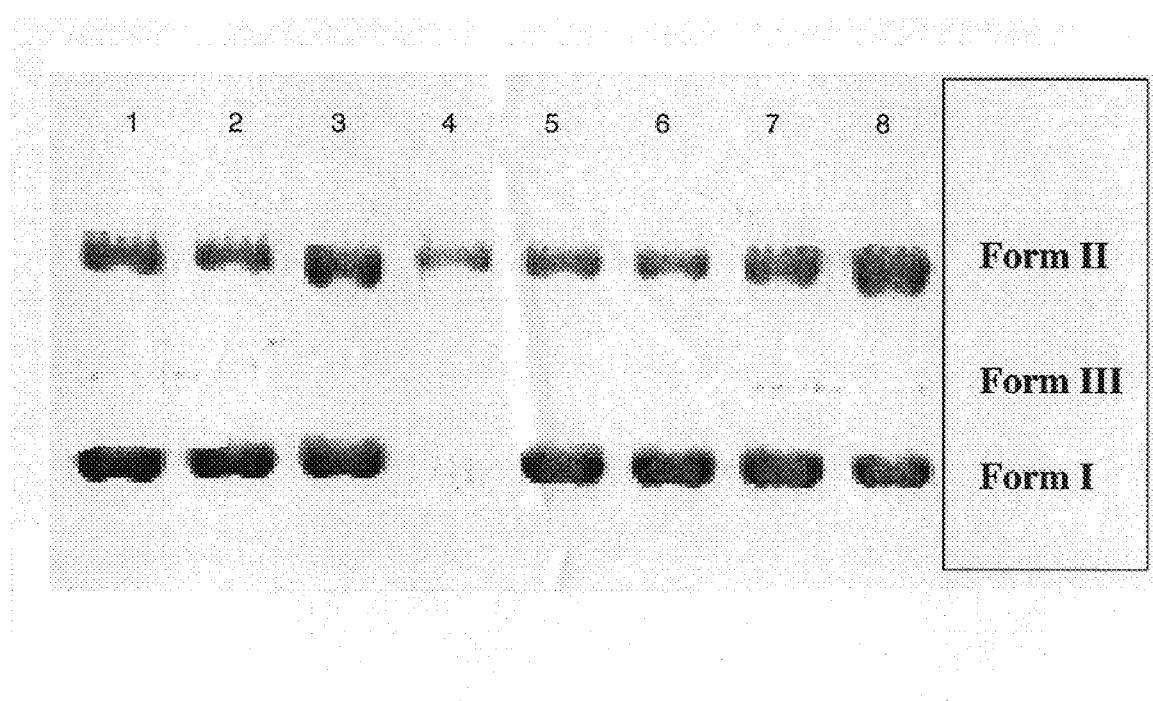
FIG. 14 depicts the results of a DNA cleavage experiment with an aza-enediyne.

The gel depicted in FIG. 14 represents the results of the DNA cleavage experiment with KeAZB002. Supercoiled DNA (50 μM in 50 mM TRIS phosphate buffer, pH 8) was incubated with 0 (lanes 1, 5), 1 (lanes 2, 6), 100 (lanes 3, 7), or 1000 (lane 4) μM of KeAZB002 for 24 hours at 20° C. Samples for lanes 5–8 were loaded onto the agarose gel, whereas samples for lanes 1–4 were heated at 70° C. for 90 sec. prior to loading onto the gel. After electrophoresis at 60 V for 2 hrs, the DNA products were visualized with ethidium bromide staining and UV transillumination.

DNA cleavage by KeAZB002 does not require heat or base treatment subsequent to incubation with the compound. However, DNA cleavage by KeAZB002 is strongly temperature dependent and the percentage of DNA cleavage is higher as basicity increases. Additionally, sodium azide strongly inhibits DNA cleavage by KeAZB002 with cimetidine and potassium bromide effecting percentage cleavage to a much lesser degree (data not shown).

EXAMPLE 6

In vitro and in vivo cytotoxicity studies using KeAZB002

Figure 27:
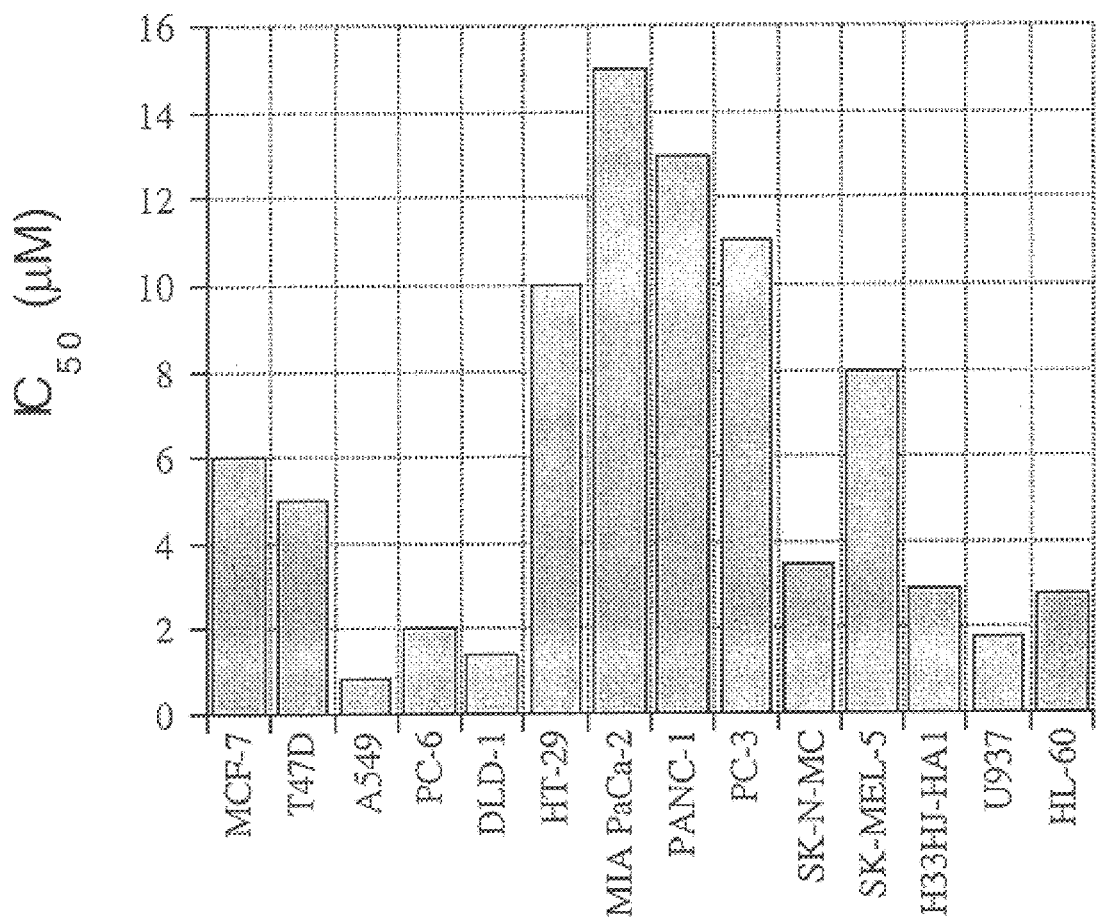
FIG. 27 depicts the in vitro cytotoxic effects of KeAZB002 on various cancer cell lines.

In vitro KeAZB002 is cytotoxic to a variety of cancer cell types (FIG. 27) especially the non-small cell lung cancer cell line A549 and lymphoma cell lines. The compound selectively inhibits growth of cancer cells with high inducible levels of the tumor suppressor gene mdm-2 suggesting that KeAZB002 induces apoptosis and that the interaction with mdm-2 may involve apoptotic signaling pathways.

Figure 28:
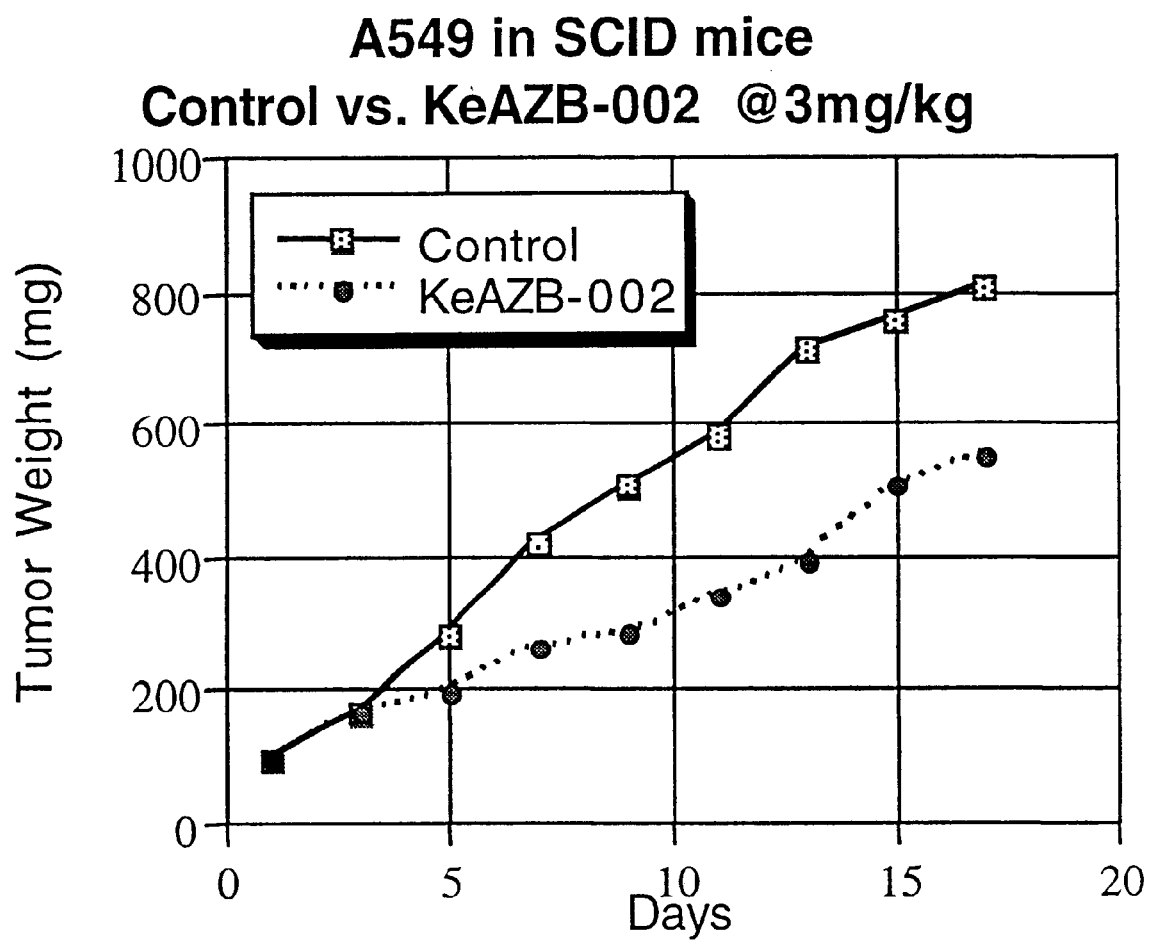
FIG. 28 depicts the effects of KeAZB002 on tumor weight in SCID mice implanted with A549 non-small cell lung cancer cells.

An in vivo evaluation of KeAZB002 against SCID mice implanted with A549 cells demonstrates that the compound has modest antitumor activity in this murine model system; tumor is weight decreased consistently in comparison to control with administration of KeAZB002 over the course of seventeen days (FIG. 28).

EXAMPLE 7

DNA cleavage studies of thiazolium and benzothiazolium salts containing an 4-aza-3-ene-1, 6-diyne moiety The DNA cleavage efficiency of aza-enediyne heterocycles is determined by incubating the azaenediynes with supercoiled plasmid DNA. The supercoiled DNA was diluted to 50 μM bp in 50 mM TRIS buffer at pH 8.0. DNA cleavage reaction mixtures (30 μL) containing 100 μM or 1 mM azaenediyne heterocycles (13% v/v DMSO-$d_6$ final concentration) were incubated for 24 hrs at 37° C. DNA topoisomers were separated by electrophoresis (0.8% agarose, 1x TBE, 82V, 1 hr 10 min) and stained with ethidium bromide (0.25 μg/mL) and images were analyzed by phosphorimger. DNA cleavage normalized for the small amount (10–25%) of nicked relaxed DNA in control samples (DMSO-only treated DNA) is reported. (TABLE 4)

TABLE 3

FACTORS AFFECTING REACTIVITY TO NUCLEOPHILES

| Structure | NMR Solvent | C≡C Chemical Shift | Stability in MeOH (Initial Decomposition) | DNA Cleavage 100 μM | DNA Cleavage 1 mM |
|---|---|---|---|---|---|
| TfO⁻ benzothiazolium-C≡C-phenyl | $CD_2Cl_2$ | 73.25 76.52 78.03 114.96 | ~30 min | 46% | 100% |
| TfO⁻ benzothiazolium-C≡C-C₆H₄-CH₃ | $CD_2Cl_2$ | 73.19 76.49 78.02 114.89 | 20–30 min | nd | 100% |
| TfO⁻ N-CH₃ benzothiazolium-C≡C-phenyl | $CDCl_3$ + DMSO-$d_6$ | 75.02 116.08 | 10–15 min | nd | 96% |

TABLE 3-continued
FACTORS AFFECTING REACTIVITY TO NUCLEOPHILES
| Structure | NMR Solvent | C≡C Chemical Shift | Stability in MeOH (Initial Decomposition) | DNA Cleavage 100 μM | DNA Cleavage 1 mM |
|---|---|---|---|---|---|
| 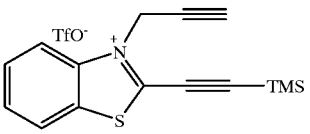 | CDCl$_3$ | 72.85<br>77.42<br>88.00<br>117.48 | 10–15 min | nd | 100% |
| 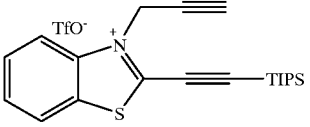 | CD$_2$Cl$_2$ | 72.86<br>78.01<br>90.37<br>117.79 | >24 hr | nd | 0% |
| 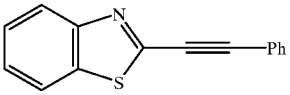 | CDCl$_3$ | | >24 hr | nd | 5% |
| 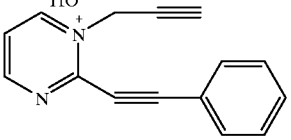 | CD$_2$Cl$_2$ | 72.73<br>80.82<br>81.09<br>109.04 | >24 hr | 14.4% | 43.3% |
| 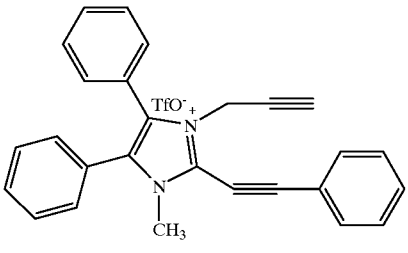 | CDCl$_3$ | 70.17<br>75.25<br>75.73<br>107.95 | >24 hr | 1.4% | 10% |
| 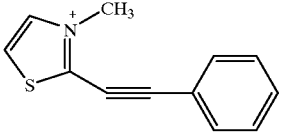 | CDCl$_3$ | 74.40<br>113.10 | | nd | 27% |
| 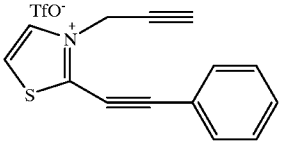 | CDCl$_3$ + DMSO-d$_6$ | 72.96<br>74.00<br>78.53<br>114.59 | ~24 hr | 76% | 100% |
| 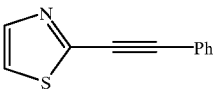 | CDCl$_3$ | | >24 hr | nd | 1.5% |

TABLE 4

NORMALIZATION OF DNA CLEAVAGE TO NICKED RELAXED DNA

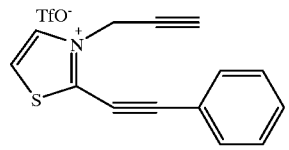

| Sr. No. | Concentration ($\mu$M) | Normalized Cleavage (%) |
|---|---|---|
| 1 | 25 | 37.31 |
| 2 | 50 | 56.84 |
| 3 | 100 | 67.29 |
| 4 | 250 | 92.79 |

The heterocyclic salts all demonstrate some level of DNA cleavage activity, whereas the neutral thiazole and benzothiazole analogs have little DNA cleavage activity. The thiazole- and benzothizole-derived salts are in general more potent DNA cleavage agents than the imidazole or pyrimidine derivatives. Within the benzothiazolium and thiazolium heterocyclic series, the N-methyl salts cleave DNA less well than the N-propargyl salts, and this difference is more pronounced in the thiazolium series as compared to the benzothiazolium series. The DNA cleavage potential of N-propargyl benzothiazolium salts also depends upon the nature of the 2-substituent. Salts bearing a sterically demanding substituent on the terminus of the 2-alkyne moiety are less able to cleave DNA as compared to those salts with smaller groups at this position. Within the benzothiazolium salt series, there is a correlation between DNA cleavage potency and the degree of instability of the methanolic salt solutions. However, the relatively stable N-propargyl thiazolium salt cleaves DNA as well as the less stable benzothiazolium analogs. In the benzothiazolium series of compounds DNA cleavage reactions appear to utilize an electrophilic mechanism while that of the benzimidazolium and pyridinium series may be non-electrophilic.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A chemical composition comprising an iminium ion of an aza-derivative having the structure $R^4R^3C=NR^1R^2$ wherein $R^1$ is independently alkyl or $R^{10}$ and $R^4$ is a substituted-ethynyl group having the structure —C≡C($R^5$), or a substituted-alkenyl group having the structure —CH=$CR^5R^{11}$;

wherein $R^{10}$ is a substituted ethynyl, substituted allenyl, or substituted propargyl;

wherein $R^{11}$ is $OR^{12}$, $SR^{12}$, $N_3$, alkyl, or aryl and $R^{12}$ is hydrogen, alkyl, phenyl, aryl, or aryl ($C_1$–$C_4$) alkyl wherein $R^2$ is a substituted-ethynyl group having the structure —C≡C—$R^5$, a substituted-allenyl group having the structure —$CR^5$=C=$CR^6R^7$, a substituted-propargyl group having the structure —$CR^5R^6$—C≡C—$R^7$, hydrogen, alkyl, phenyl, aryl, aryl ($C_1$–$C_4$) alkyl, or a heterocycle substituent;

wherein in each instance $R^5$, $R^6$, and $R^7$ are independently hydrogen, alkyl, alkenyl, alkynyl, cycloalkyl, alkyl carbonyl, alkoxy carbonyl, phenyl, aryl, aryl ($C_1$–$C_4$) alkyl, hydroxy alkyl, a substituted hydroxyalkyl, an alkyl carboxylic acid derivative, an alkenyl carboxylic acid derivative, a nucleic acid interactive compound, a phosphine oxide, a sulfoxide, a sulfone, a heterocycle substituent, a carbocyclic substituent, one or more aza-derivatives, or where $R^5$, $R^6$, and $R^7$ can join with themselves or each other to form a 9–26 membered ring; and wherein $R^3$ is —$SR^8$, —$NR^8R^9$, or —$CR^8R^9$ wherein in each instance $R^8$ and $R^9$ are independently a hydrogen, alkyl, phenyl, aryl, aryl ($C_1$–$C_4$) alkyl, trifluoromethylsulfonyl, silyl, substituted-ethynyl, substituted-allenyl, substituted propargyl, a sugar, a C-glycoside, a nucleic acid interactive compound, or a heterocycle substituent;

wherein $R^2$ and $R^3$ along with parent iminium combine to form a substituted heterocyclic ring; and wherein said compound is associated with a counter ion.

2. The compound of claim 1, wherein $R^2$ and $R^3$ along with the parent iminium combine to form a benzimidazole, thiazole, benzthiazole, imidazole, pyrimidine, or pyridinium ring.

3. The compound of claim 2, wherein $R^1$ is methyl, $R^4$ is —C≡—C(Ph), and $R^3$ is $NR^8R^9$ wherein $R^9$ is methyl and wherein $R^2$ and $R^3$ along with the parent iminium combine to form a substituted benzimidazole ring.

4. The compound of claim 2, wherein $R^1$ is methyl, $R^4$ is —CH=C(Ph)$OCH_3$ and $R^3$ is $NR^8R^9$ wherein $R^9$ methyl and wherein $R^2$ and $R^3$ along with the parent iminium combine to form a substituted benzimidazole ring.

5. The compound of claim 2, wherein $R^1$ is methyl, $R^4$ is —C≡C(Ph) and $R^3$ is $SR^8$ wherein $R^2$ and $R^3$ along with the parent iminium combine to form a substituted benzthiazole ring.

6. The compound of claim 2, wherein $R^1$ is methyl, $R^4$ is —CH=C(Ph)$OCH_3$ and $R^3$ is $SR^8$ wherein $R^2$ and $R^3$ along with the parent iminium combine to form a substituted benzthiazole ring.

7. The compound of claim 2, wherein $R^1$ is methyl, $R^4$ is —C≡C(Ph) and $R^3$ is $SR^8$ wherein $R^2$ and $R^3$ along with the parent iminium combine to form a substituted thiazole ring.

8. The compound of claim 2, wherein $R^1$ is methyl, $R^4$ is —C≡C(Ph) and $R^3$ is $NR^8R^9$ wherein $R^2$ and $R^3$ along with the parent iminium combine to form an imidazole ring.

9. The compound of claim 2, wherein $R^1$ is methyl, $R^4$ is —C≡C(Ph) and $R^3$ is $NR^8R^9$; wherein $R^9$ is methyl and wherein $R^2$ and $R^3$ along with the parent iminium combine to form a pyridinium ring.

10. The compound of claim 2, wherein $R^1$ is methyl, $R^4$ is —C≡C(Ph) and $R^3$ is $NR^8R^9$ wherein $R^9$ is methyl and wherein $R^2$ and $R^3$ along with the parent iminium combine to form a pyridinium ring.

11. The compound of claim 1, wherein the nucleic acid interactive compound is an oligonucleic acid, a peptide, a peptoid, an intercalator, a crown ether, a peptide nucleic acid, a G-quadruplex interactive agent, a triplex interactive agent, an RNA interactive agent, an RNA-DNA heteroduplex interactive agent, a DNA alkylating agent, an RNA alkylating agent, a DNA cleaving agent, an RNA cleaving agent, a DNA metalating agent, an RNA metalating agent, a DNA groove binding compound, a porphyrin, an aminoglycoside, a sugar, or an oligosaccharide.

12. The compound of claim 1, wherein said counter ion is selected from the group consisting of fluorine, chlorine, bromine, iodine, tetrafluoroborane, acetate, sulfonate, and phosphate.

13. The compound of claim 1, wherein the compound is capable of producing a diradical intermediate at physiological conditions.

14. The compound of claim 1, wherein the compound binds to nucleic acids.

15. The compound of claim 1, wherein the compound binds to nucleic acids, and wherein the compound is configured to effect nucleic acid cleavage.

16. An oligomeric chemical composition comprising a compound, the compound comprising at least two covalently coupled iminium ions of aza-derivatives, wherein the aza derivatives have the structure $R^4R^3C=NR^1R^2$;

wherein $R^1$ is independently alkyl or $R^{10}$ and $R^4$ is a substituted-ethynyl group having the structure —C≡C ($R^5$), or a substituted-alkenyl group having the structure —CH=$CR^5R^{11}$;

wherein $R^{10}$ is a substituted ethynyl, substituted allenyl, or substituted propargyl;

wherein in $R^{11}$ is $OR^{12}$, $SR^{12}$, $N_3$, alkyl, or aryl and $R^{12}$ is hydrogen, alkyl, phenyl, aryl, or aryl ($C_1$–$C_4$) alkyl wherein $R^2$ is a substituted-ethynyl group having the structure —C≡C—$R^5$, a substituted-allenyl group having the structure —$CR^5$=C=$CR^6R^7$, a substituted-propargyl group having the structure —$CR^5R^6$—C≡C—$R^7$, hydrogen, alkyl, phenyl, aryl, aryl ($C_1$–$C_4$) alkyl, or a heterocycle substituent;

wherein in each instance $R^5$, $R^6$, and $R^7$ are independently hydrogen, alkyl, alkenyl, alkynyl, cycloalkyl, alkyl carbonyl, alkoxy carbonyl, phenyl, aryl, aryl ($C_1$–$C_4$) alkyl, hydroxy alkyl, a substituted hydroxyalkyl, an alkyl carboxylic acid derivative, an alkenyl carboxylic acid derivative, a nucleic acid interactive compound, a phosphine oxide, a sulfoxide, a sulfone, a heterocycle substituent, a carbocyclic substituent, one or more aza-derivatives, or where $R^5$, $R^6$, and $R^7$ can join with themselves or each other to form a 9–26 membered ring; and wherein $R^3$ is —$SR^8$, —$NR^8R^9$, or —$CR^8R^9$ wherein in each instance $R^8$ and $R^9$ are independently a hydrogen, alkyl, phenyl, aryl, aryl ($C_1$–$C_4$) alkyl, trifluoromethylsulfonyl, silyl, substituted-ethynyl, substituted-allenyl, substituted propargyl, a sugar, a C-glycoside a nucleic acid interactive compound, or a heterocycle substituent;

wherein $R^2$ and $R^3$ along with parent iminium combine to form a substituted heterocyclic ring; and wherein said compound is associated with a counter ion; and wherein $R^2$, $R^3$ and $R^5$ of one aza-derivative may be covalently linked to the corresponding $R^2$, $R^3$ and $R^5$ of the second aza-derivative through a linking group, wherein the linking group is a single bond, alkyl, alkenyl, alkynyl, cycloalkyl, alkyl carbonyl, alkoxy carbonyl, phenyl, aryl, a heterocyclic ring, a substituted heterocyclic ring, a heteroatom substituent, hydroxyalkyl, a substituted hydroxyalkyl, an alkyl carboxylic acid derivative, or an alkenyl carboxylic acid derivative.

17. The compound of claim 16, wherein $R^2$ of one aza-derivative independently connects to $R^2$ of the second aza-derivative through a linking group and $R^3$ of one aza-derivative independently connects to $R^3$ of the second aza-derivative through a linking group wherein the linking group is a single bond, alkyl, alkenyl, alkynyl, cycloalkyl, alkyl carbonyl, alkoxy carbonyl, phenyl, aryl, a heterocyclic ring, a heteroatom substituent, hydroxyalkyl, a substituted hydroxyalkyl, an alkyl carboxylic acid derivative, or an alkenyl carboxylic acid derivative.

18. The compound of claim 16, wherein $R^4$ is —C≡C (Ph) wherein $R^2$ of one aza-derivative independently connects to $R^2$ of the second aza-derivative through a linking group wherein the linking group is a single bond, alkyl, alkenyl, alkynyl, cycloalkyl, alkyl carbonyl, alkoxy carbonyl, phenyl, aryl, a heterocyclic ring, a heteroatom substituent, hydroxyalkyl, a substituted hydroxyalkyl, an alkyl carboxylic acid derivative, or an alkenyl carboxylic acid derivative and $R^3$ is not a linking group but is as previously described.

19. The compound of claim 16, wherein $R^4$ is —C≡C (Ph); wherein $R^3$ of one aza-derivative independently connects to $R^3$ of the second aza-derivative through a linking group wherein the linking group is a single bond, alkyl, alkenyl, alkynyl, cycloalkyl, alkyl carbonyl, alkoxy carbonyl, phenyl, aryl, a heterocyclic ring, a heteroatom substituent, hydroxyalkyl, a substituted hydroxyalkyl, an alkyl carboxylic acid derivative, or an alkenyl carboxylic acid derivative and $R^3$ is not a linking group but is as previously described.

20. The compound of claim 16, wherein $R^4$ is —CH=C (Ph)$OCH_3R^3$; wherein $R^2$ of one aza-derivative independently connects to $R^2$ of the second aza-derivative through a linking group wherein the linking group is a single bond, alkyl, alkenyl, alkynyl, cycloalkyl, alkyl carbonyl, alkoxy carbonyl, phenyl, aryl, a heterocyclic ring, a heteroatom substituent, hydroxyalkyl, a substituted hydroxyalkyl, an alkyl carboxylic acid derivative, or an alkenyl carboxylic acid derivative and $R^2$ is not a linking group but is as previously described.

21. The compound of claim 16, wherein $R^4$ is —CH=C (Ph)$OCH_3R^3$; wherein $R^3$ of one aza-derivative independently connects to $R^3$ of the second aza-derivative through a linking group wherein the linking group is a single bond, alkyl, alkenyl, alkynyl, cycloalkyl, alkyl carbonyl, alkoxy carbonyl, phenyl, aryl, a heterocyclic ring, a heteroatom substituent, hydroxyalkyl, a substituted hydroxyalkyl, an alkyl carboxylic acid derivative, or an alkenyl carboxylic acid derivative and $R^2$ is not a linking group but is as previously described.

22. A pharmaceutical composition comprising an iminium ion of an aza-derivative having the structure $R^4R^3C=NR^1R^2$ wherein $R^1$ is independently alkyl or $R^{10}$ and $R^4$ is a substituted-ethynyl group having the structure —C≡C ($R^5$), or a substituted-alkenyl group having the structure —CH=$CR^5R^{11}$;

wherein $R^{10}$ is a substituted ethynyl, substituted allenyl, or substituted propargyl wherein in $R^{11}$ is $OR^{12}$, $SR^{12}$, $N_3$, alkyl, or aryl and $R^{12}$ is hydrogen, alkyl, phenyl, aryl, or aryl ($C_1$–$C_4$) alkyl wherein $R^2$ is a substituted-ethynyl group having the structure —C≡C—$R^5$, a substituted-allenyl group having the structure —CR$^5$=C=CR$^6$R$^7$, a substituted-propargyl group having the structure —CR$^5$R$^6$—C≡C—R$^7$, hydrogen, alkyl, phenyl, aryl, aryl (C$_1$–C$_4$) alkyl, or a heterocycle substituent;

wherein in each instance R$^5$, R$^6$, and R$^7$ are independently hydrogen, alkyl, alkenyl, alkynyl, cycloalkyl, alkyl carbonyl, alkoxy carbonyl, phenyl, aryl, aryl (C$_1$–C$_4$) alkyl, hydroxy alkyl, a substituted hydroxyalkyl, an alkyl carboxylic acid derivative, an alkenyl carboxylic acid derivative, a nucleic acid interactive compound, a phosphine oxide, a sulfoxide, a sulfone, a heterocycle substituent, a carbocyclic substituent, one or more aza-derivatives, or where R$^5$, R$^6$, and R$^7$ can join with themselves or each other to form a 9–26 membered ring; and wherein R$^3$ is —SR$^8$, —NR$^8$R$^9$, or —CR$^8$R$^9$ wherein in each instance R$^1$ and R$^9$ are independently a hydrogen, alkyl, phenyl, aryl, aryl (C$_{1-C4}$) alkyl, trifluoromethylsulfonyl, silyl, substituted-ethynyl, substituted-allenyl, substituted propargyl, a sugar, a C-glycoside, a nucleic acid interactive compound, or a heterocycle substituent;

wherein R$^2$ and R$^3$ along with parent iminium combine to form a substituted heterocyclic ring; and wherein said compound is associated with a counter ion.

23. The composition of claim 22, wherein R$^2$ and R$^3$ along with the parent iminium combine to form a benzimidazole, thiazole, benzthiazole, imidazole, pyrimidine, or pyridinium ring.

24. The compound of claim 23, wherein R$^1$ is methyl, R$^4$ is —C≡C(Ph), and R$^3$ is NR$^8$R$^9$ wherein R$^9$ is methyl and wherein R$^2$ and R$^3$ along with the parent iminium combine to form a substituted benzimidazole ring.

25. The compound of claim 23, wherein R$^1$ is methyl, R$^4$ is —CH=C(Ph)OCH$_3$ and R$^3$ is NR$^8$R$^9$ wherein R$^9$ methyl and wherein R$^2$ and R$^3$ along with the parent iminium combine to form a substituted benzimidazole ring.

26. The compound of claim 23, wherein R$^1$ is methyl, R$^4$ is —C≡C(Ph) and R$^3$ is SR$^8$ wherein R$^2$ and R$^3$ along with the parent iminium combine to form a substituted benzthiazole ring.

27. The compound of claim 23 wherein R$^1$ is methyl, R$^4$ is —CH=C(Ph)OCH$_3$ and R$^3$ is SR$^8$ wherein R$^2$ and R$^3$ along with the parent iminium combine to form a substituted benzthiazole ring.

28. The compound of claim 23, wherein R$^1$ is methyl, R$^4$ is —C≡C(Ph) and R$^3$ is SR$^8$ wherein R$^2$ and R$^3$ along with the parent iminium combine to form a substituted thiazole ring.

29. The compound of claim 23, wherein R$^1$ is methyl, R$^4$ is —C≡C(Ph) and R$^3$ is NR$^8$R$^9$ wherein R$^2$ and R$^3$ along with the parent iminium combine to form an imidazole ring.

30. The compound of claim 23, wherein R$^1$ is methyl, R$^4$ is —C≡C(Ph) and R$^3$ is NR$^8$R$^9$; wherein R$^9$ is methyl and wherein R$^2$ and R$^3$ along with the parent iminium combine to form a pyridinium ring.

31. The composition of claim 22, wherein the nucleic acid interactive compound is an oligonucleic acid, a peptide, a peptoid, an intercalator, a crown ether, a peptide nucleic acid, a G-quadruplex interactive agent, a triplex interactive agent, an RNA interactive agent, an RNA-DNA heteroduplex interactive agent, a DNA alkylating agent, an RNA alkylating agent, a DNA cleaving agent, an RNA cleaving agent, a DNA metalating agent, an RNA metalating agent, a DNA groove binding compound, a porphyrin, an aminoglycoside, a sugar, or an oligosaccharide.

32. The composition of claim 22, wherein said counter ion is selected from the group consisting of fluorine, chlorine, bromine, iodine, tetrafluoroborane, acetate, sulfonate, and phosphate.

33. A pharmaceutical composition comprising an aza-derivative comprising an oligomeric chemical composition comprising a compound of at least two covalently coupled iminium ions of aza-derivatives, wherein the aza derivatives have the structure R$^4$R$^3$C=NR$^1$R$^2$;

wherein R$^1$ is independently alkyl or R$^{10}$ and R$^4$ is a substituted-ethynyl group having the structure —C≡C(R$^5$), or a substituted-alkenyl group having the structure —CH=CR$^5$R$^1$;

wherein R$^{10}$ is a substituted ethynyl, substituted allenyl, or substituted propargyl wherein in R$^{11}$ is OR$^{12}$, SR$^{12}$, N$_3$, alkyl, or aryl and R$^{12}$ is hydrogen, alkyl, phenyl, aryl, or aryl (C$_1$–C$_4$) alkyl wherein R$^2$ is a substituted-ethynyl group having the structure —C≡C—R$^5$, a substituted-allenyl group having the structure —CR$^5$=C=CR$^6$R$^7$, a substituted-propargyl group having the structure —CR$^5$R$^6$—C≡C—R$^7$, hydrogen, alkyl, phenyl, aryl, aryl (C$_1$–C$_4$) alkyl, or a heterocycle substituent;

wherein in each instance R$^5$, R$^6$, and R$^7$ are independently hydrogen, alkyl, alkenyl, alkynyl, cycloalkyl, alkyl carbonyl, alkoxy carbonyl, phenyl, aryl, aryl (C$_1$–C$_4$) alkyl, hydroxy alkyl, a substituted hydroxyalkyl, an alkyl carboxylic acid derivative, an alkenyl carboxylic acid derivative, a nucleic acid interactive compound, a phosphine oxide, a sulfoxide, a sulfone, a heterocycle substituent, a carbocyclic substituent, one or more aza-derivatives, or where R$^5$, R$^6$, and R$^7$ can join with themselves or each other to form a 9–26 membered ring; and wherein R$^3$ is —SR$^8$, —NR$^8$R$^9$, or —CR$^8$R$^9$ wherein in each instance R$^8$ and R$^9$ are independently a hydrogen, alkyl, phenyl, aryl, aryl (C$_1$–C$_4$) alkyl, trifluoromethylsulfonyl, silyl, substituted-ethynyl, substituted-allenyl, substituted propargyl, a sugar, a C-glycoside, a nucleic acid interactive compound, or a heterocycle substituent;

wherein R$^2$ and R$^3$ along with parent iminium combine to form a substituted heterocyclic ring; and wherein said compound is associated with a counter ion and wherein R$^2$, R$^3$ and R$^5$ of one aza-derivative may be covalently linked to the corresponding R$^2$, R$^3$ and R$^5$ of the second aza-derivative through a linking group, wherein the linking group is a single bond, alkyl, alkenyl, alkynyl, cycloalkyl, alkyl carbonyl, alkoxy carbonyl, phenyl, aryl, a heterocyclic ring, a substituted heterocyclic ring, a heteroatom substituent, hydroxyalkyl, a substituted hydroxyalkyl, an alkyl carboxylic acid derivative, or an alkenyl carboxylic acid derivative.

34. A method of treating a disease state with a chemical composition comprising an iminium ion of an aza-derivative, comprising administering the salt of the aza-derivative to the patient;

wherein the aza derivative has the structure R$^4$R$^3$C=NR$^1$R$^2$ wherein R$^1$ is independently alkyl or R$^{10}$ and R$^4$ is a substituted-ethynyl group having the structure —C≡C(R$^5$), or a substituted-alkenyl group having the structure —CH=CR$^5$R$^{11}$;

wherein R$^{10}$ is a substituted ethynyl, substituted allenyl, or substituted propargyl wherein in R$^{11}$ is OR$^{12}$, SR$^{12}$, N$_3$, alkyl, or aryl and R$^{12}$ is hydrogen, alkyl, phenyl, aryl, or aryl (C$_1$–C$_4$) alkyl wherein R² is a substituted-ethynyl group having the structure —C≡C—R⁵, a substituted-allenyl group having the structure —CR⁵=C=CR⁶R⁷, a substituted-propargyl group having the structure —CR⁵R⁶—C≡C—R⁷, hydrogen, alkyl, phenyl, aryl, aryl (C₁-C₄) alkyl, or a heterocycle substituent;

wherein in each instance R⁵, R⁶, and R⁷ are independently hydrogen, alkyl, alkenyl, alkynyl, cycloalkyl, alkyl carbonyl, alkoxy carbonyl, phenyl, aryl, aryl (C₁-C₄) alkyl, hydroxy alkyl, a substituted hydroxyalkyl, an alkyl carboxylic acid derivative, an alkenyl carboxylic acid derivative, a nucleic acid interactive compound, a phosphine oxide, a sulfoxide, a sulfone, a heterocycle substituent, a carbocyclic substituent, one or more aza-derivatives, or where R⁵, R⁶, and R⁷ can join with themselves or each other to form a 9–26 membered ring; and wherein R³ is —SR⁸, —NR⁸R⁹, or —CR⁸R⁹ wherein in each instance R⁸ and R⁹ are independently a hydrogen, alkyl, phenyl, aryl, aryl (C₁-C₄) alkyl, trifluoromethylsulfonyl, silyl, substituted-ethynyl, substituted-allenyl, substituted propargyl, a sugar, a C-glycoside, a nucleic acid interactive compound, or a heterocycle substituent;

wherein R² and R³ along with parent iminium combine to form a substituted heterocyclic ring; and wherein said compound is associated with a counter ion.

35. The method of claim 34 comprising administering the aza-derivative to the patient, wherein R² and R³ along with the parent iminium combine to form a benzimidazole, thiazole, benzthiazole, imidazole, pyrimidine, or pyridinium ring.

36. The method of claim 35 comprising administering the aza-derivative to the patient, wherein R¹ is methyl, R⁴ is —C≡C(Ph), and R³ is NR⁸R⁹ wherein R⁹ is methyl and wherein R² and R³ along with the parent iminium combine to form a substituted benzimidazole ring.

37. The method of claim 35 comprising administering the aza-derivative to the patient, wherein R¹ is methyl, R⁴ is —CH=C(Ph)OCH₃ and R³ is NR⁸R⁹ wherein R⁹ methyl and wherein R² and R³ along with the parent iminium combine to form a substituted benzimidazole ring.

38. The method of claim 35 comprising administering the aza-derivative to the patient, wherein R¹ is methyl, R⁴ is —C≡C(Ph) and R³ is SR⁸ wherein R² and R³ along with the parent iminium combine to form a substituted benzthiazole ring.

39. The method of claim 35 comprising administering the aza-derivative to the patient, wherein R¹ is methyl, R⁴ is —CH=C(Ph)OCH₃ and R³ is SR⁸ wherein R² and R³ along with the parent iminium combine to form a substituted benzthiazole ring.

40. The method of claim 35 comprising administering the aza-derivative to the patient, wherein R¹ is methyl, R⁴ is —C≡C(Ph) and R³ is SR⁸ wherein R² and R³ along with the parent iminium combine to form a thiazole ring.

41. The method of claim 35 comprising administering the aza-derivaive to the patient, wherein R¹ is methyl, R⁴ is —C≡C(Ph) and R³ is NR⁸R⁹ wherein R² and R³ along with the parent iminium combine to form an imidazole ring.

42. The method of claim 35 comprising administering the aza-derivative to the patient, wherein R¹ is methyl, R⁴ is —C≡C(Ph) and R³ is NR⁸R⁹; wherein R⁹ is methyl and wherein R² and R³ along with the parent iminium combine to form a pyridinium ring.

43. The method of claim 35 comprising administering the aza-derivative to the patient, wherein the nucleic acid interactive compound is an oligonucleic acid, a peptide, a peptoid, an intercalator, a crown ether, a peptide nucleic acid, a G-quadruplex interactive agent, a triplex interactive agent, an RNA interactive agent, an RNA-DNA heteroduplex interactive agent, a DNA alkylating agent, an RNA alkylating agent, a DNA cleaving agent, an RNA cleaving agent, a DNA metalating agent, an RNA metalating agent, a DNA groove binding compound, a porphyrin, an aminoglycoside, a sugar, or an oligosaccharide.

44. The method of claim 35 comprising administering the aza-derivative to the patient, wherein said counter ion is selected from the iminium the group consisting of fluorine, chlorine, bromine, iodine, tetrafluoroborane, acetate, sulfonate, and phosphate.

* * * * *

UNITED STATES PATENT AND TRADEMARK OFFICE
CERTIFICATE OF CORRECTION

PATENT NO. : 6,297,284 B1
DATED : October 2, 2001
INVENTOR(S) : Sean M. Kerwin, Wendi M. Davis and Dalip Kumar It is certified that error appears in the above-identified patent and that said Letters Patent is hereby corrected as shown below:

Title page,
ABSTRACT, "compound" should read -- compounds --.

Column 10,
Line 64, please insert a period after the word "pound".

Column 18,
Line 15, "aza-derivative" should read -- aza-derivatives --.
Line 21, "refers" should read -- refer --.

Column 22,
Line 42, please insert the word -- of -- between the words "components" and "the".

Column 24,
Line 19, "be" should read -- being --.

Column 25,
Line 28, "be" should read -- being --.

Column 28,
Line 18, please insert an open parentheses before the words "e.g. 36".

Column 34,
Line 25, "ylide" should read -- slide --.

UNITED STATES PATENT AND TRADEMARK OFFICE
CERTIFICATE OF CORRECTION

PATENT NO. : 6,297,284 B1
DATED : October 2, 2001
INVENTOR(S) : Sean M. Kerwin, Wendi M. Davis and Dalip Kumar It is certified that error appears in the above-identified patent and that said Letters Patent is hereby corrected as shown below:

Column 41,
Line 32, please insert a semicolon after the word "alkyl".

Signed and Sealed this

Thirtieth Day of April, 2002

Attest:

JAMES E. ROGAN
*Director of the United States Patent and Trademark Office*

*Attesting Officer*